US010899879B2

(12) United States Patent
Maynard

(10) Patent No.: US 10,899,879 B2
(45) Date of Patent: *Jan. 26, 2021

(54) BIODEGRADABLE TREHALOSE GLYCOPOLYMERS

(71) Applicant: THE REGENTS OF THE UNIVERSITY OF CALIFORNIA, Oakland, CA (US)

(72) Inventor: Heather D. Maynard, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 610 days.

This patent is subject to a terminal disclaimer.

(21) Appl. No.: 15/503,350

(22) PCT Filed: Aug. 13, 2015

(86) PCT No.: PCT/US2015/044973
§ 371 (c)(1),
(2) Date: Jun. 11, 2018

(87) PCT Pub. No.: WO2016/025668
PCT Pub. Date: Feb. 18, 2016

(65) Prior Publication Data
US 2018/0312630 A1 Nov. 1, 2018

Related U.S. Application Data

(60) Provisional application No. 62/036,973, filed on Aug. 13, 2014.

(51) Int. Cl.
C08G 63/91 (2006.01)
A61K 38/19 (2006.01)
(Continued)

(52) U.S. Cl.
CPC .......... *C08G 63/912* (2013.01); *A61K 38/193* (2013.01); *A61K 47/24* (2013.01);
(Continued)

(58) Field of Classification Search
CPC .. C08G 63/08; C08G 63/6852; C08G 63/688; C08G 63/6882; C08G 63/91;
(Continued)

(56) References Cited

U.S. PATENT DOCUMENTS 10,273,333 B2 * 4/2019 Maynard ................ A61K 47/34
2007/0059828 A1 3/2007 Yamaoka et al.
(Continued)

FOREIGN PATENT DOCUMENTS

EP 0668294 8/1995
WO 2013112897 8/2013

OTHER PUBLICATIONS

Markovsky, E.; Baabur-Cohen, H.; Eldar-Boock, A.; Omer, L.; Tiram, G.; Ferber, S.; Ofek, P.; Polyak, D.; Scomparin, A.; Satchi-Fainaro, R. Journal of Controlled Release 2012, 161, 446.
(Continued)

Primary Examiner — Kregg T Brooks
(74) Attorney, Agent, or Firm — Quarles & Brady LLP

(57) ABSTRACT

Structures and methods of making biodegradable trehalose co-polymers are disclosed. Specifically, biodegradable trehalose co-polymers consist of the general structure $R_5$—$[R_1R_2C$—$CR_3R_4]n$-$[DG]_m$-$R_6$, wherein $R_1$-$R_4$ are independently selected from hydrogen or a side chain comprising at least one carbon atom, and wherein at least one of $R_1$-$R_4$ is a side chain comprising -L-trehalose, wherein L is a linker molecule that links trehalose to the monomer through at least one of the trehalose hydroxyl groups (—OH), wherein DG is a biodegradable group, and wherein $R_5$ and $R_6$ are end groups.

5 Claims, 36 Drawing Sheets

(51) Int. Cl.

| | |
|---|---|
| C12P 19/12 | (2006.01) |
| C08B 37/00 | (2006.01) |
| A61K 47/34 | (2017.01) |
| C08G 63/685 | (2006.01) |
| C08G 63/688 | (2006.01) |
| A61K 47/24 | (2006.01) |
| C08F 220/40 | (2006.01) |
| A61K 47/59 | (2017.01) |
| A61K 47/58 | (2017.01) |
| C07H 3/04 | (2006.01) |
| C08G 63/78 | (2006.01) |
| C08G 63/08 | (2006.01) |
| A61K 47/30 | (2006.01) |
| A61K 38/00 | (2006.01) |
| C08F 220/28 | (2006.01) |

(52) U.S. Cl.
CPC .............. *A61K 47/30* (2013.01); *A61K 47/34* (2013.01); *A61K 47/58* (2017.08); *A61K 47/593* (2017.08); *C07H 3/04* (2013.01); *C08B 37/0006* (2013.01); *C08F 220/40* (2013.01); *C08G 63/08* (2013.01); *C08G 63/688* (2013.01); *C08G 63/6852* (2013.01); *C08G 63/6882* (2013.01); *C08G 63/78* (2013.01); *C08G 63/91* (2013.01); *C12P 19/12* (2013.01); *A61K 38/00* (2013.01); *C08F 220/285* (2020.02); *C08F 2438/03* (2013.01); *C08G 2230/00* (2013.01)

(58) Field of Classification Search
CPC ....... C08G 63/912; C08G 63/06; C12P 19/12; C07H 3/04; A61K 47/58; A61K 47/593; A61K 47/193; A61K 47/24; A61K 38/00; A61K 38/193
See application file for complete search history.

(56) References Cited

U.S. PATENT DOCUMENTS

| | | | |
|---|---|---|---|
| 2009/0124534 A1 | 5/2009 | Reineke et al. | |
| 2012/0142649 A1 | 6/2012 | Gray et al. | |
| 2014/0017676 A1 | 1/2014 | Morhet et al. | |
| 2014/0113879 A1 | 4/2014 | Carie et al. | |

OTHER PUBLICATIONS

Yoshiko Miura et al: "Chemoenzymatic synthesis of glycoconjugate polymers starting from non-reducing disaccharides," Journal of Polymer Science Part A: Polymer Chemistry, vol. 42, No. 18, Jan. 1, 2004 (Jan. 1, 2004), pp. 4598-4606.
Nguyen, T. H.; Kim, S.-H.; Decker, C. G.; Wong, D. Y.; Loo, J. A.; Maynard, H. D. Nat. Chem. 2013, 5, 221.
Paz-Alfaro, K. J.; Ruiz-Granados, Y. G.; Uribe-Carvajal, S.; Sampedro, J. G. Journal of Biotechnology 2009, 141, 130.
Parrish, B.; Quansah, J. K.; Emrick, T. Journal of Polymer Science Part A: Polymer Chemistry 2002, 40, 1983.
Parrish, B.; Breitenkamp, R. B.; Emrick, T. Journal of the American Chemical Society 2005, 127, 7404.
Pelegri-O'Day, E. M.; Lin, E.-W.; Maynard, H. D. J. Am. Chem. Soc. 2014, 136, 14323.
Pfister, D.; Morbidelli, M. J. Controlled Release 2014, 180, 134.
Pratt, R. C.; Lohmeijer, B. G. G.; Long, D. A.; Waymouth, R. M.; Hedrick, J. L. Journal of the American Chemical Society 2006, 128, 4556.
Riachi, C.; Schüwer, N.; Klok, H.-A. Macromolecules 2009, 42, 8076.
Roberts, M. J.; Milton Harris, J. Journal of Pharmaceutical Sciences 1998, 87, 1440.
Roberts, M. J.; Bentley, M. D.; Harris, J. M. Advanced Drug Delivery Reviews 2002, 54, 459.
Roy, I. and Jain, N.K. Protein Science, 2009, 24-36.
Siegwart, D. J.; Bencherif, S.A.; Srinivasan, A.; Hollinger, J.O.; Matyjaszewski, K. J. Biomed. Mater. 2008, 87, 345-58.
Silvers, A. L.; Chang, C.-C.; Emrick, T. J Polym Sci Pol Chem 2012, 50, 3517.
Sizovs, A.; Xue, L.; Tolstyka, Z. P.; Ingle, N. P.; Wu, Y.; Cortez, M.; Reineke, T. M. Journal of the American Chemical Society 2013, 135, 15417.
Slavin, S.; Burns, J.; Haddleton, D. M.; Becer, C. R. European Polymer Journal 2011, 47, 435.
Stidham, S. E.; Chin, S. L.; Dane, E. L.; Grinstaff, M. W. Journal of the American Chemical Society 2014, 136, 9544.
Takasu, A.; Houjyou, T.; Inai, Y.; Hirabayashi, T. Biomacromolecules 2002, 3, 775.
Veronese, F. M.; Largajolli, R.; Boccú, E.; Benassi, C. A.; Schiavon, O. Appl Biochem Biotechnol 1985, 11, 141.
Wada, M.; Miyazawa, Y.; Miura, Y. Polymer Chemistry 2011, 2, 1822.
Wang, R.; Chen, W.; Meng, F.; Cheng, R.; Deng, C.; Feijen, J.; Zhong, Z. Macromolecules 2011, 44, 6009.
Woghiren, C.; Sharma, B.; Stein, S. Bioconjugate Chemistry 1993, 4, 314.
Xiao, N.; Liang, H.; Lu, J. Soft Matter 2011, 7, 10834.
Xiao, NY et al. "Preparations of Well-Defined and Degradable Aldehyde-Functionalized Glycopolymeric Nanospheres" Acta Polymerica Sinica, vol. 8, 2012, pp. 818-824; English translation of abstract only.
Xu, N.; Wang, R.; Du, F.-S.; Li, Z.-C. J Polym Sci Pol Chem 2009, 47, 3583.
Yan-Ling, L.; Yun-Fei, N.; Feng, X.; Ya-Shao, C.; Pei, Z. Journal of Biomaterials Science—Polymer Edition 2010, 21, 1143.
Yurkovetskiy, A.; Choi, S.; Hiller, A.; Yin, M.; McCusker, C.; Syed, S.; Fischman, A. J.; Papisov, M. I. Biomacromolecules 2005, 6, 2648.
Zalipsky, S.; Menon-Rudolph, S. In Poly(ethylene glycol); American Chemical Society: 1997; vol. 680, p. 318. (Book Chapter).
Zhang R.; Jain S.; Rowland, M.; Hussain, N.; Agarwal, M.; Gregoriadis, G. Journal of Diabetes Science and Technology 2010, 4, 532.
Abuchowski, A.; Kazo, G. M.; Verhoest Jr, C. R.; Van Es, T.; Kafkewitz, D.; Nucci, M. L.; Viau, A. T.; Davis, F. F. Cancer Biochemistry Biophysics 1984, 7, 175.
Alconcel, S. N. S.; Baas, A. S.; Maynard, H. D. Polymer Chemistry 2011, 2, 1442.
Agarwal, S. Polym. Chem. 2010, 1, 953-964.
Bailey, W. J.; Wu, S. R.; Ni, Z. Makromolekulare Chemie—Macromolecular Chemistry and Physics 1982, 183, 1913.
Bailey, W. J.; Ni, Z.; Wu, S. R. Macromolecules 1982, 15, 711.
Bat, E.; Lee, J.; Lau, U. Y.; Maynard, H. D. Nature Communications 2015, 6.
Bentley, M. D.; Roberts, M. J.; Harris, J. M. J. Pharm. Sci. 1998, 87, 1446.
Besheer, A.; Liebner, R.; Meyer, M.; Winter, G. In Tailored Polymer Architectures for Pharmaceutical and Biomedical Applications; Scholz, C., Kressler, J., Eds.; Amer Chemical Soc: Washington, 2013; vol. 1135, p. 215. (Book chapter).
Campos, L. M.; Killops, K. L.; Sakai, R.; Paulusse, J. M. J.; Damiron, D.; Drockenmuller, E.; Messmore, B. W.; Hawker, C. J. Macromolecules 2008, 41, 7063.
Cerritelli, S.; Velluto, D.; Hubbell, J. A. Biomacromolecules 2007, 8, 1966.
Chi, E. Y.; Krishnan, S.; Randolph, T. W.; Carpenter, J. F. Pharm. Res. 2003, 20, 1325.
Congdon, T.; Notman, R.; Gibson, M. I. Biomacromolecules 2013, 14, 1578.
Congdon, T.; Wilmet, C.; Williams, R.; Polt, J.; Lilliman, M.; Gibson, M. I. European Polymer Journal 2015, 62, 352.
Decker, C. G.; Maynard, H. D. European Polymer Journal 2015, 65, 305.
Delplace, V.; Tardy, A.; Harrisson, S.; Mura, S.; Gigmes, D.; Guillaneuf, Y.; Nicolas, J. Biomacromolecules 2013, 14, 3769.

(56) References Cited

OTHER PUBLICATIONS

Dingels, C.; Muller, S. S.; Steinbach, T.; Tonhauser, C.; Frey, H. Biomacromolecules 2013, 14, 448.
Duro-Castano, A.; Conejos-Sánchez, I.; Vicent, M. Polymers 2014, 6, 515.
Ende, A. E. v. d.; Kravitz, E. J.; Harth, E. Journal of the American Chemical Society 2008, 130, 8706.
Gaertner, H. F.; Offord, R. E. Bioconjugate Chemistry 1996, 7, 38.
Gao, W.; Liu, W.; Christensen, T.; Zalutsky, M. R.; Chilkoti, A. Proceedings of the National Academy of Sciences 2010, 107, 16432.
Garman, A. J.; Barret Kalindjian, S. FEBS Letters 1987, 223, 361.
Gestwicki, J. E.; Cairo, C. W.; Strong, L. E.; Oetjen, K. A.; Kiessling, L. L. J. Am. Chem. Soc. 2002, 124, 14922.
Grover, G. N.; Maynard, H. D. Current Opinion in Chemical Biology 2010, 14, 818.
D'Ayala, G G.; Malinconico, M.; Laurienzo, P.; Tardy, A.; Guillaneuf, Y.; Lansalot, M.; D'Agosto, F.; Charleux, B. J. Polym. Sci., A, Polym. Chem. 2014, 52, 104-111.
Hardwicke, J.; Ferguson, E. L.; Moseley, R.; Stephens, P.; Thomas, D. W.; Duncan, R. Journal of Controlled Release 2008, 130, 275.
Hardwicke, J.; Moseley, R.; Stephens, P.; Harding, K.; Duncan, R.; Thomas, D. W. Mol. Pharmaceutics 2010, 7, 699.
Hardwicke, J. T.; Hart, J.; Bell, A.; Duncan, R.; Thomas, D. W.; Moseley, R. J. Controlled Release 2011, 152, 411.
Hedir, G. G.; Bell, C. A.; Ieong, N. S.; Chapman, E.; Collins, I. R.; O'Reilly, R. K.; Dove, A. P. Macromolecules 2014.
Hey, T.; Knoller, H.; Vorstheim, P. "Half-Life Extension through HESylatoin," In Therapeutic Proteins; Wiley-VCH Verlag GmbH & Co. KGaA: 2012, p. 117-140. (Book Chapter).
Hinou, H et al. "Systematic Syntheses and Inhibitory Activities of Bisubstrate-Type Inhibitors of Sialyltransferases" J. Org. Chem., vol. 68, 2003, pp. 5602-5613.
Hu, J.; Zhao, W.; Gao, Y.; Sun, M.; Wei, Y.; Deng, H.; Gao, W. Biomaterials 2015, 47, 13.
Iha, R. K.; van Horn, B. A.; Wooley, K. L. Journal of Polymer Science Part A: Polymer Chemistry 2010, 48, 3553.
Johnson, D. A. Carbohydr. Res. 1992, 237, 313.
Kanai, M.; Mortell, K. H.; Kiessling, L. L. J. Am. Chem. Soc. 1997, 119, 9931.
Keefe, A. J.; Jiang, S. Nat. Chem. 2012, 4, 59.
Knop, K.; Hoogenboom, R.; Fischer, D.; Schubert, U. S. Angew. Chem. Int. Ed. 2010, 49, 6288.
Kobben, S.; Ethirajan, A.; Junkers, T. Journal of Polymer Science Part A: Polymer Chemistry 2014, 52, 1633-1641.
Kozlowski, A.; Milton Harris, J. Journal of Controlled Release 2001, 72, 217.
Ladmiral, V.; Mantovani, G.; Clarkson, G. J.; Cauet, S.; Irwin, J. L.; Haddleton, D. M. J Am Chem Soc 2006, 128, 4823.
Leader, B.; Baca, Q. J.; Golan, D. E. Nat. Rev. Drug Discovery 2008, 7, 39.
Lee, J.; Lin, E.-W.; Lau, U.Y.; Hedrick, J.L.; Bat, E.; Maynard, H.D. Biomacromolecules, 2013, 14, 2561-2569.
Lee, J.; Ko, J. H.; Lin, E.-W.; Wallace, P.; Ruch, F.; Maynard, H. D. Polym. Chem. 2015, 6, 3443.
Li, L.; Xu, Y.; Milligan, I.; Fu, L.; Franckowiak, E. A.; Du, W. Angewandte Chemie—International Edition 2013, 52, 13699.
Li, F.; Pei, D. F.; Huang, Q. R.; Shi, T. F.; Zhang, G. Carbohyd Polym 2014, 99, 728.
Li, L.; Wang, J.; Obrinske, M.; Milligan, I.; O'Hara, K.; Bitterman, L.; Du, W. Chemical Communications 2015, 51, 6972.
Liu, Z.; Dong, C.; Wang, X.; Wang, H.; Li, W.; Tan, J.; Chang, J. ACS Applied Materials & Interfaces 2014, 6(4), 2393.
Lohmeijer, B. G. G.; Pratt, R. C.; Leibfarth, F.; Logan, J. W.; Long, D. A.; Dove, A. P.; Nederberg, F.; Choi, J.; Wade, C.; Waymouth, R. M.; Hedrick, J. L. Macromolecules 2006, 39, 8574.
Lundberg, P.; Lee, B. F.; van den Berg, S. A.; Pressly, E. D.; Lee, A.; Hawker, C. J.; Lynd, N. A. ACS Macro Lett. 2012, 1, 1240.
Lutz, J.-F.; Andrieu, J.; Üzgün, S.; Rudolph, C.; Agarwal, S. Macromolecules 2007, 40, 8540.
Mancini, R.J.; Lee, J.; Maynard, H.D. J. Am. Chem. Soc., 2012, 134, 8474-8479.

* cited by examiner

Scheme 4

Scheme 11

BIODEGRADABLE TREHALOSE GLYCOPOLYMERS

CROSS-REFERENCE TO RELATED APPLICATIONS

This application represents the national stage entry of PCT international Application PCT/US2015/044973 filed Aug. 13, 2015 and claims priority U.S. Provisional Patent Application 62/036,973 filed Aug. 13, 2014. The contents of this application are hereby incorporated by reference as if set forth in their entirety.

STATEMENT REGARDING FEDERALLY SPONSORED RESEARCH OR DEVELOPMENT

This invention was made with Government support under 1112550, awarded by the National Science Foundation. The Government has certain rights in the invention.

FIELD OF THE INVENTION

Compositions and methods for biodegradable trehalose glycopolymers are disclosed. Specifically, the compositions include novel trehalose-based copolymers having biodegradable bonds, wherein the copolymers can be degraded into non-cytotoxic products.

BACKGROUND OF THE INVENTION

Since Adagen was approved by the Food and Drug Administration (FDA) as the first protein-polymer conjugate in 1990, the field of protein-polymer conjugates has grown tremendously. Currently, these biological therapeutics have grown to a market of over $7.4 billion in 2011 (Evaluate Ltd. Drug sales database; www.evaluategroup.com). Protein conjugates have diverse therapeutic applications ranging from enzyme replacement therapy to novel functions such as neutralization of over-active cytokines or receptors (Alconcel et al., 2011). As a result, the treatment duration of a protein conjugate also ranges significantly. Some treatments are temporary, but protein-polymer conjugates are also used in enzyme replacement therapy, requiring injections over an extended period to treat chronic diseases such as severe combined immunodeficiency (SCID) or gout (Alconcel et al., 2011).

While protein-polymer conjugates offer unique solutions to problems of missing or malfunctioning enzymes, their chronic use presents long-term challenges in vivo. Currently, all ten Food and Drug Administration (FDA)-approved therapeutic protein conjugates use poly(ethylene glycol) (PEG) (Pfister and Morbidelli, 2014; Besheer et al., 2013; Pelegri-ODay et al., 2014). PEG is widely used in many disciplines, yet some deficiencies in its therapeutic application have been observed. These include non-biodegradability causing accumulation in tissue and immunological responses such as accelerated blood clearance upon multiple doses (Besheer et al., 2013; Chi et al., 2003).

Polymer conjugation also typically results in a decrease in bioactivity of the conjugate due to steric shielding of the protein active site. In addition, protein therapeutics often must be formulated with excipients for additional stabilization since proteins are highly susceptible to losses in activity when exposed to temperature fluctuations and other stressors ("FDA Access Data", www.accessdata.fda.gov). While PEGylation often increases stability against environmental stressors, all of protein-PEG conjugates still need to be refrigerated and contain excipients as stabilizers (Leader et al., 2008; Keefe and Jiang, 2012; Nguyen et al., 2013).

PEG alternatives have been developed which improve upon these drawbacks. For instance, previous work in the Maynard group has shown that polymers containing pendant trehalose units stabilize proteins against heat, lyophilization, and electron irradiation (Mancini et al., 2012; Lee et al., 2013; Bat et al., 2015; Lee et al., 2015). Trehalose is a widely used excipient used in the food and cosmetic industries and has been shown to be important in protecting animals and plants against dehydration stress (Jain and Roy, 2009). Other polymers have been shown to exhibit protein-stabilizing properties, including charged polymers, polyols, and other saccharide-based materials (Keefe and Jiang, 2012; Nguyen et al., 2013; Congdon et al., 2013; Stidham et al., 2014; Hu et al., 2015). All these polymers are being actively investigated as PEG alternatives, which also offer stabilization against environmental stressors. However, these examples are still not biodegradable.

Degradable polymers are important to avoid build-up of polymer within the body, especially for enzyme replacement and other chronic therapies. Degradable polysaccharide conjugates have also been prepared by conjugating proteins to biopolymers such as hydroxyethyl starch (HES)(Hey et al., 2012), polysialic acid (Zhang et al., 2010), and dextrin (Hardwicke et al., 2010; Hardwicke et al., 2011). The synthesis of a degradable protein-polymer conjugate by controlled radical polymerization (CRP) has also recently been reported (Decker and Maynard, 2015). Many of these conjugates display increased in vivo half-lives. However, many of these polymers are heterogeneous, which might make FDA approval more difficult, and do not necessarily stabilize proteins.

We sought to prepare well defined polyester backbone and trehalose side chain polymers so that the polymers would stabilize proteins and biodegrade. Previous examples of well-defined biodegradable glycopolymers (none have been reported with trehalose) containing either esters or amides in the main chain backbone were polymerized in two ways: by polymerization of sugar-functionalized monomers, or by post-polymerization modification of polymers containing reactive handles (Xu et al., 2009; Slavin et al., 2011). However, typical polyester or polyamide syntheses require anhydrous conditions, which is compatible with the low solubility of trehalose in typical organic solvents. Therefore, polyesters containing reactive handles were first synthesized, which could be later functionalized with trehalose units after polymerization and purification. While a variety of high-yielding "click" reactions have been demonstrated for the synthesis of glycopolymers, the thiol-ene reaction yields a stable thioether, which can be formed in high yields (Campos et al., 2008).

Polymers may be used as additives to prevent mis-folding and denaturation of proteins. However, the use and development of polymers as food additives and drug component presents its own problems, as polymer longevity causes down-chain problems in waste management and disposal. Due to the wide applicability of polymers in both medical and non medical fields, interest in developing biodegradable polymers has greatly increased (Agarwal, S. *Polym. Chem.* 2010, 1, 953-964), Moving towards synthesis of easily degradable, "green" polymers will be increasingly important as polymers continue to be used worldwide.

Trehalose is a non-reducing disaccharide formed by α,α-1,1-linked glucose units, which has been proven to exhibit protection against temperature changes and dehydration$^2$ and is widely used in the food and cosmetic industries.

Applicants' previous work has shown that glycopolymers with pendant trehalose groups offer superior protection to both heat burden and lyophilization, better than free (non-polymeric) trehalose and poly(ethylene glycol) (PEG) (Mancini et al., 2012; Lee et al., 2013). These polymers are promising for a variety of applications, but Applicants herein develop techniques to make the polymers degradable.

Needed in the art are biodegradable polymers that stabilize proteins and biodegrade and that can be readily synthesized with reasonable production. Needed in the art are degradable trehalose glycopolymers that stabilize proteins and other biomolecules (e.g., to the lyophilization process and to heat burden) and also can be degraded through simple processes such as ester hydrolysis.

SUMMARY OF THE INVENTION

In one aspect, the present invention relates to a biodegradable trehalose co-polymer. The co-polymer consists of the general structure:

wherein $R_1$-$R_4$ are independently selected from hydrogen or a side chain comprising at least one carbon atom, and wherein at least one of $R_1$-$R_4$ is a side chain comprising -L-trehalose, wherein L is a linker molecule that links trehalose to the monomer through at least one of the trehalose hydroxyl groups (—OH), wherein DG is a biodegradable group, and wherein $R_5$ and $R_6$ are end groups.

In one embodiment, $R_5$ and $R_6$ are independently selected from the group consisting of -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, and biomolecules.

In one embodiment, $R_5$ and $R_6$ are independently selected from the group consisting of -Alkyl, -Alkenyl, -Alkynyl, -aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), and biomolecules.

In one embodiment, DG comprises at least one ester group.

In one embodiment, the ester group is in the backbone of the co-polymer.

In one embodiment, the ester group is produced from a cyclic ketene acetal through ring-opening polymerization.

In one embodiment, the cyclic ketene acetal has the structure of

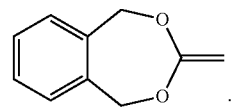

In one embodiment, the degradation products of the co-polymer are non-cytotoxic, and the degradation products of the co-polymer do not disrupt cell proliferation.

In one embodiment, the co-polymer has a structure of

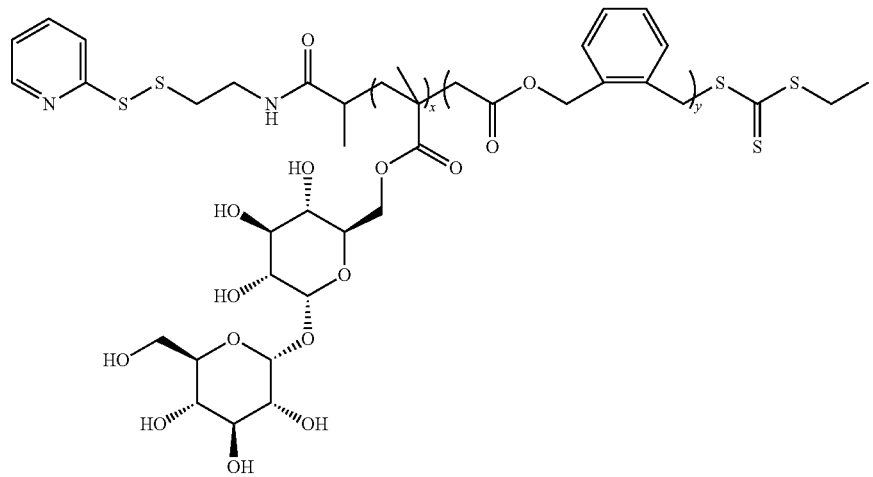

In one embodiment, the co-polymer is degradable under basic conditions or by hydrolysis in vitro or in vivo.

In one embodiment, the co-polymer has a structure of

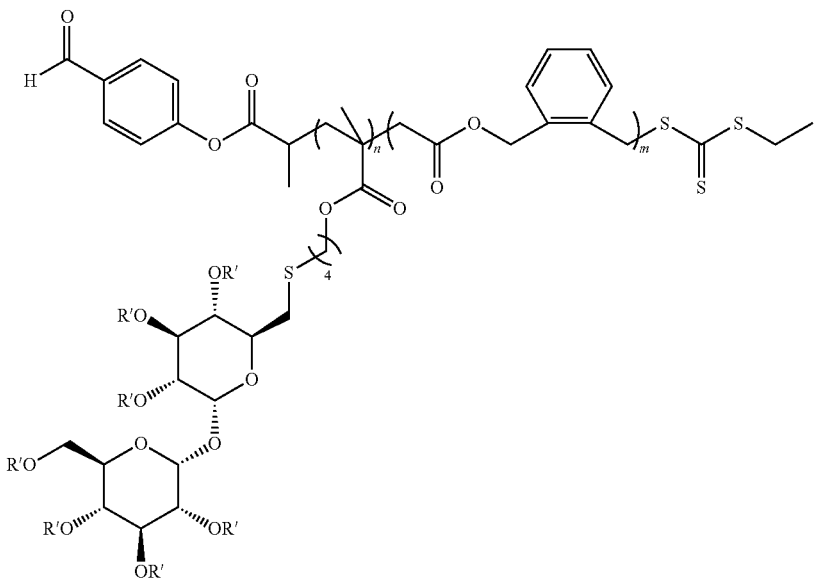

In one aspect, the present invention discloses a biodegradable trehalose co-polymer, wherein the polymer consists of the general structure:

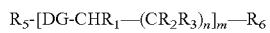

wherein $R_1$-$R_3$ are independently selected from hydrogen or a side chain comprising at least one carbon atom, and wherein at least one of $R_1$-$R_3$ is a side chain comprising -L-trehalose, wherein L is a linker molecule that links trehalose to the co polymer through at least one of the trehalose hydroxyl groups (—OH), wherein DG is a biodegradable group, and wherein $R_5$ and $R_6$ are end groups, and wherein n=0-10, wherein m≥1.

In one embodiment, $R_5$ and $R_6$ are independently selected from the group consisting of -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylanines), hydrazines, and biomolecules.

In one embodiment, $R_5$ and $R_6$ are independently selected from the group consisting of -Alkyl, -Alkenyl, -Alkynyl, -aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), and biomolecules.

In one embodiment, DG comprises at least one ester group.

In one embodiment, the ester group is in the backbone of the polymer.

In one aspect, the present invention discloses a method of synthesizing a biodegradable trehalose co-polymer for stabilizing a biomolecule, the method comprising the steps of: (a) incorporating a side chain comprising a trehalose molecule into a polymerizable monomer; and (b) co-polymerizing the resulting monomer with a cyclic ketene acetal to obtain a co-polymer according to claim 1.

In one embodiment, the co-polymer is generated through chemical synthesis.

In one embodiment, the polymerizable monomer is selected from the group consisting of a styrene monomer, an acrylate monomer, a methacrylate monomer, an acrylamide monomer, a methacryl amide monomer, a vinyl monomer, a norborenyl monomer, and a strained cycle alkene monomer.

In one embodiment, the cyclic ketene acetal has the structure of

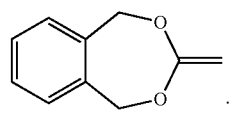

In one embodiment, the step of co-polymerizing the resulting monomer to obtain a homopolymer or copolymer is performed by any one of, but not limited to the following techniques; reversible addition-fragmentation chain transfer (RAFT) polymerization, atom transfer radical polymerization (ATRP), nitroxide mediated polymerization (NMP), cyanoxyl-mediated free radical polymerization, conventional radical polymerization, or ring opening polymerization (ROP).

In one embodiment, the step of co-polymerizing the resulting monomer to obtain a homopolymer or co-polymer is performed by reversible addition-fragmentation chain transfer (RAFT) polymerization.

In one embodiment, one or more of the hydroxyl groups of the trehalose are protected by the formation of an acetal or an ether.

In one aspect, the present invention discloses a method of synthesizing a biodegradable trehalose polymer for stabilizing a biomolecule. The method comprises the steps of: a) polymerizing a cyclic ester with an alcohol with to form a polymer, where in the cyclic ester includes a pendant functional group; b) preparing a thiolated trehalose monomer; c) reacting the polymer with the thiolated trehalose monomer to form the biodegradable trehalose polymer.

In one embodiment, the cyclic ester is an allyl-functionalized caprolactone (aCL).

In one embodiment, the alcohol is a primary alcohol as an initiator.

In one embodiment, the reaction in step a) is a ROP.

In one embodiment, the reaction in step a) further needs a catalyst.

In one embodiment, the catalyst is triazabicyclodecane (TBD).

In one embodiment, the thiolated trehalose monomer has the structure of:

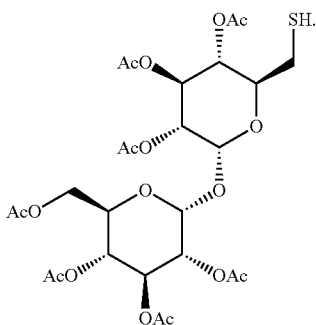 [SMILES: CC(=O)OC[C@H]1O[C@H](O[C@H]2O[C@H](CS)[C@@H](OC(C)=O)[C@H](OC(C)=O)[C@H]2OC(C)=O)[C@H](OC(C)=O)[C@@H](OC(C)=O)[C@@H]1OC(C)=O]

DETAILED DESCRIPTION OF THE INVENTION

In General

Figure 1:
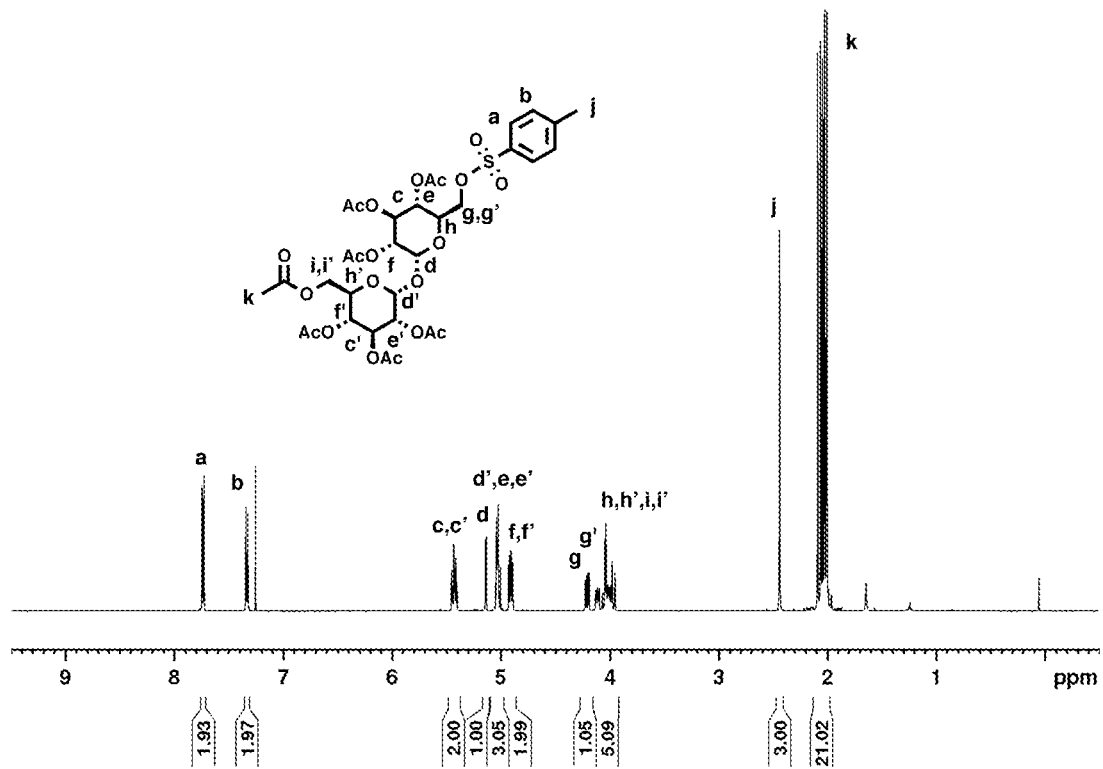
FIG. 1 is a graph showing $^1$H-NMR (500 MHz, CDCl$_3$) of tosylated trehalose 4.

Before the present materials and methods are described, it is understood that this invention is not limited to the particular methodology, protocols, materials, and reagents described, as these may vary. It is also to be understood that the terminology used herein is for the purpose of describing particular embodiments only and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Definitions

Before the composition and related methods are described, it is to be understood that this invention is not limited to the particular methodology, protocols, materials, and reagents described, as these may vary. The terminology used herein is for the purpose of describing particular embodiments only, and is not intended to limit the scope of the present invention which will be limited only by any later-filed non-provisional applications.

The invention described herein provides compositions and methods for biodegradable trehalose glycopolymers, that have biodegradable bonds. The invention also provides a means for stabilizing biomolecules by protecting or maintaining the structure using effective amounts biodegradable trehalose glycopolymers added or conjugated to the biomolecules.

According to one embodiment of the invention, the as-disclosed trehalose-based copolymers show both biodegradability and stabilization abilities. Biodegradable trehalose-based homopolymer or copolymers are used to stabilize protein molecules against aggregation, conformational changes and/or degradation, such as denaturation of native protein, helping to maintain the protein in the desired configuration in a hostile or stressful environment, and intended function is maintained to be at least equal to the protein in its natural states or is enhanced over a reduced activity that the protein would have in the stressful environment. While proteins can be stabilized against degradation, e.g. by heat, electromagnetic radiation, shear stress, proteolysis, or by chemical modification such as reduction, oxidation, or carbamylation, biodegradable trehalose-based homopolymer or copolymers are degradable under certain conditions and degradation products are non-cytotoxic and do not disrupt cell proliferation.

In some embodiments, biodegradable trehalose-based homopolymers or copolymers may be completely degraded after 24 hours under a base condition (e.g., 5% KOH). In one embodiment, biodegradable trehalose-based homopolymers or copolymers may be degraded slowly in aqueous solution by ester hydrolysis in aqueous solution. The hydrolysis can be accelerated to study the degradation by subjecting to 24 hours under a base condition.

One method for producing biodegradable trehalose-based co-polymers may include a step of cyclic ketene acetals undergoing ring-opening polymerization to produce an ester in the growing polymer backbone. The method may also include a step of co-polymerization of cyclic ketene acetals with one trehalose-based monomer by using ATRP, RAFT, or NMP.

Another method for producing biodegradable trehalose-based co-polymers may include a step of co-polymerization of cyclic ketene acetals with another monomer to produce biodegradable backbone copolymers with active sites. The method may also include a step of attaching trehaloses to the biodegradable backbone co-polymers at the active sites.

One method for producing biodegradable trehalose-based polymers may include the step of polymerizing a cyclic ester with an alcohol with to form a polymer, where in the cyclic ester includes a pendant functional group. The method may also include a step of reacting the polymer with the thiolated trehalose monomer to form the biodegradable trehalose polymer.

The term "aryl" refers to a carbocyclic (non-heterocyclic or heterocyclic) aromatic ring or mono-, bi- or tri-cyclic ring system. The aromatic ring or ring system is generally composed of 6 to 10 carbon atoms. Examples of aryl groups include but are not limited to phenyl, biphenyl, naphthyl and tetrahydronaphthyl. 6-membered aryls such as phenyl are preferred.

The term "alkyl" refers to optionally substituted straight chain or branched chain hydrocarbon groups. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "alkyl" also encompasses alkyl groups containing one less hydrogen atom such that the group is attached via two positions, i.e., divalent. "$C_{1-4}$alkyl" and "$C_{1-3}$alkyl" including methyl, ethyl, propyl, isopropyl, n-butyl, iso-butyl, sec-butyl and tert-butyl are preferred with methyl being particularly preferred.

The term "biodegradable," as used herein, refers to the capability of being broken down into innocuous products in the normal functioning of the human body, tissues and cells and living organisms (e.g., bacteria).

The term "biodegradable bonds," as used herein, refer to chemical bonds that are dissociable or broken under biological conditions of the normal functioning of the human body, tissues and cells and living organisms. In one embodiment, the present invention discloses polymers that comprise at least one biodegradable bond, e.g., ester, amide, disulfide, or phosphate linkages bond. In one embodiment, the present copolymers may include at least one biodegradable bond on the backbone of the copolymers.

The term "biodegradable polymers," as used herein refer to a specific type of polymer that breaks down after its intended purpose to result in natural byproducts such as gases ($CO_2$, $N_2$), water, other small molecule organic or inorganic byproducts, biomass, and inorganic salts. In one embodiment, the biodegradable polymers are synthetically made, and largely consist of ester, amide, disulfide, acetal, imine, oxime, Diels-Alder adduct, orthoester, hydrazone, cis-aconitryl, carbonate, carbamate, carbami de, glycosidic saccharide linkages, anhydride, phosphoester, phosphoanhydride, iminocarbonate, cyanoacrylate, phosphazene, phosphoramidate, amide-enamine, urea, urethane or any functional group which can degrade in a Natural system. The biodegradable polymers may often be synthesized by condensation reactions, ring opening polymerization, and metal catalysts. In one embodiment, the biodegradable polymers of the present invention include trehaloses that can stabilize proteins or any other biomolecules. In one embodiment, biodegradable polymers (e.g., caprolactone polymers) may be produced by using a ring opening reaction. In one embodiment, biodegradable polymers (e.g., BMDO polymers) may be produced by using radical polymerizations.

The term "pendant functional group," as used herein refers to a functional group that is a pendant branch from the backbone of a co-polymer. In one embodiment, the pendant functional group provides a location where additional functional groups, e.g., trehalose, can be attached to the backbone of co-polymers.

The term "stressful environment," as used herein, means an environment which will reduce a functional property or activity of a biomolecule. For example, the environment may reduce a functional property or activity of a protein over a native protein or that which the protein has in its natural state. A stressful environment may include temperatures which create adverse thermal environments which could be elevated or reduced temperatures, solvents such as an organic solvent, the presence of proteases, pH and/or lack of buffer.

The term "biomolecule" as used herein refers, but is not limited to proteins, enzymes, antibodies, DNA, siRNA, and pharmaceutical compositions. Such biomolecules are subject to environmental stresses which include but are not limited to heat, desiccation, light, storage, exposure to enzymes, endo- and exo-nucleases and pH variation.

The term "protein" used herein refers to any compound of two or more individual amino acids (whether or not naturally occurring) linked via peptide bonds, as occur when the carboxyl carbon atom of the carboxylic acid group bonded to the α-carbon of one amino acid (or amino acid residue) becomes covalently bound to the amino nitrogen atom of the amino group bonded to the α-carbon of an adjacent amino acid. These peptide bond linkages, and the atoms comprising them (i.e., α-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide." Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. As may be appreciated, a "fragment" of a protein may be a form of the protein truncated at the amino terminus, the carboxyl terminus, and/or internally (such as by natural splicing), and may also be variant and/or derivative. A "domain" of a protein is also a fragment, and comprises the amino acid residues of the protein required to confer biochemical activity corresponding to naturally occurring protein. The term "protein" used herein also include "protein conjugate" which refers to a compound complex comprising a "protein" which is interlinked to one another molecule or subject. The term "complex" is used herein to mean those compounds comprising at least two components. The protein may be naturally occurring and isolated from its source. The protein may be produced using DNA recombination or mutation techniques. The protein may be produced in vivo in a whole animal, or in a eukaryotic or prokaryotic cell; alternatively, the protein may be generated using an in vitro method such as cell-free in vitro translation, e.g., using *E. coli* lysate, wheat germ extract, or rabbit reticulocyte. Cell free in vitro translation methods can be employed following in vitro transcription, e.g., following phage or ribosome display.

Examples of proteins include, without limitation, Lysozyme, Adenosine deaminase, L-Asparaginase, Mammalian urate oxidase, Interferons, Anti-TNF α Fab, granulocyte colony stimulated factor (G-CSF), Continuous ervthropoietin receptor activator, hGH antagonist B2036, Insulin, Insulin human inhalation, Insulin aspart, Insulin glulisine, Insulin lispro, Isophane insulin, Insulin detemir, Insulin glargine, Insulin zinc extended, Pramlintide acetate, Growth hormone (GH), Somatotropin, Mecasermin, Mecasermin rinfabate, Factor VIII. Factor IX, Antithrombin III (AT-iii), fibroblast growth factor (FGF), basic fibroblast growth factor (bFGF), vascular endothelial growth factor (VEGF), platelet derived growth factor (PDGF), Protein C concentrate, β-Gluco-cerebrosidase, Alglucosidase-α, Laronidase (α-L-iduronidase), Idursulphase (iduronate-2-sulphatase), Galsulphase, Agalsidase-β (human α-galactosidase A), α-1-Proteinase inhibitor, Lactase, Pancreatic enzymes, lipase, amylase, protease, Adenosine deaminase, Pooled immunoglobulins, Human albumin, Erythropoietin, Epoetin-α, Darbepoetin-α, Sargramostim (granulocytemacrophage colony stimulating factor; GM-CSF), Oprelvekin (interleukin11; IL11) Human follicle-stimulating hormone (FSH), Human chorionic gonadotropin (HCG), Lutropin-α, Type I alpha-interferon, interferon alfacon 1, consensus interferon, Aldesleukin (interleukin 2 (IL2), epidermal thymocyte activating factor (ETAF), Alteolase (tissue plasminogen activator: tPA), Reteplase (deletion mutein of tPA), Tenecteplase, Urokinase, Factor Vila, Drotrecogin-α (activated protein C), Salmon calcitonin, Teriparatide (human parathyroid hormone residues 1-34), Exenatide, Octreotide, Dibotermin-α (recombinant human bone morphogenic protein 2; rhBMP2), Recombinant human bone morphogenic protein 7 (rhBMP7), Histrelin acetate (gonadotropin releasing hormone; GnrH), Palifermin (keratinocyte growth factor; KGF), Becaplermin (platelet-derived growth factor; PDGF), Trypsin, Nesiritide, Botulinum toxin type A, Botulinum toxin type B, Collages, Collagenase, Human deoxyribonuclease I, dornase-α, Hyaluronidase (bovine, ovine), Hyaluronidase (recombinant human), Papain, L-Asparaginase, Rashuricase, Lepirudin, Bivalirudin, Streptokinase, Anistreplase (anisoylated plasminogen streptokinase activator complex; APSAC), Bevacizumab, Cetuximab, Panitumumab, Alemtuzumab, Rituximab, Trastuzumab, Abatacept Anakinra, Adalimumab, Etanercept, Infliximab, Alefacept, Efalizumab, Natalizumab, Eculizumab, Antithymocyte globulin (rabbit), Basiliximab, Daclizumab, Muromonab-CD3, Omalizumab, Palivizumab, Enfuvirtide, Abciximab, Crotalidae polyvalent immune Fab (ovine), Digoxin immune serum Fab (ovine), Ranibizumab, Denileukin diftitox, Ibritumomab tiuxetan, Gemtuzumab ozogamicin, Tositumomab, and itositumomab.

A denatured protein can be fully denatured, or partially denatured or renatured such that the protein is in non-native form as unfolded protein and/or partially folded refolding intermediate(s). An aqueous solution or dried sample comprising denatured protein may contain one or more of these forms. A native protein is in a folded, functional conformation. Some protein may also be present in aqueous solution, or in a dried sample, in the form of contaminating aggregates and/or inclusion bodies.

The term "stability" refers to the maintenance of a protein or other biomolecule's native bioactivity function after storage. The present invention will provide stability of at least 70%, and preferably at least 80%, of the protein's function as compared to storage without a trehalose stabilizing agent under identical environmental conditions. It is envisioned that, for example, when a protein like insulin is conjugated with a trehalose-based polymer or copolymer as described here, the insulin protein retains at least 70%, 75%, 80%, 85%, 90% or greater percentage of its native bioactivity compared to insulin by itself, which may retain only 20% of its original bioactivity at best. Those skilled in the art appreciate that the percent of bioactivity that is retained is protein and stress dependent. Furthermore, the length-of time that a conjugated protein is able to maintain its bioactivity or function compared to a naked/unmodified protein varies depending on the environmental stressors it is subjected to. It is envisioned the conjugated proteins as described here can retain bioactivity for at least 5, 10, 20, 30, 40, 50, 60, 70, 80, 90, or 100 times longer than an unconjugated native protein under identical environmental conditions.

The term "antibody" or "antibody molecule" as used herein refers to immunoglobulin molecules or other molecules which comprise an antigen binding domain. The term "antibody" or "antibody molecule" as used herein is thus intended to include whole antibodies (e.g., IgG, IgA, IgE, IgM, or IgD), monoclonal antibodies, polyclonal antibodies, and chimeric antibodies.

The terms "monoclonal antibody" or "monoclonal antibody composition" as used herein refer to a preparation of antibody molecules of a single amino acid composition. The monoclonal antibody also includes "human monoclonal antibody" which refers to antibodies displaying a single binding specificity which have variable and constant regions derived from human germline immunoglobulin sequences. The human monoclonal antibodies can be produced by a hybridoma which includes a B cell obtained from a transgenic nonhuman animal, for example, a transgenic mouse, having a genome comprising a human heavy chain trans gene and a light human chain transgene fused to an immortalized cell.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies can also comprise a murine variable region and a human constant region. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art.

The term "antibody" also shall include humanized antibody, human antibody and recombinant human antibody. The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." Particularly preferred CDRs correspond to those representing sequences recognizing the antigens noted above for chimeric and bifunctional antibodies.

The term "human antibody" includes antibodies having variable and constant regions derived from human germline immunoglobulin sequences. The variable heavy chain is preferably derived from germline sequence DP-50 and the variable light chain is derived from germline sequence L6. The constant regions of the antibody are constant regions of human IgG 1 type.

The term "recombinant human antibody" includes all human antibodies that are prepared, expressed, created or isolated by recombinant means, such as antibodies isolated from a host cell such as an SP2-0, NSO or CHO cell (like CHO K1) or from an animal (e.g., a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form.

The term "antibody" also includes "antibody fragments" or "antibody-derived fragments" which comprise an antigen binding domain are also included. The term "antibody fragment" as used herein is intended to include any appropriate antibody fragment that displays antigen binding function, for example, Fab, Fab', F(ab')2, scFv, Fv, dsFv, ds-scFv, Fd, dAbs, TandAbs dimers, mini bodies, monobodies, diabodies, and multimers thereof and bispecific antibody fragments. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

The antibodies or antibody fragments can be produced naturally or can be wholly or partially synthetically produced. Thus the antibody may be from any appropriate source, for example recombinant sources and/or produced in transgenic animals or transgenic plants. Thus, the antibody molecules can be produced in vitro or in vivo. Preferably the antibody or antibody fragment comprises an antibody light chain variable region ($V_L$) and an antibody heavy chain variable region ($V_H$) which generally comprise the antigen binding site. The antibody or antibody fragment can comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region. Furthermore, the antibody or antibody fragment can comprise all or a portion of a kappa light chain constant region or a lambda light chain constant region. All or part of such constant regions may be produced naturally or may be wholly or partially synthetic. Appropriate sequences for such constant regions are well known and documented in the art.

The term "fragment" as used herein refers to fragments of biological relevance (functional fragment), e.g., fragments which can contribute to or enable antigen binding, e.g., form part or all of the antigen binding site, or can contribute to the inhibition or reduction in function of the antigen or can contribute to the prevention of the antigen interacting with its natural ligands. Fragments thus comprise a heavy chain variable region ($V_H$ domain) and/or a light chain variable region ($V_L$ domain) of the antibodies of the invention. Fragments may also comprise one or more of the heavy chain complementarity determining regions (CDRs) of the antibodies or of the $V_H$ domains, or one or more of the light chain complementarity determining regions (CDRs) of the antibodies, or of the $V_L$ domains.

The term "sugar polymer" as used herein encompasses polymeric and oligomeric saccharide molecules comprising three or more mono-, di- or tri-saccharide units. The sugar polymer can be a linear or non-linear amphipathic sugar polymer derivative. Specifically, sugar polymers comprise one or more sugar(s) including, without limitation, trehalose, erythrose, threose, ribose, arabinose, xylose, lyxose, allose, altrose, glucose, mannose, gulose, idose, galactose, talose, psicose, fructose, sorbose, tagatose, xylulose and ribulose. The sugar polymers can be a dextran, cellulose, amylose, starch, pullulan, mannan, chitin, chitosan, inulin, levan, xylan, cyclodextrin (provided that it is not an alpha, beta or gamma cyclodextrin), cycloamylose or a derivative thereof.

Sugar polymers, specifically trehalose-based homopolymer or copolymers suitable for use in the invention are those which, at an appropriate concentration and in appropriate conditions, can (1) maintain a native biomolecule in its native state to retain a functional property of the native biomolecule in a stressful environment or (2) maintain a denatured biomolecule in a non-native state as desired by the researcher. Suitable trehalose-based homopolymer or copolymers are those which are capable of shielding hydrophobic amino acid side chains or modifying the net biomolecule charge or hydrogen bonding characteristics. Suitable trehalose-based homopolymer or copolymers may also comprise those capable of water entrapment, or those having hydrogen bonding characteristics.

As used herein, the term "glycopolymer" refers to any polymer that comprises one or more saccharide moieties, for example, a polysaccharide, or a glycosaminoglycan.

The term "trehalose-based monomer," as used herein, refers to a monomer including at least one trehalose which is covalently bound to the side chain of the monomer.

The term "ring-opening polymerization" or "ROP," as used herein, refers to a form of chain-growth polymerization, in which the terminal end of a polymer chain acts as a reactive center where further cyclic monomers can react by opening its ring system and form a longer polymer chain. The propagating center can be radical, anionic or cationic. Some cyclic monomers such as norbornene or cyclooctadiene can be polymerized to high molecular weight polymers by using metal catalysts. ROP continues to be a versatile method of synthesis of major groups of biopolymers, particularly when they are required in quantity. In one embodiment, the the caprolactone polymer in the present invention may be produced by ROP.

The term "physiological conditions," as used herein, refers to conditions of the external or internal milieu that may occur in nature for that organism or cell system, in contrast to artificial laboratory conditions. A temperature range of 20-40 degrees Celsius, atmospheric pressure of 1, pH of 4-8, glucose concentration of 1-20 mM, atmospheric oxygen concentration, and earth gravity are examples of physiological conditions for most earth organisms.

The term "Atom transfer radical polymerization" or "ATRP," as used herein, refers to an example of a reversible-deactivation radical polymerization, wherein a carbon-carbon bond forms through a transition metal catalyst. The atom transfer step is the key step in the reaction responsible for uniform polymer chain growth.

The term "Reversible Addition-Fragmentation chain Transfer" or "RAFT," as used herein, refers to one of several kinds of Reversible-deactivation radical polymerization wherein a chain transfer agent in the form of a thiocarbonylthio compound (or a similar RAFT agent) is used to afford control over the generated molecular weight and polydispersity during a free-radical polymerization.

The term "Nitroxide-mediated radical polymerization" or "NMP," refers to a method of radical polymerization that makes use of an alkoxyamine initiator to generate polymers with well controlled stereochemistry and a very low polydispersity index.

THE INVENTION

In one aspect, the application discloses biodegradable trehalose-based copolymers and methods of making the copolymers.

In one aspect, the present invention discloses degradable trehalose glycopolymers. Preferably, the trehalose glycopolymers are bio-degradable. The trehalose glycopolymers in the present invention may be co-polymers.

In one embodiment, the present trehalose copolymer consists of the general structure of (1):

$$R_5—[R_1R_2C—CR_3R_4]_n-[DG]_m-R_6 \quad (1)$$

wherein $R_1$-$R_4$ are independently selected from hydrogen or a side chain comprising at least one carbon atom, and wherein at least one of $R_1$-$R_4$ is a side chain comprising -L-trehalose, wherein L is a linker molecule that links trehalose to the monomer through at least one of the trehalose —OH groups, wherein DG is a biodegradable functional group, and wherein $R_5$ and $R_6$ are the end groups.

In some embodiments, the end groups of $R_5$ and $R_6$ are independently selected from the group consisting of activated disulfides, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, alkynes, derivatives thereof, and a combination thereof or any end group that can react with a natural or unnatural functional group of a biomolecule.

In one embodiment, $R_5$ and $R_6$ are independently selected from the group consisting of -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, and biomolecules.

In one specific embodiment, $R_5$ and $R_6$ are independently selected from the group consisting of -Alkyl, -Alkenyl, -Alkynyl, -Aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), —H, and biomolecules.

In one embodiment, any of $R_1$-$R_4$ that is not-L-trehalose is either hydrogen or an alkyl group. In one specific embodiment, the alkyl group is preferably a methyl group.

In one embodiment, one of $R_1$-$R_4$ is an alkyl group and two of $R_1$-$R_4$ are hydrogen. In one specific embodiment, the alkyl group is preferably a methyl group.

In one embodiment, the biodegradable functional groups of DG may include ester, amide, or disulfide groups, acetal, imine, oxime, Diels-Alder adduct, orthoester, hydrazone, cis-aconitryl, carbonate, carbamate, carbamide, glycosidic saccharide linkages, anhydride, phosphoester, phosphoanhydride, iminocarbonate, cyanoacrylate, phosphazene, phosphoramidate, amide-enamine, urea, urethane or any group which can degrade in a Natural system or any other group which can degrade in a natural system. In one preferred embodiment, the biodegradable group of DG comprises at least one ester group. More preferably, the ester group is in the backbone of the co-polymers.

In one embodiment, the co-polymers with biodegradable groups of DG on the backbone may be synthesized through a ring-opening polymerization (ROP) reaction of a cyclic ketene acetal with other monomers. The cyclic ketene acetal provides biodegradable groups of DG, i.e., ester into the backbone of the co-polymers.

In one embodiment, cyclic ketene acetals or monomers that can introduce the degradable group into the co-polymers may include 5,6-benzo-2-methylene-1,3-dioxepane 2-methylene-1,3-dioxe-5-pene, 2-ethylidene-4-methyl-1,3-dioxane, 2-ethylidene-4-ethyl-1,3-dioxane, 2-ethylidene-1,3-dioxane, 1-vinyl-4,7-dioxaspiro-[2,4]heptane, 1-vinyl-4,9-dioxaspiro-[2.6]nonane, 1-vinyl-6,7-benzo-4,9-dioxaspiro [2.6]nonane, 9,9-disubstituted-4-methylene-3,5,8,10-tetraoxabicyclo[5.3.0]decane, 3,9-bis-methylene-2,4,8,10-tetraoxa-spiro[5,5]undecane, or 2-methylene-1,3,6-trioxocane.

In one preferred embodiment, the ester group is produced from a cyclic ketene acetal through a ROP reaction. More preferably, the cyclic ketene acetal is BMDO that has the structure of

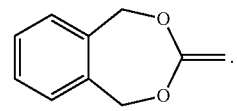

In one embodiment, the copolymers with the general structure of (1) may be produced from a cyclic ketene acetal with another monomer by using any suitable polymerization reactions. In another embodiment, the polymerization reactions may include free radical polymerization, reversible addition-fragmentation (RAFT) polymerization, atom transfer radical polymerization (ATRP), nitroxide mediated polymerization (NMP), cyanoxyl-mediated free radical polymerization, conventional radical polymerization, or ring opening polymerization (ROP). In one embodiment, the present degradable trehalose copolymers are synthesized through a RAFT reaction of a cyclic ketene acetal, e.g., BMDO, with another monomer.

In one embodiment, the other monomer comprises a trehalose. Applicants' previous PCT patent application No. PCT/US2013/023235 discloses many trehalose-based monomers that are suitable for the present invention. Example 2 shows some exemplary monomers and methods of making such monomers.

In one embodiment, the trehalose co-polymers may be degraded under certain physiological conditions. In one embodiment, physiological conditions may include basic conditions or hydrolysis in vitro or in vivo. Applicants envision that other suitable physiological conditions as appreciated by one skilled in the art may also be used for degradation of the trehalose co-polymers. In one preferred embodiment, the degradation products of co-polymers are non-cytotoxic and the products do not disrupt cell proliferation. Scheme 10 in Example 2 shows one exemplary biodegradation of trehalose co-polymers under basic conditions to accelerate the degradation.

In one preferred embodiment, the present trehalose co-polymer has a structure (2) of

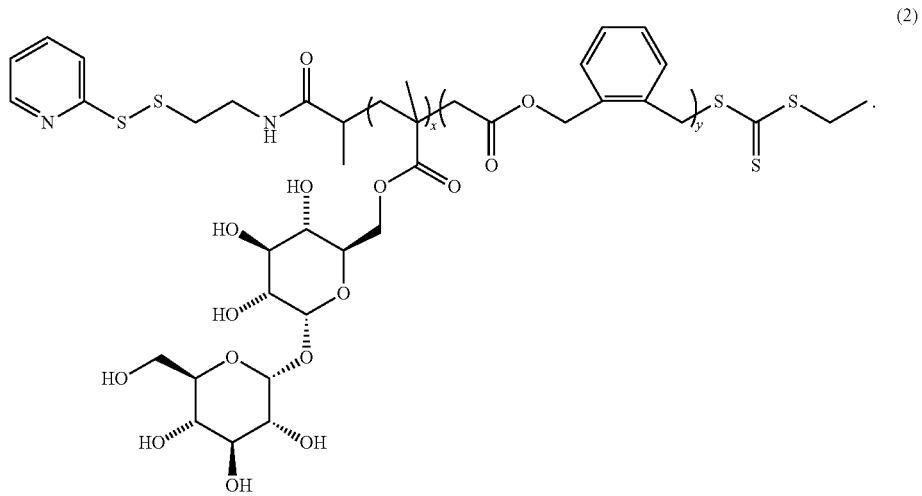

(2)

Example 2 shows a synthetic method of making trehalose co-polymer (2). Scheme 10 shows biodegradation of trehalose co-polymer (2) under basic conditions.

In another preferred embodiment, the present trehalose co-polymer has a structure (3) of:

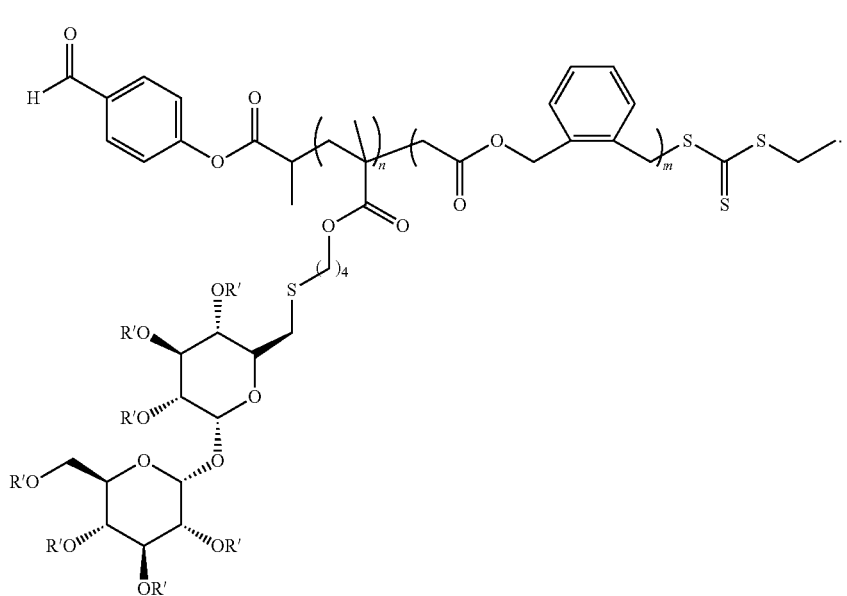

In one embodiment, a biodegradable trehalose polymer consists of the general structure:

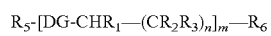

(3)

In one embodiment, the biodegradable trehalose co-polymer may be trehalose-functionalized caprolactones. Poly(caprolactone) is a well-known polymer that is approved by the FDA for in vivo applications (ex: Monocryl® sutures). Applicants demonstrate that modification of poly(caprolactone) with thiolated trehalose via thiol-ene chemistry would produce biodegradable trehalose glycopolymers. Applicants envision that many other methods may also be used to modify the polymers. For example, alkyne/azide click chemistry or any other method as appreciated by one skilled in the art may also be used to modify the polymers.

In one embodiment, the trehalose-functionalized caprolactones may be synthesized through ROP.

wherein $R_1$-$R_3$ are independently selected from hydrogen or a side chain comprising at least one carbon atom, and wherein at least one of $R_1$-$R_3$ is a side chain comprising -L-trehalose, wherein L is a linker molecule that links trehalose to the co-polymer through at least one of the trehalose hydroxyl groups (—OH), wherein DG is a biodegradable group, and wherein $R_5$ and $R_6$ are end groups, and wherein n=0-10, wherein m≥1.

In one embodiment, $R_5$ and $R_6$ are independently selected from the group consisting of -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, isocyanates, aminooxy (hydroxylamines), hydrazines, and biomolecules.

In one specific embodiment, $R_5$ and $R_6$ are independently selected from the group consisting of -Alkyl, -Alkenyl, -Alkynyl, -Aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), —H, and biomolecules.

In one embodiment, DG comprises at least one ester group.

In one embodiment, the ester group is in the backbone of the polymer.

In one preferred embodiment, the trehalose-functionalized caprolactones have the structure (4) of:

(4)

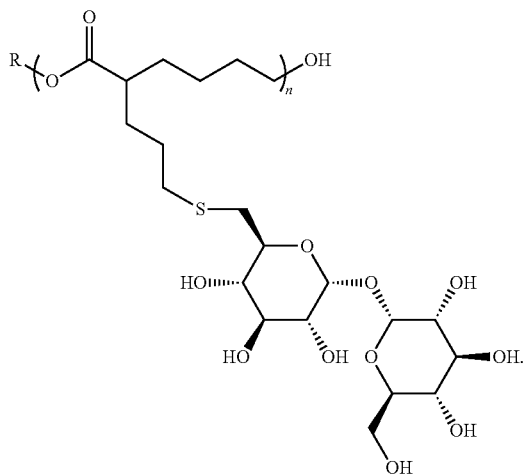

In one embodiment, Applicants envision that other backbone structures may also be used to produce degradable trehalose co-polymers. The specific backbones may include polycaprolactone, polycarbonate, polyurethane, polyanhydrides, Chitosan, hyaluronic acid, poly(amide), or poly(amino acid), poly(lactic acid), poly(glycolic acid), poly(dioxanone), poly(3-hydroxybutyric acid), poly(3-hydroxyvalerate), poly(valerolactone), poly(tartronic acid), poly(β-malonic acid), poly(propylene fumarate), poly(lactide-co-caprolactone), poly(lactic-co-glycolic acid), poly(3-hydroxybutyric acid-co-3-hydroxyvaleric acid), poly[1,4-bis(hydroxyethyl)terephthalate-alt-ethyloxyphosphate], poly[1,6-bis(p-carboxyphenoxy)hexane], poly(sebasic acid), and ethylglycinate polyphosphazene. The chemical structures of some of these suitable backbones are included as below:

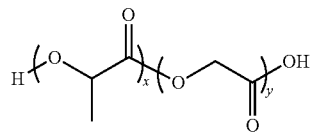

Poly(lactic-co-glycolic acid)

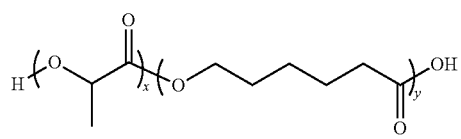

Poly(lactide-co-caprolactone)

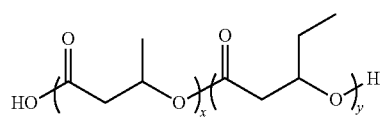

Poly(3-hydroxybutyric acid-co-3-hydroxyvaleric acid)

In one embodiment, the biodegradable trehalose co-polymers show good stabilization properties on biomolecules, e.g., proteins.

In some embodiments, biodegradable trehalose-based homopolymers or copolymers may be completely degraded after 24 hours under a base condition (e.g., 5% KOH). In one embodiment, biodegradable trehalose-based homopolymers or copolymers may be degraded slowly in aqueous solution by ester hydrolysis in aqueous solution. The hydrolysis can be accelerated to study the degradation by subjecting to 24 hours under a base condition.

Figure 35:
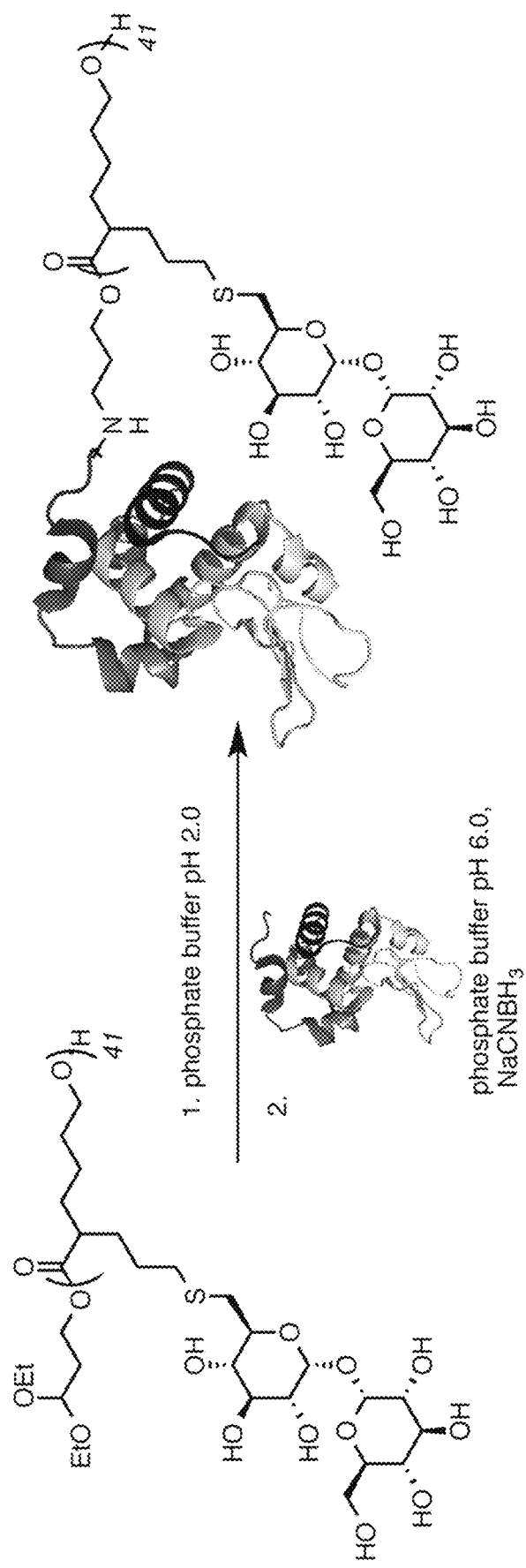
FIG. 35 if a drawing of Scheme 4.

In one embodiment, the biodegradable trehalose homo or co-polymers stabilize biomolecules when the biomolecules are chemically conjugated to the homo or co-polymers. Example 1 (e.g., Scheme 4, FIG. 35) shows the stabilization property of a biodegradable trehalose co-polymer over a protein (e.g., lysozyme) upon conjugation.

Figure 12:
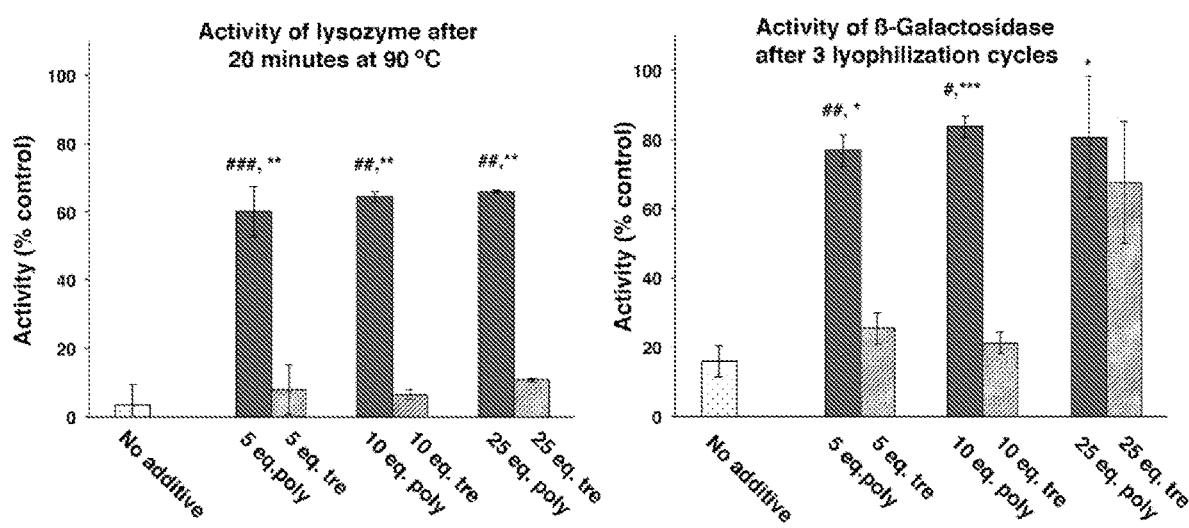
FIG. 12 (a and b) is a set of graphs showing stabilization of lysozyme (a) and β-Gal (b) by trehalose-CL. ###: p<0.001 compared to the same wt eq trehalose. ##: p<0.01 compared to the same wt eq trehalose. #: p<0.05 compared to the same wt eq trehalose *: p<0.001 compared to the negative control.: p<0.01 compared to the negative control. * p<0.05 compared to the negative control. White is no additive, dark is adding the trehalose caprolactone polymer, and gray is adding trehalose.

In one embodiment, the biodegradable trehalose co-polymers can also stabilize biomolecules when they are used as excipients, e.g., in the absence of chemical bond formation. Example 1 (e.g., FIG. 12) shows the stabilization property of a biodegradable trehalose co-polymer over proteins (e.g., lysozyme and β-Gal) against lyophilization stress when the co-polymers were used as excipients. Thus, similar to those as described in Applicants' previous PCT patent application No. PCT/US2013/023235 (e.g., disclosing many trehalose-based polymers for stabilizing biomolecules), biodegradable trehalose co-polymers show good stabilization properties on biomolecules, e.g., proteins.

In one aspect, the present invention relates to a method or process of synthesizing a biodegradable trehalose co-polymer as discussed above for stabilizing a biomolecule.

Applicants envision that the biodegradable trehalose co-polymers as discussed above may be synthesized by any suitable method as appreciated by one skilled in the art.

For example, as discussed below, one could synthesize one trehalose-based monomer and subsequently co-polymerize the trehalose-based monomer with a cyclic ketene acetal to form the desired biodegradable trehalose co-polymer. Alternatively, one could synthesize the backbone copolymer with pendant functional groups attached to the backbone. One could then attach trehalose groups to the co-polymer through the pendant functional groups to form the desired biodegradable trehalose co-polymer.

In one embodiment, Applicants note that bromine-functionalized caprolactone monomers could be synthesized and polymerized using tin catalysts (see, e.g., Xu et al., 2009). The pendant bromides could be installed using azide-alkyne "click" chemistry [e.g., displaced by sodium azide and sugar groups (glucose, maltose, and mannose)]. Block copolymers could also be made by copolymerizing with unfunctionalized caprolactone, which then self-assembled into micelles.

Oligosaccharides could also be functionalized with short-chain PEG chains and used as biodegradable backbones for degradable alternatives (Congdon et al., 2015). Dextran could be used as a biodegradable macroinitiator for the ATRP of a disaccharide monomer.[5]

Further, Applicants note that a degradable polymer could be synthesized through copolymerization of a cyclic ketene acetal (CKA) with a galactopyranose-functionalized styrene monomer (Xiao et. al., 2011).

In one embodiment, the biodegradable trehalose copolymer is produced through chemical synthesis. Preferably, the biodegradable trehalose copolymer is produced by using polymerization reactions including RAFT polymerization, ATRP, NMP, cyanoxyl-mediated free radical polymerization, conventional radical polymerization, or ROP. More preferably, the biodegradable trehalose copolymer is produced by using RAFT polymerization, ATRP, NMP, or ROP.

Preferred methods and processes for synthesizing biodegradable trehalose co-polymers are described in Examples 1 and 2.

In one embodiment, a method of synthesizing a biodegradable trehalose co-polymer for stabilizing a biomolecule comprises the steps of (a) incorporating a side chain comprising a trehalose molecule into a polymerizable monomer; and b) co-polymerizing the resulting monomer with a cyclic ketene acetal to obtain a co-polymer or glycopolymer.

In one preferred embodiment, the polymerizable monomer is selected from the group consisting of a styrene monomer, an acrylate monomer, a methacrylate monomer, an acrylamide monomer, a methacrylamide monomer, a vinyl monomer, a norborenyl monomer, and a strained cyclic alkene monomer. More preferably, the polymerizable monomer is a methacrylate monomer.

In one embodiment, the cyclic ketene acetal may include 5,6-benzo-2-methylene-1,3-dioxepane (BMDO), 2-methylene-4-phenyl-1,3-dioxalane (MPDL), 2-methylene-1,3-dioxalane, 2-methylene-4-hexyl-1,3-dioalane, 2-methylene-4-decyl-1,3-dioalane, 2,4-dimethylene-1,3-dioxalane, 2,5-dimethylene-1,3-dioxane, 2-methylene-1,3-dioxepane (MDO), 2,5-methylene-1,3-dioxane, 4,7-dimethyl-2-methylene-1,3-dioxepane, 4-phenyl-2-propenylene-1,3-dioxalane, 2-methylene-1,3-dioxe-5-pene, 2-ethylidene-4-methyl-1,3-dioxane, 2-ethylidene-4-ethyl-1,3-dioxane, 2-ethylidene-1,3-dioxane, 1-vinyl-4,7-dioxaspiro-[2,4]heptane, I-vinyl-4,9-dioxaspiro-[2.6]nonane, 1-vinyl-6,7-benzo-4,9-dioxaspiro[2.6]nonane, 9,9-disubstituted-4-methylene-3,5,8,10-tetraoxabicyclo[5.3.0]decane, 3,9-bis-methylene-2,4,8,10-tetraoxa-spiro[5,5]undecane, or 2-methylene-1,3,6-trioxocane.

In one preferred embodiment, the cyclic ketene acetal may be 5,6-benzo-2-methylene-1,3-dioxepane (BMDO).

In one embodiment, the step of co-polymerizing the resulting monomer to obtain biodegradable trehalose co-polymers is performed by any one of, but not limited to the techniques of RAFT polymerization, ATRP, NMP, cyanoxyl-mediated free radical polymerization, conventional radical polymerization, or ROP. Preferably, the step of co-polymerizing the resulting monomer to obtain a homopolymer or copolymer is performed by reversible addition-fragmentation chain transfer (RAFT) polymerization or ROP.

In one embodiment, other methods or processes may also be used to produce the present biodegradable trehalose co-polymers. For example, co-polymers with biodegradable bonds on the backbone and pendant functional groups attached to the backbone may be synthesized and trehalose groups may be later attached to the backbone of the co-polymer through the pendant functional groups.

In one embodiment, a method of synthesizing a biodegradable trehalose co-polymer for stabilizing a biomolecule may comprise the steps of (a) co-polymerizing polymerizable monomers to obtain a non-trehalose co-polymer; and (b) incorporating a side chain comprising a trehalose molecule into the non-trehalose co-polymer or glycopolymer to form the degradable trehalose co-polymer. Applicants envision that there are functional groups on the non-trehalose homopolymer or co-polymer where trehalose may be incorporated into the homopolymer or co-polymer.

In one specific embodiment, a method of synthesizing a biodegradable trehalose polymer for stabilizing a biomolecule may comprise the steps of a) polymerizing a cyclic ester with an alcohol with to form a polymer, where in the cyclic ester includes a pendant functional group; b) preparing a thiolated trehalose monomer, c) reacting the polymer with the thiolated trehalose monomer to form the biodegradable trehalose polymer.

In one embodiment, the biodegradable trehalose polymer for stabilizing a biomolecule may be a methacrylate-based polymer with a side chain functional group.

In one embodiment, the cyclic ester is a caprolactone. Preferably, the cyclic ester is allyl-functionalized caprolactone (aCL). Allyl group is used as a pendant functional group wherein trehalose groups can be attached. Example 1 shows that allyl-functionalized caprolactone (aCL) may be synthesized in one step following literature procedures (Ende et al., 2008).

In one embodiment, the alcohol is a primary alcohol. The primary alcohol may be used an initiator for polymerization of aCL.

In one embodiment, the polymerization in step (a) is a ROP. In one embodiment, the ROP in step (a) may further need a catalyst. Preferably, the catalyst is triazabicyclodecane (TBD), an organic catalyst.

In one embodiment, the thiolated trehalose monomer has the structure of:

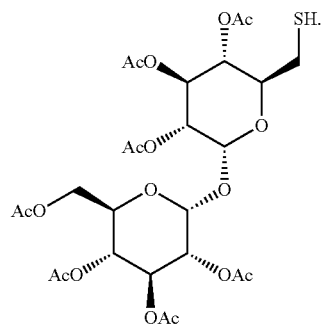 [SMILES: CC(=O)OC[C@H]1O[C@H](O[C@H]2O[C@H](CS)[C@@H](OC(C)=O)[C@H](OC(C)=O)[C@H]2OC(C)=O)[C@H](OC(C)=O)[C@@H](OC(C)=O)[C@@H]1OC(C)=O]

Example 1 (Scheme 1) shows methods and processes for synthesizing thiolated trehalose monomeric unit.

In one embodiment, a thiol-ene reaction was used to connect the co-polymer with the thiolated trehalose monomer to form the biodegradable trehalose co-polymer.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

EXAMPLES

Example 1

Caprolactone Polymers

Herein we Describe the Synthesis of a Biodegradable Trehalose Polymer Using Ring-opening polymerization (ROP). We show that this polymer when added to proteins stabilizes the biomolecules to stressors such as heating. Subsequent conjugation to the protein lysozyme was demonstrated using reductive amination. We expect that these polymers can function as improved PEG replacements in protein-polymer therapeutics due to their combination of biodegradability and stabilization abilities. They may also be interesting added as excipients.

Synthetic Methods

Synthesis of Thiolated Trehalose Monomeric Unit.

A thiol-functionalized trehalose molecule was synthesized in 5 steps, with 19% overall yield (Scheme 1; the numericals of compounds are limited in Example 1). Briefly, the primary alcohols of trehalose was selectively functionalized using the bulky trityl protecting group and the remaining hydroxyls converted to the acetate ester using acetic anhydride to form 2. Deprotection of the trityl ether under acidic conditions, followed by tosylation of the exposed alcohol led to tosyl ester 4, which was displaced using the nucleophile potassium thioacetate to yield the thioacetate ester 5. Selective removal of the more labile thioester led to the thiolated trehalose 6.

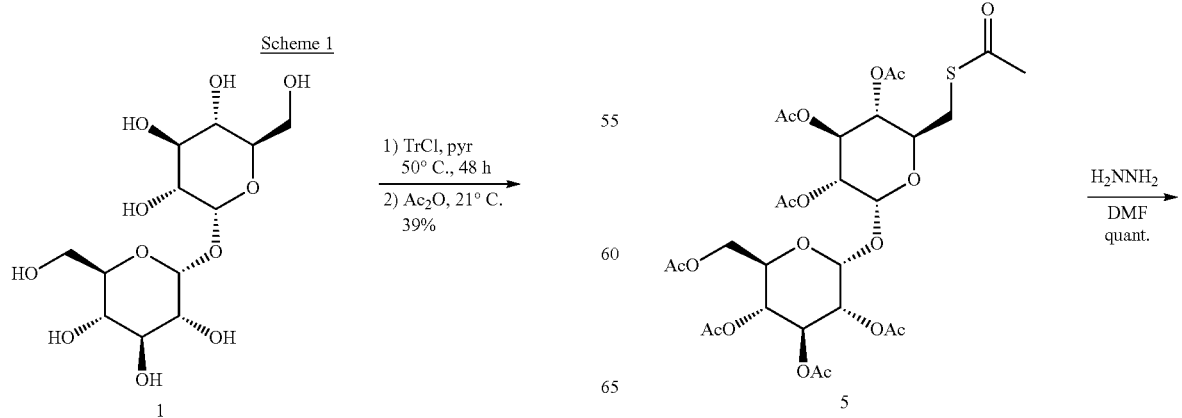

Scheme 1

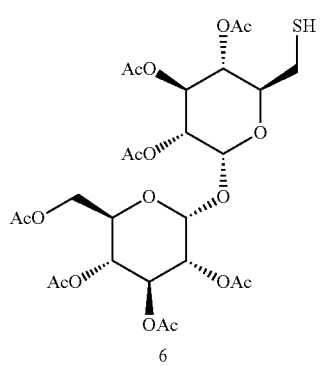

6

Experimental Details

Figure 2:
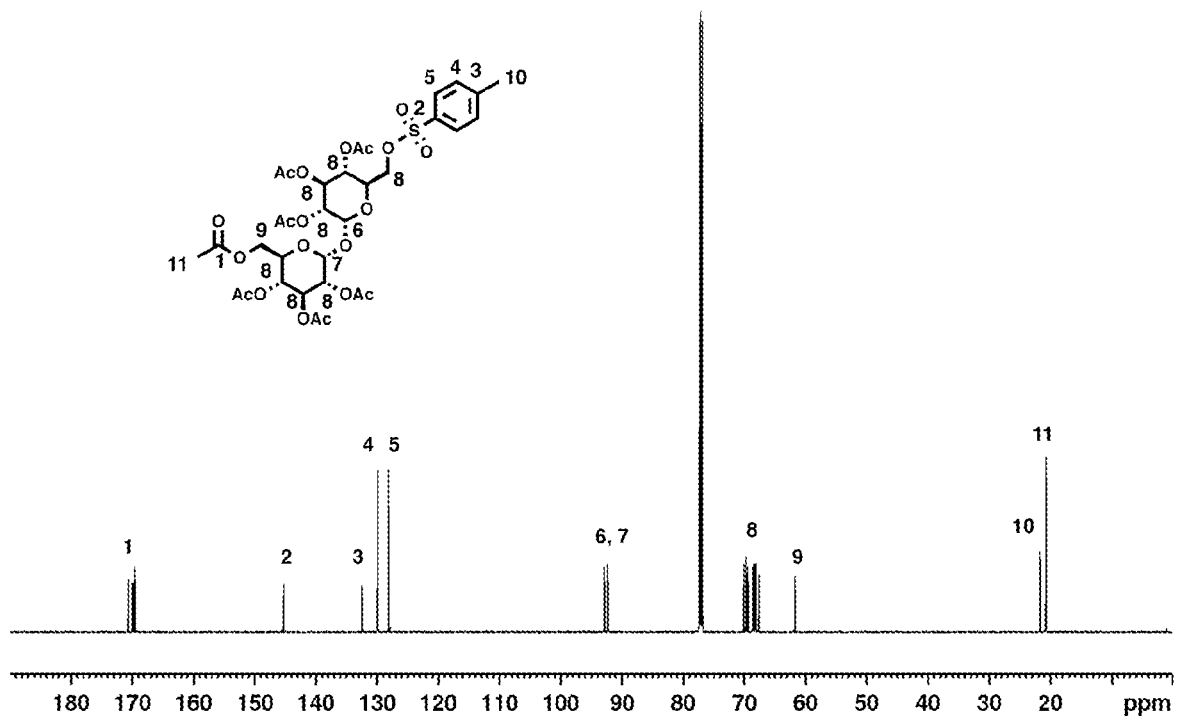
FIG. 2 is a graph showing $^{13}$C-NMR (500 MHz, CDCl$_3$) of tosylated trehalose 4.
Figure 3:
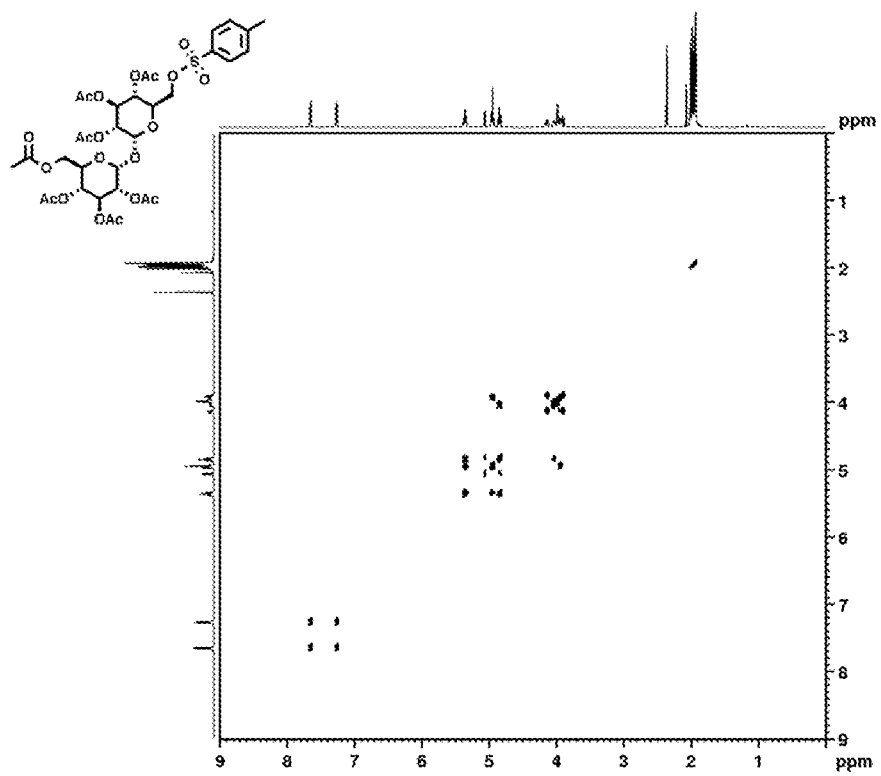
FIG. 3 is a graph showing HSQC 2D-NMR (500 MHz, CDCl$_3$) of tosylated trehalose 4.

Tosyl trehalose 4. In a two-neck round bottom flask, monohydroxylheptaacetyltrehalose (Lee et al., 2013) (1.08 g, 1.69 mmol) was dissolved in anhydrous CH$_2$Cl$_2$ (10 mL) under argon. Dimethylamino pyridine (DMAP) (41 mg, 0.34 mmol) and anhydrous pyridine ((0.4 mL, 5.1 mmol) were added and the reaction solution cooled to 0° C. in an ice-water bath. Tosyl chloride 970 mg, 5.1 mmol) was added slowly as a solid and the solution stirred for an additional 30 minutes at 0° C. before warming to room temperature for 14 hours. The crude mixture was diluted with additional CH$_2$Cl$_2$ and washed with water and brine. The organic layer was then dried with MgSO$_4$ and concentrated in vacuo. The crude solid was purified by silica gel flash column chromatography (eluent 4:1 CH$_2$Cl$_2$:EtOAc) to obtain a crispy white solid (1.062 g, 1.34 mmol, 79.5%). $^1$H-NMR (500 MHz in CDCl$_3$) δ: 7.74 (d, J=8.3 Hz, 2H), 7.34 (d, J=8 Hz, 2H), 5.47-5.41 (m, 2H), 5.14 (d, J=3.9 Hz, 1H), 5.05-5.01 (m, 3H), 4.93-4.89 (m, 2H), 4.21 (dd, J=12.1 Hz, 6.7 Hz, 1H), 4.14-3.94 (m, 5H), 2.44 (s, 3H), 2.09 (s, 3H), 2.06 (s, 3H), 2.05 (s, 3H), 2.03 (s, 3H), 2.02 (s, 3H), 2.01 (s, 3H), 2.00 (s, 3H). $^{13}$C NMR: (500 MHz in CDCl$_3$): δ: 169.0, 169.9, 169.6, 169.6, 169.5, 169.5, 145.3, 132.4, 129.9, 128.0, 92.8, 92.3, 70.0, 69.7, 69.7, 69.3, 68.6, 68.4, 68.2, 68.1, 67.5, 61.7, 21.7, 20.7, 20.7, 20.6, 20.6, 20.6, 20.5. IR: ν=2950, 1744, 1432, 1368, 1221, 1190, 1177, 1138, 1079, 1035, 1016, 988, 911, 862, 805 cm$^{-1}$. HRMS-ESI (m/z) [M+H$_2$O]$^+$ calcd for C$_{33}$H$_{44}$O$_{21}$S, 808.2096; found 808.2226. FIG. 1 shows $^1$H-NMR (500 MHz, CDCl$_3$) of tosylated trehalose 4. FIG. 2 shows $^{13}$C—NNR (500 MHz, CDCl$_3$) of tosylated trehalose 4. FIG. 3 shows HSQC 2D-NMR (500 MHz, CDCl$_3$) of tosylated trehalose 4.

Figure 4:
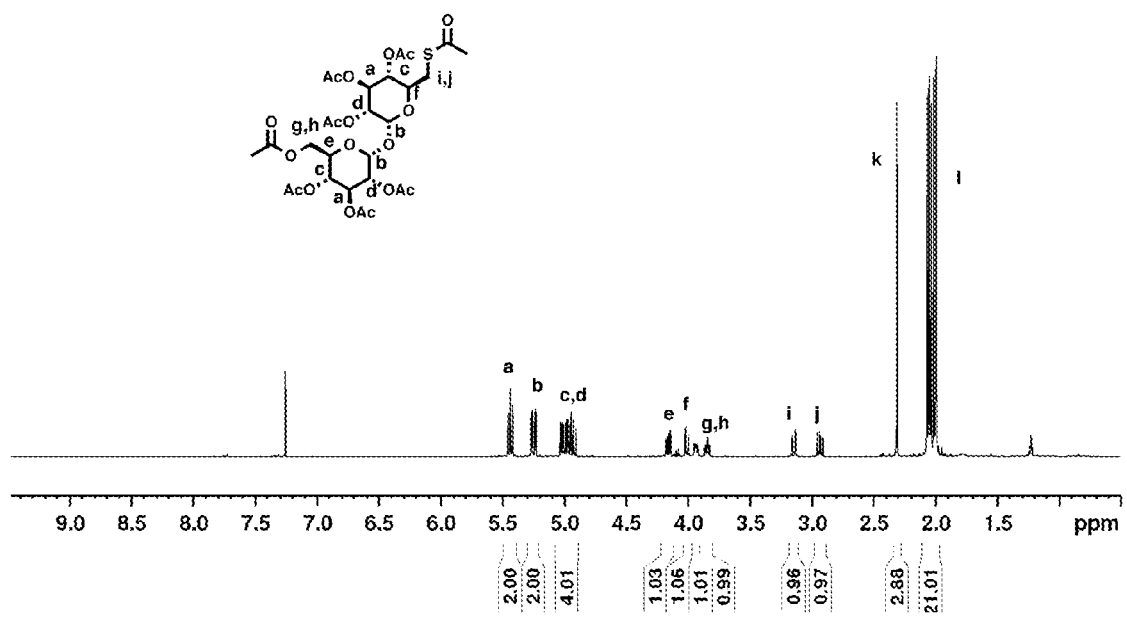
FIG. 4 is a graph showing $^1$H-NMR (500 MHz, CDCl$_3$) of thioacetate trehalose 5.
Figure 5:
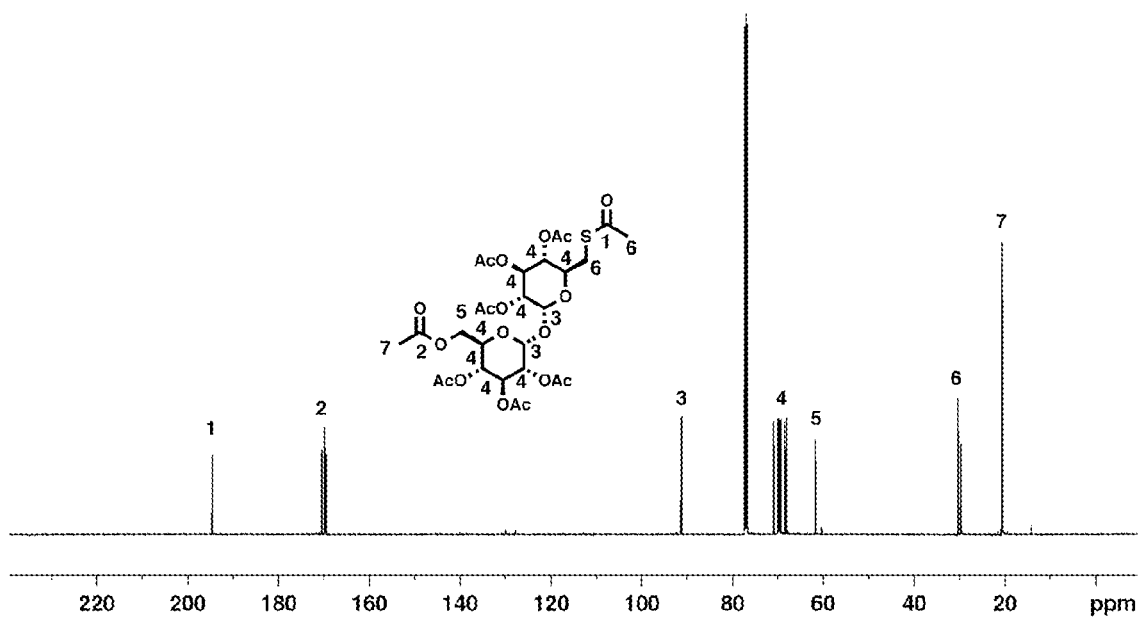
FIG. 5 is a graph showing $^{13}$C-NMR (500 MHz, CDCl$_3$) of thioacetate trehalose 5.

Thioacetate trehalose 5. In a two-neck round bottom flask, tosylated trehalose 4 (1.08 g, 1.36 mmol) was dissolved in anhydrous DMF (10 mL) under argon. Potassium thioacetate (480 mg, 4.20 mmol) was added and the reaction solution heated to 80° C. for 14 hours. After cooling to room temperature, DMF was removed in vacuo. The crude brown solid was redissolved in CH$_2$Cl$_2$ and washed with water, sat. NaHCO$_3$(2×), water, and brine. The organic layer was dried with MgSO$_4$ and concentrated in vacuo. The crude oil was purified by silica gel flash column chromatography (eluent 4:1 CH$_2$Cl$_2$:EtOAc) to obtain 3 as a crispy tan solid (835.2 mg, 1.20 mmol, 89%). $^1$H NMR: (500 MHz in CDCl$_3$) δ: 5.45 (t, J=9.8 Hz, 2H), 5.26 (dd, J=4, 11.2 Hz, 2H), 5.05-4.91 (m, 4H), 5.16 (dd, 1H), 4.00 (dd, 1H), 3.88-3.87 (m, 1H), 3.85 (ddd, 1H), 3.16 (dd, J=2.8, 14.4, 1H), 2.94 (dd, J=7.6, 14.4, 1H), 2.32 (s, 3H), 2.08 (s, 3H), 2.06 (s, 3H), 2.06 (s, 3H), 2.04 (s, 3H), 2.02 (s, 3H), 2.00 (s, 3H), 2.00 (s, 3H). $^{13}$C NMR: (500 MHz, CDCl$_3$) δ: 194.6, 170.6, 169.9, 169.9, 169.9, 169.7, 169.7, 159.6, 91.4, 91.2, 70.9, 70.0, 70.0, 69.8, 69.6, 69.3, 68.5, 68.2, 61.8, 30.4, 29.8, 20.7, 20.6, 20.6, 20.6, 20.5. IR: ν=2957, 1746, 1694, 1431, 1367, 1212, 1161, 1134, 1034, 981, 962, 900, 803 cm$^{-1}$. FIG. 4 shows $^1$H-NMR (CDCl$_3$, 500 MHz) of thioacetate trehalose 5. FIG. 5 shows $^{13}$C-NMR (CDCl$_3$, 500 MHz) of thioacetate trehalose 5.

Figure 6:
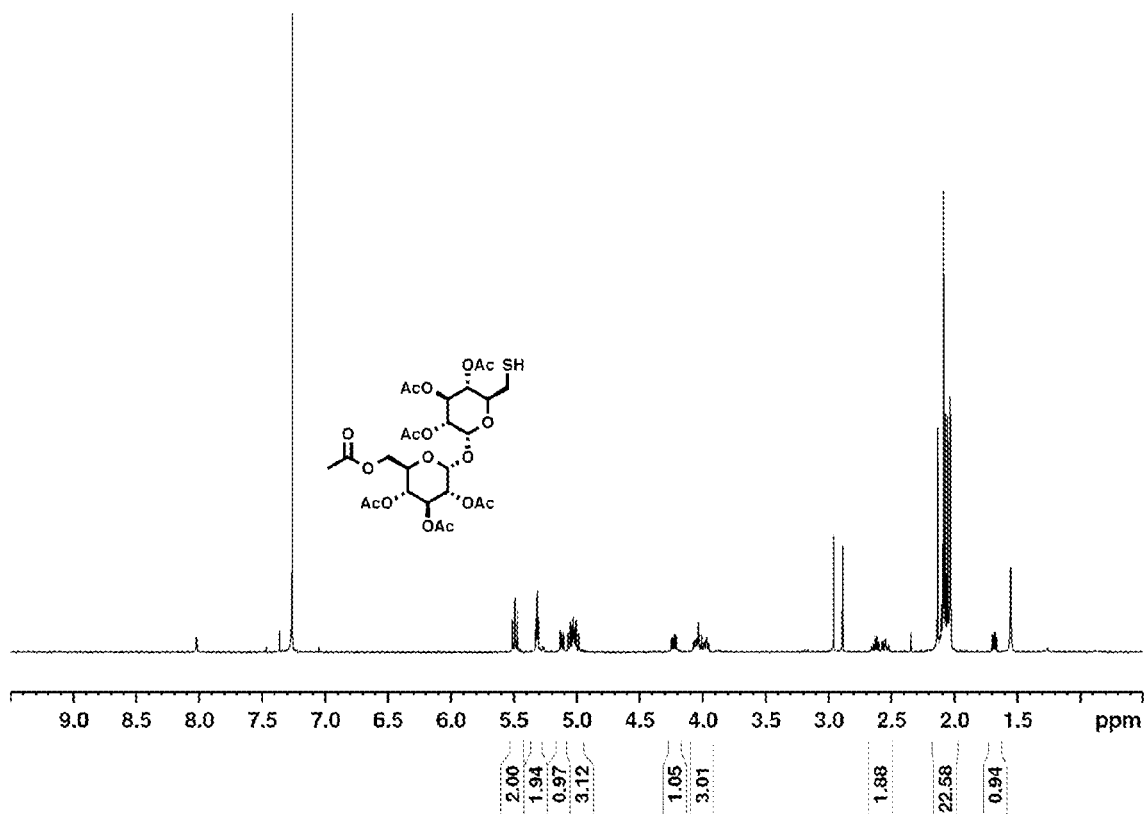
FIG. 6 is a graph showing $^1$H-NMR (500 MHz, CDCl$_3$) of thiol trehalose 6.

Thiolated trehalose 6. In a 20 mL screw-top vial, thioacetylated trehalose 5 (628.3 mg, 0.90 mmol) was dissolved in dry DMF (18 mL) under argon. Acetic acid (51 µL, 0.90 mmol) was added and the solution was stirred for 10 minutes. Hydrazine hydrate (70-82% in H2O, 55 µL, 0.90 mmol) was then added and the reaction solution was stirred at 21° C. for a further 2 hours. Acetone (75 µL) was added to quench the reaction. The solution was diluted with EtOAc, washed 2× with brine, then dried over MgSO$_4$. Solvent and residual DMF were removed in vacuo by freeze-drying from benzene to yield a light tan solid (597 mg, 0.90 mmol, >99%). FIG. 6 shows $^1$H-NMR (CDCl$_3$, 500 MHz) of thiol trehalose 6.

Synthesis of Poly(Caprolactone) with Reactive Pendant Units and Installation of Trehalose Moieties Polycaprolactone was selected as the backbone due to its previous use in the medical field and because of the well-developed chemistries for its polymerization and modification (Ende et al., 2008; Silvers et al., 2012; Parrish et al., 2002; Parrish et al., 2005). Allyl-functionalized caprolactone (aCL) was first synthesized in one step following literature procedures (Ende et al., 2008). The ROP of aCL was conducted in toluene with functional—used for ease of characterization. For polymers to be used for conjugations, 2,2-diethoxyethanol was used as a protected protein-reactive group.

Scheme 2

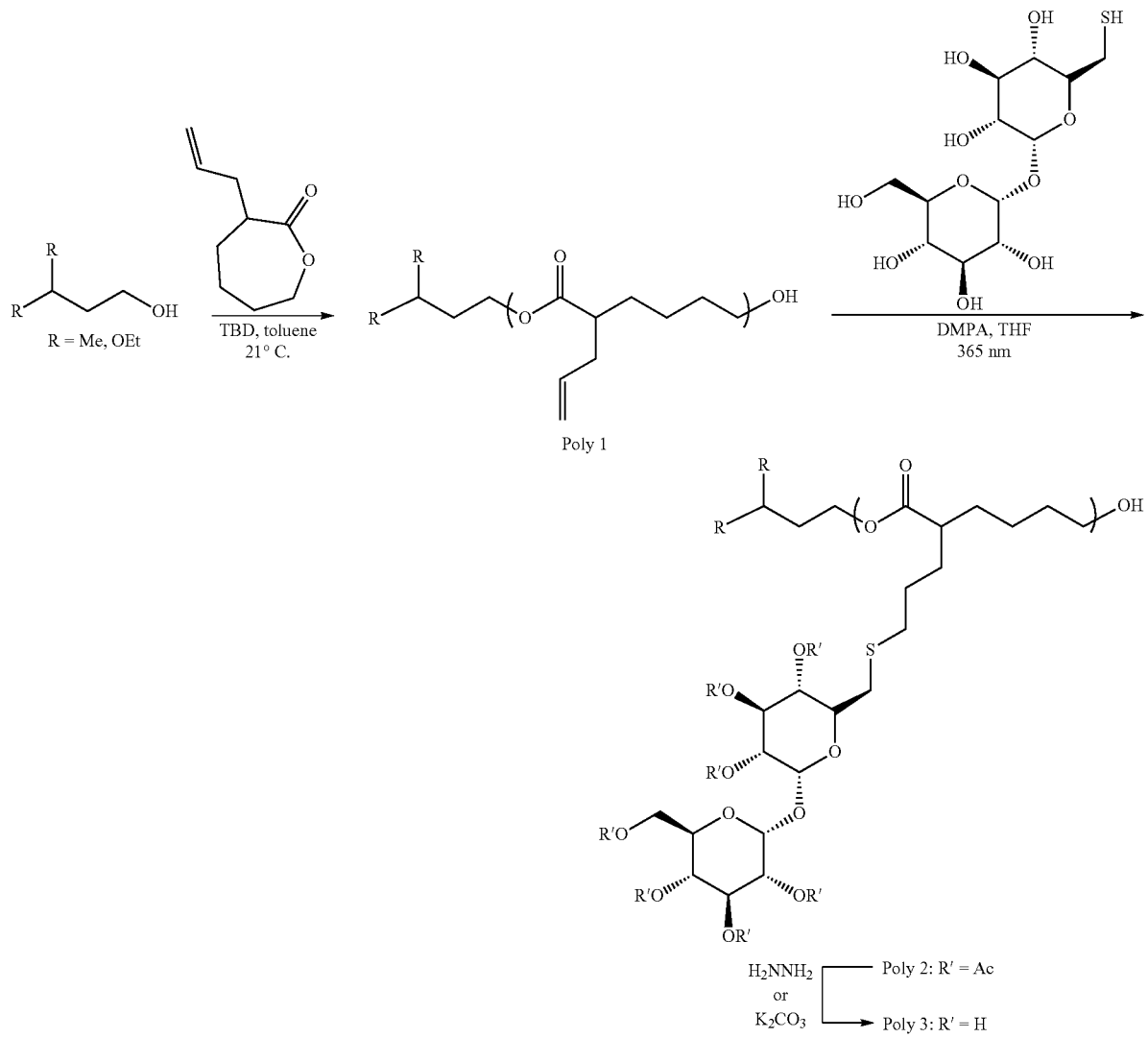

Figure 7:
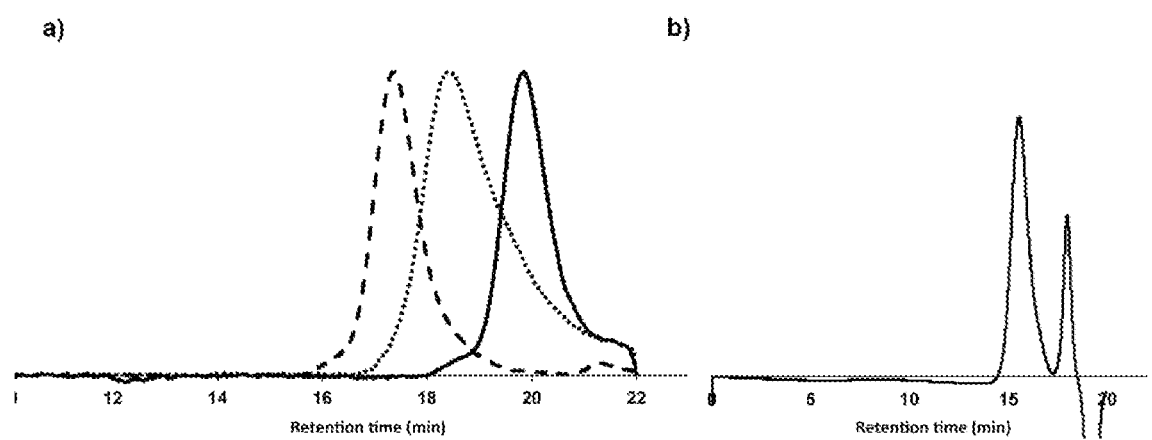
FIG. 7 (a and b) is a set of graphs showing a) Gel permeation chromatogram of Poly 1-3, Red: Poly 1, Blue: Poly2, Green: Poly3 and b) Size exclusion chromatography of Poly3.

Acetate-protected trehalose thiol was then installed through a photo-initiated thiol-ene reaction with dimethoxyphenylacetophenone (DMPA) as the photoinitiator (Campos et al., 2008). Full conversion was confirmed by the loss of the allyl peaks at 5.7 ppm in the $^1$H-NMR. The integrity of the polyester backbone was confirmed after each modification by GPC, with an increase in molecular weight and no significant broadening after the attachment of the acetate-protected trehalose units (FIG. 7a).

Removal of the acetate groups could be achieved without hydrolysis of the backbone by either using hydrazine in DMF or 50 mM $K_2CO_3$ in $CHCl_3$/MeOH. A slight broadening was observed when the polymer was analyzed by GPC in organic solvent (FIG. 7a), however when the polymer was analyzed by SEC in aqueous solvent no such increase in Đ could be seen (FIG. 7b). Therefore the increase in Đ was hypothesized to be due to interactions between the polysaccharide hydroxyls and the column stationary phase, and not due to any cleavage of the backbone esters.

Modifications to these chemistries could be made. Other protein-reactive functionalities could be used, including thiol-reactive maleimide and pyridyl disulfide groups. These could be installed using a functional alcohol initiator or through post-polymerization esterification with the omega hydroxyl group. A sample post-polymerization modification is shown in Scheme 3, where a methacrylate group was installed via esterification.

Scheme 3

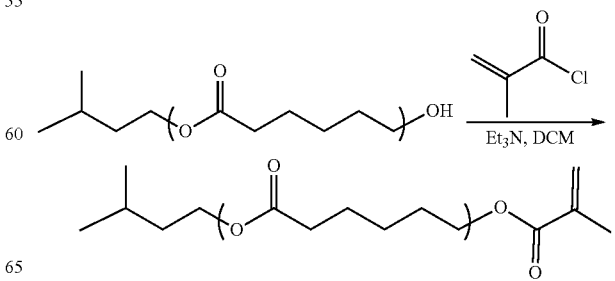

The nature of click chemistry could also be varied. For example, reagent pairs such as azide-alkyne (Parrish et al., 2005) or vinylsulfone-thiol (Wang et al., 2011) could be used to attach the trehalose moieties to the caprolactone backbone.

Experimental Details

Figure 8:
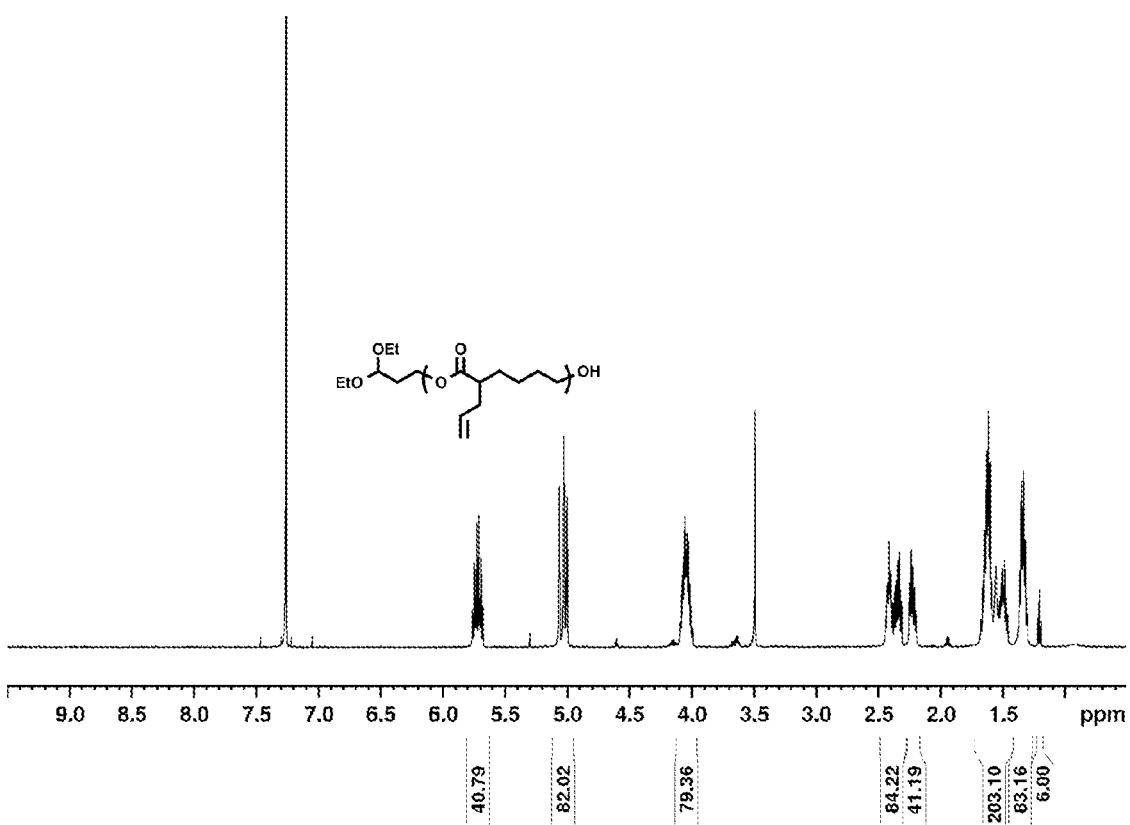
FIG. 8 is a graph showing $^1$H-NMR (CDCl$_3$, 500 MHz) of allyl-functionalized poly(caprolactone).

Representative ring-opening polymerization of poly(allyl-caprolactone). A 25 mL two-neck round bottom flask was equipped with a stir bar and flame-dried. Triazabicyclodecane (6.6 mg, 47 µmol) added and the flask was evacuated and refilled with nitrogen three times. Anhydrous toluene (600 µL) and 2,2-diethoxyethanol (3.3 mg, 22 µmol in 10 µL toluene) was added via nitrogen-purged syringe and the initiator-catalyst mixture was allowed to stir for 30 minutes at 21° C. before adding allyl-caprolactone (193 mg, 1270 µmol) via nitrogen-purged syringe. The reaction mixture was stirred at 21° C. and aliquots were removed for $^1$H-NMR analysis via syringe. After the desired conversion was achieved (5.5 h), the reaction was quenched with H$_2$O/MeOH and residual monomer and catalyst were removed by dialyzing with Spectra/P or dialysis membrane (MWCO 1 kD) against MeOH to give the polymer as a colorless oil. FIG. 8 shows $^1$H-NMR (CDCl$_3$, 500 MHz) of allyl-functionalized poly(caprolactone).

Figure 9:
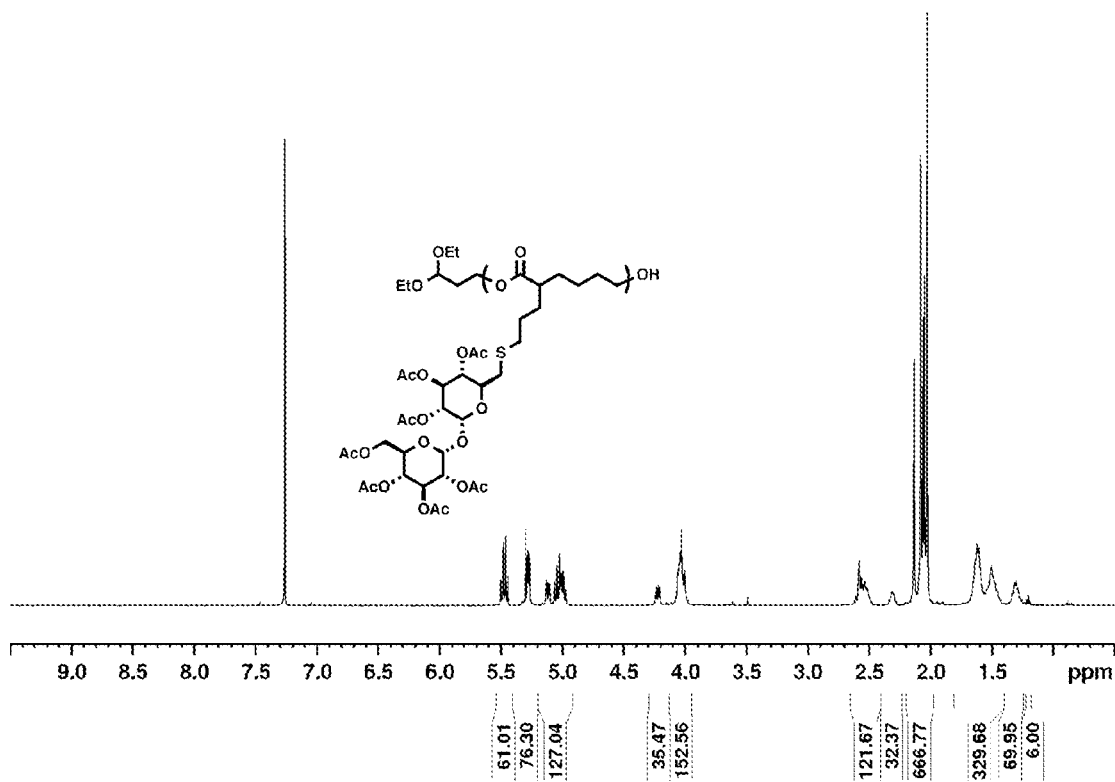
FIG. 9 is a graph showing $^1$H-NMR (CDCl$_3$, 500 MHz) of acetate-protected trehalose-caprolactone polymer.

Synthesis of functional polyestersvVia thiol-ene reaction. In a 1.5 mm sample vial, poly(allyl-caprolactone (15.6 mg) was dissolved in anhydrous THF (700 µL). Thiol trehalose 4 (208 mg) and 2,2-dimethoxy-2-phenylacetophenone (13.5 mg) were added and the vial was sealed with a rubber septum, degassed for 10 minutes, and exposed to a handheld UV lamp (λ=365 nm) for 4 hours. The crude solution was then precipitated into cold MeOH to yield the acetate protected trehalose polyester. FIG. 9 shows $^1$H-NMR (CDCl$_3$, 500 MHz) of acetate-protected trehalose-caprolactone.

Figure 10:
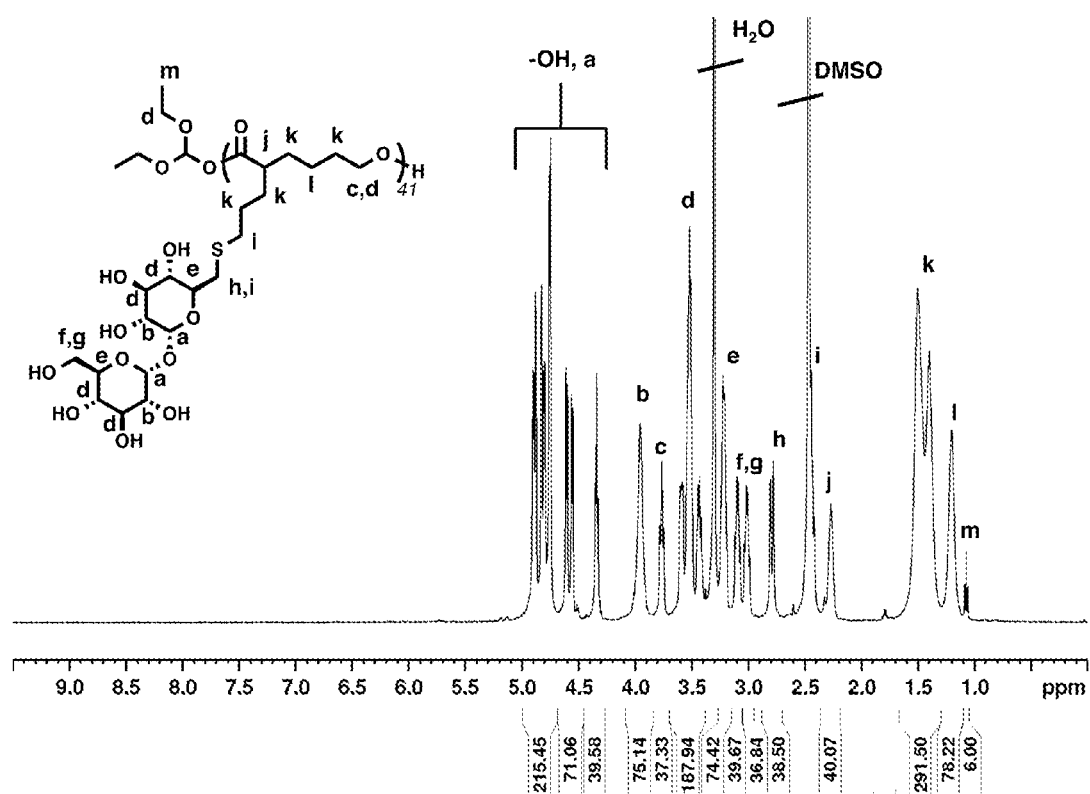
FIG. 10 is a graph showing $^1$H-NMR (500 MHz, DMSO-d$_6$) of acetal-end functionalized trehalose-caprolactone.

Deprotection of trehalose polyester. Hydrazine was used for global deprotection of the trehalose acetate esters to avoid base-catalyzed hydrolysis of the polyester backbone and to simultaneously expose the hydroxylamine endgroup.[34] Alternatively, K$_2$CO$_3$ could be used as a mild base. In a 20 mL screw-top vial, acetylated trehalose polyester was dissolved in DMF or CHCl$_3$/MeOH. Hydrazine (78-82% in H2O) or K$_2$CO$_1$(50 mM) was added and the reaction solution was stirred for 20 hours for hydrazine or 3 hours for K$_2$CO$_3$. The formation of hydrazine acetate could be observed as a fine white precipitate as the reaction progressed. To quench these reactions, acetone was added. For all deprotections, the reaction mixture was diluted with H$_2$O and dialyzed against 50% MeOH/H$_2$O with 1 kD MWCO dialysis tubing. FIG. 10 shows $^1$H-NMR (500 MHz, DMSO-d$_6$) of acetal-functionalized trehalose-caprolactone.

Figure 11:
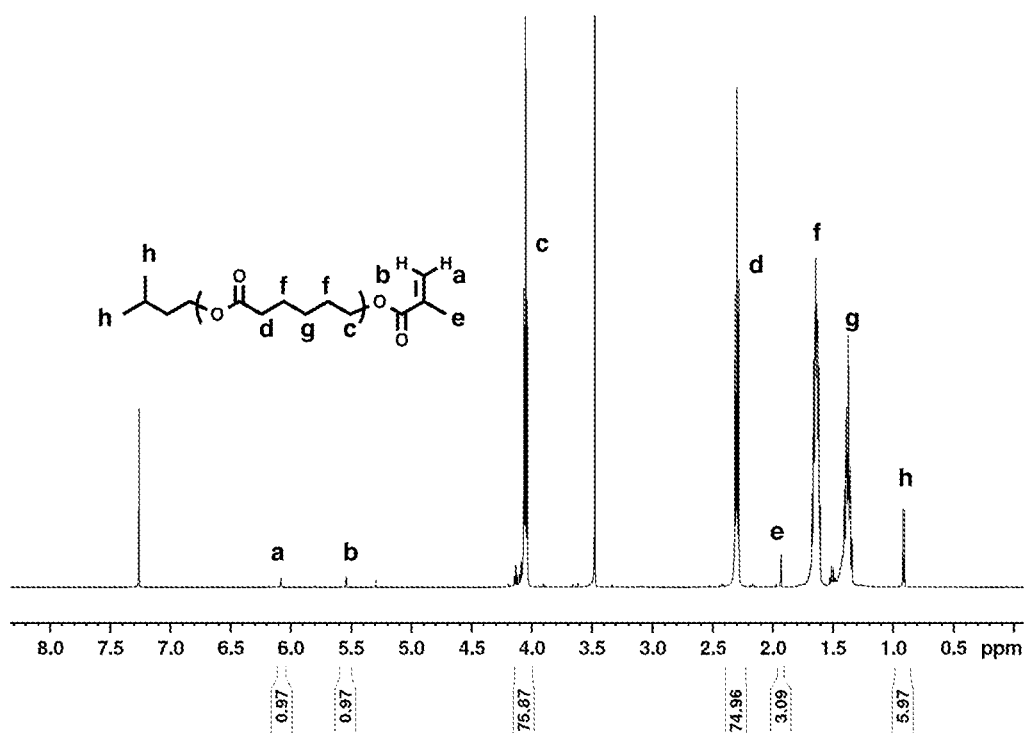
FIG. 11 is a graph showing $^1$H-NMR (500 MHz, CDCl$_3$) of poly(caprolactone) with a methacrylate end group prepared post functionalization.

Modification of acetate protected trehalose-caprolactone with methacryloyl chloride. Acetate-protected trehalose-caprolactone (15 mg) was dissolved in 1 mL anhydrous dichloromethane. Dry triethylamine (21 µL, dried over molecular sieves) was added and the mixture let stir briefly and cooled to 0° C. Methacryloyl chloride (15 µL) was then added and the mixture stirred at 0° C. for 1 hour and then at room temperature. After 28 hours, the mixture was concentrated and the crude solid was re-dissolved in 200 µL DCM and precipitated into 15 mL cold MeOH. The solid was separated by 10 minutes centrifugation and the solution removed. Dissolution and precipitation were repeated and the product was dried in vacuo to reveal a white solid. FIG. 11 shows.

Stabilization of model proteins using trehalose-caprolactone as excipient. The ability of these biodegradable trehalose polymers to stabilize proteins was confirmed through heat and lyophilization stress assays. We have previously used trehalose polymers to demonstrate stabilization of lysozyme against heat burden and β-galactosidase (β-Gal) against lyophilization, respectively (Mancini and Maynard, 2012; Lee et al., 2013). Therefore, these proteins were also selected to test the biodegradable trehalose polymers. First, lysozyme was stressed by heating to 90° C. for 20 minutes. To determine the concentration range and effectiveness of the polymer, samples were prepared with 5 to 25 wt eq. of both trehalose-CL as well as trehalose alone. The activity of lysozyme was determined by using a commercially available kit, wherein protein activity is measured by fluorescence resulting from lysis of fluorescein-labeled *Micrococcus lysodeikticus*. Lysozyme samples containing trehalose-CL as an excipient retained up to 66% of native activity, while lysozyme alone displayed 4% retention (FIG. 12*a*). Trehalose as additive was not significantly different from the negative control.

The stabilization of β-Gal against lyophilization stress was also measured. Three 12-hour desiccation cycles were performed with and without trehalose-CL and trehalose as additives. The activity of β-Gal was determined by reaction with ortho-nitrophenol galactose (ONPG). When incubated with β-Gal, release of the yellow-colored o-nitrophenol from ONPG can be monitored at 405 nm. Samples containing trehalose-CL as an excipient maintained up to 84% of native activity, while the unstabilized protein retained only 16% (FIG. 12*b*). For this protein, high equivalents of trehalose were able to stabilize β-Gal to the same extent as the polymer, up to 67% at 25 equivalents of trehalose.

Figure 13:
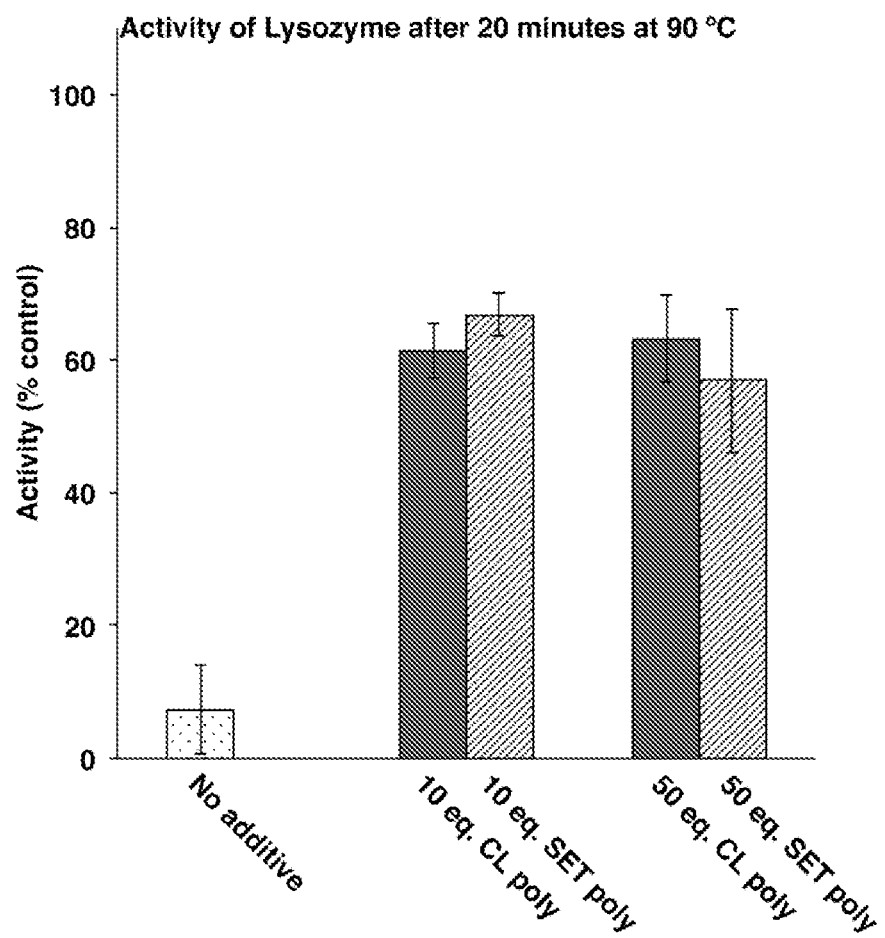
FIG. 13 is a graph showing comparison of trehalose-caprolactone polymer (dark) and styrenyl ether trehalose polymer (SET poly; gray) in the stabilization of lysozyme. *: p<0.001 compared to the negative control.: p<0.01 compared to the negative control. White is no additive.

Trehalose-CL and a styrenyl ether trehalose (SET) polymer previously described were also directly compared in their stabilization of lysozyme (FIG. 13) (Lee et al., 2013). In this test, trehalose-CL maintained up to 61% of lysozyme native activity, while the SET polymer retained up to 67%. Thus, the degradable trehalose glycopolymer was similar in stabilization ability to the non-degradable version.

Experimental Details

Protein Activity

Lysozyme and β-Galactosidase were assayed as previously described (Lee et al., 2013). Briefly, the activity of lysozyme was determined by using a commercially available kit, wherein protein activity is measured by fluorescence resulting from lysis of fluorescein-labeled *Micrococcus lysodeikticus*. The activity of β-Gal was determined by reaction with ortho-nitrophenol galactose (ONPG). When incubated with β-Gal, release of the yellow-colored o-nitrophenol from ONPG can be monitored at 405 nm.

Environmental Stressors

Heat studies with lysozyme were carried out as previously described; lysozyme was heated at 0.02 mg/mL for 20 minutes at 90° C. (Lee et al., 2013). Enzyme solutions were then diluted and activity was assayed using the EnzChek activity kit. Lyophilization studies with β-galactosidase were carried out as previously described; β-Gal was subjected to three 12 hour lyophliization cycles before dilution. Activity was assayed by monitoring the hydrolysis of o-nitrophenol galactose (ONPG) at 405 nm.

Degradation of Trehalose-Caprolactone Polymer

Figure 14:
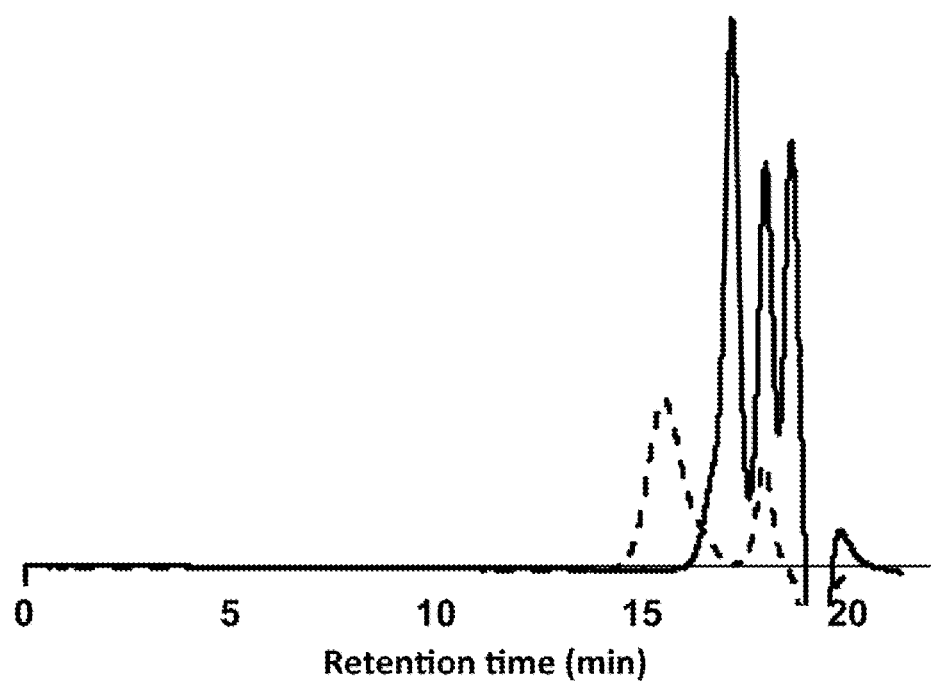
FIG. 14 is a set of graphs showing size exclusion chromatogram of caprolactone-trehalose polymer pre- and post-degradation with 5% KOH.

The degradation of the caprolactone-trehalose polymer upon treatment with 5% KOH was also demonstrated. Analysis by SEC after 24 hours showed a drastic shift toward small molecular weight fragments (Mn=300) with complete loss of polymer (FIG. 14). No further degradation was observed upon longer incubation, implying that these peaks corresponded to the substituted 6-hydroxyl hexanoic acid monomer unit. This data show that the polymers are degradable by ester hydrolysis.

Experimental Details

Degradation of trehalose-caprolactone. In a 1.5 mL Eppendorf tube, trehalose polyester (3 mg) was dissolved in 5% KOH (1 mL) and placed on a rotating plate at 4° C. Aliquots (300 µL) were removed after 1, and 5 days, neutralized with equivalent volumes of 5% HCl, and lyophilized to remove solvent before re-dissolving in SEC mobile phase.

Conjugation of Trehalose-Caprolactone to Lysozyme Via Reductive Amination and Conjugate Stabilization After confirmation that the trehalose-CL polymers were efficient stabilizers as excipients, the polymers were conjugated to lysozyme as a model protein. By using a functional alcohol as ROP initiator, an acetal was installed at the alpha end of the polymer. Acidic hydrolysis exposed the aldehyde, which underwent reductive amination with one or more of the 6 lysine amino acids on lysozyme (Scheme 4 FIG. 35)(Diamond, 1974).

Figure 15:
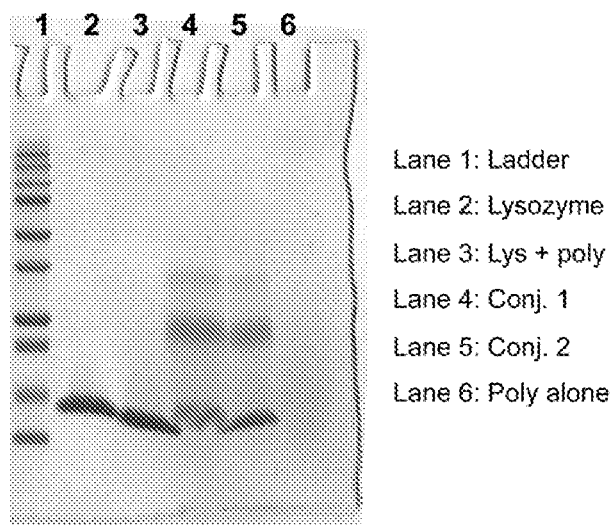
FIG. 15 is a graph showing SDS-PAGE gel depicting conjugation of trehalose-caprolactone polymer to lysozyme.

Conjugates were observed by SDS-PAGE (FIG. 15). A mixture of mono- and bis-conjugate was observed, as reductive amination is not a site-selective conjugation technique (Bentley et al., 1998).

Figure 16:
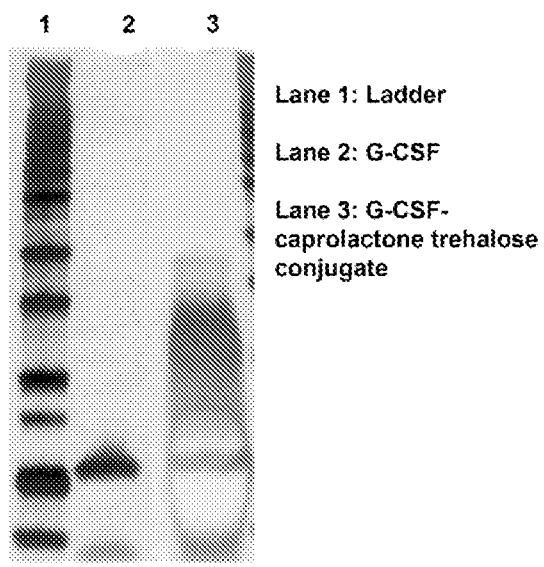
FIG. 16 is a graph showing SDS-PAGE gel with silver stain depicting conjugation of trehalose-caprolactone polymer to G-CSF.

Additionally, the conjugation of the trehalose-caprolactone was carried out with granulyte-stimulating growth factor (G-CSF), an important therapeutic protein (FIG. 16).

Experimental Details

Conjugation to lysozyme. Acetal-functionalized trehalose-CL polymer (7 mg) was dissolved in 0.1 M phosphate buffer pH 2.0 (150 µL) and heated to 50° C. for 5 hours. The solution was cooled to room temperature and adjusted to pH 6.0 with 0.2 M $Na_2PO_4$ (45 µL). A solution of 3.3 mg/mL lysozyme in water (98 µg, 30 µL) was added and the conjugation mixed at 4° C. for 30 minutes before a solution of 40 mg/mL $NaCNBH_3$ in water (20 µL) was added. The conjugation was then incubated at 21° C. for 19 hours before the crude mixture was concentrated in 3 kD MWCO centrifugal filter. Crude analysis of conjugation yield was

SUMMARY

Protein-polymer conjugates are an important type of therapeutic biological. However, their chronic use poses concerns due to accumulation and immunogenicity in vivo. Additionally, proteins suffer from instability during storage and transport, increasing patient and clinic costs. These trehalose-caprolactone polymers have been shown to stabilize two important enzymes, lysozyme and β-galactosidase, against heat and lyophilization stresses respectively. Additionally, they have been shown to degrade in basic conditions. Finally, the successful conjugation to lysozyme and a therapeutic growth factor G-CSF has been demonstrated. These materials have the potential to replace PEG as the industry standard for protein-polymer conjugates and overcome previous disadvantages.

Example 2

BMDO Polymers

BACKGROUND

One method toward the synthesis of biodegradable polymers focuses on the introduction of ester moieties in the polymer backbone via radical ring-opening polymerization (RROP). Cyclic ketene acetals (CKAs) are a well-known class of vinyl monomers, which undergo RROP to produce linear polymers containing esters in the backbone. Some examples of CKAs include 5,6-benzo-2-methylene-1,3-dioxepane (BMDO), 2-methylene-1,3-dioxepane (MDO) and 2-methylene-4-phenyl-1,3-dioxolane (MPDL), as well as other monomers with varied ring size and substitution pattern (Agarwal, 2010). These monomers may polymerize with well-known vinyl monomers such as styrene, methyl methacrylate N-isopropylacrylamide (NIPAAm) and vinyl acetate, among others (Agarwal, 2010; Gomez d'Ayala, et al., 2014). These copolymers have been well documented in the literature and the degradation products resulting from hydrolysis of these copolymers have been shown to be non-cytotoxic (Delplace et al., 2013; Siegwart et al., 2008). While degradable glycopolymers containing galactopyranose moieties have been synthesized by this route (Xiao et al., 2011), no stabilization of proteins was shown and no degradable polymers containing trehalose have yet been synthesized.

Growth factors are important therapeutics. For instance, granulocyte colony-stimulating factor (G-CSF) is a protein-drug for stimulating the growth of neutrophils. Cancer patients treated with chemotherapy are at a high risk to develop neutropenia, or abnormally low levels of neutrophils. G-CSF of the PEGylated form Neulasta are typically administered in patients post-chemotherapy to stimulate bone marrow precursors to form neutrophils and to fight against infection. Specifically, it is important to synthesize degradable and stabilizing polymer-protein conjugates for multiple reasons. Protein therapeutics are susceptible to environmental stressors during transit, decreasing their activity ("FDA Access Data"; www.accessdata.fda.gov). Additionally, non-biodegradability potentially causes problems in chronic use because PEG has been shown to accumulate in tissue.

Herein, the synthesis of biodegradable trehalose polymers using radical ring-opening polymerization is described. Two approaches are taken to achieve these polymers, using both copolymerization and post-polymerization techniques.

Synthetic Methods

Synthesis of a Degradable Cyclic Ketene Acetal Monomer

First, BMDO and 2-methylene-4-phenyl-1,3-dioxolane (MPDL) were synthesized using known procedures (Bailey and Wu et al., 1982; Bailey and Ni et al., 1982). Bromoacetaldehyde diethyl acetal and benzene dimethanol were condensed using catalytic p-toluenesulfonic acid (TsOH) to yield the brominated BMDO precursor in 76% yield (Scheme 5a; the numericals of compounds are limited in Example 2). Elimination with potassium tert-butoxide and purification by distillation gave BMDO in 87% yield. Similarly, condensation of styrene glycol and bromoacetaldehyde diethyl acetal with catalytic TsOH led to a mixture of cis and trans brominated products, which were not separated and eliminated to lead to the single MPDL product in 40% yield after distillation (Scheme 5b; the numericals of compounds are limited in Example 2).

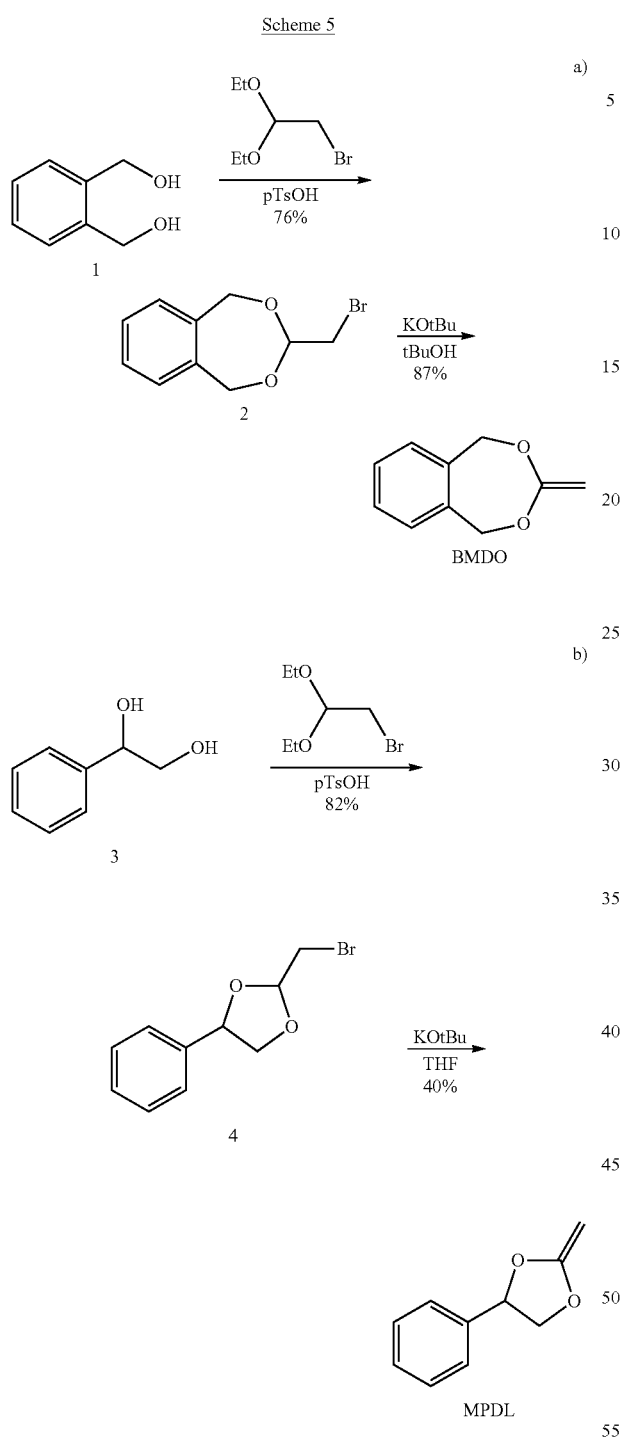
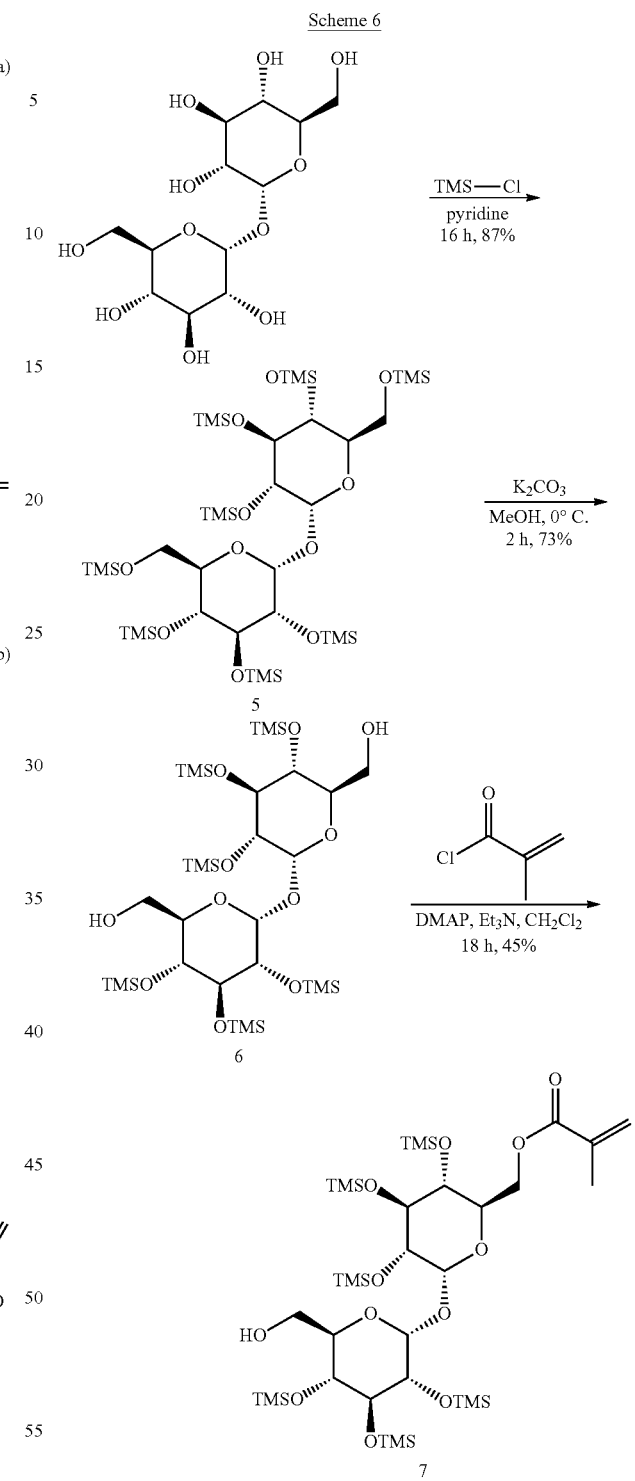

Synthesis of Protected Methacrylate Trehalose Monomer

A three-step procedure was followed to synthesize trimethylsilyl (TMS)-protected methacrylate trehalose monomers (Scheme 6; the numericals of compounds are limited in Example 2). First, trehalose was completely TMS-protected using TMS-Cl in 87% yield, then the primary hydroxyls were selectively removed using mildly basic conditions. Methacryloyl chloride could then be used to install a polymerizable group at one of the free hydroxyls, resulting in TMS-protected monomer 7 in 29% overall yield.

Figure 17:
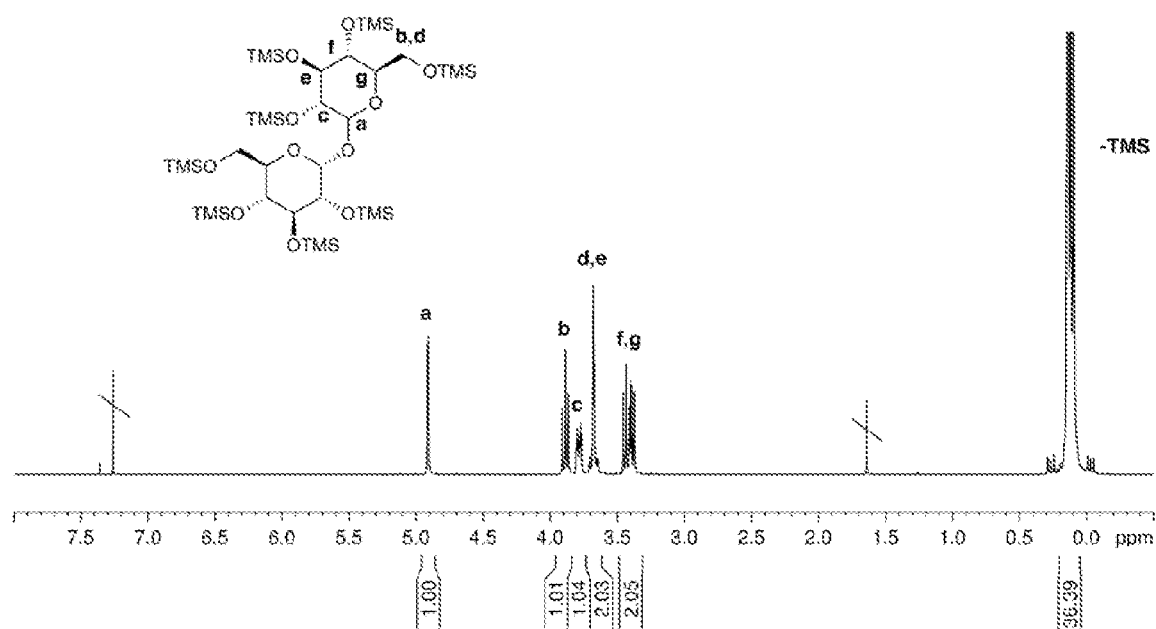
FIG. 17 is a graph showing $^1$H-NMR spectrum (CDCl$_3$) of per-O-(trimethylsilyl)-α,α-trehalose 5.
Figure 18:
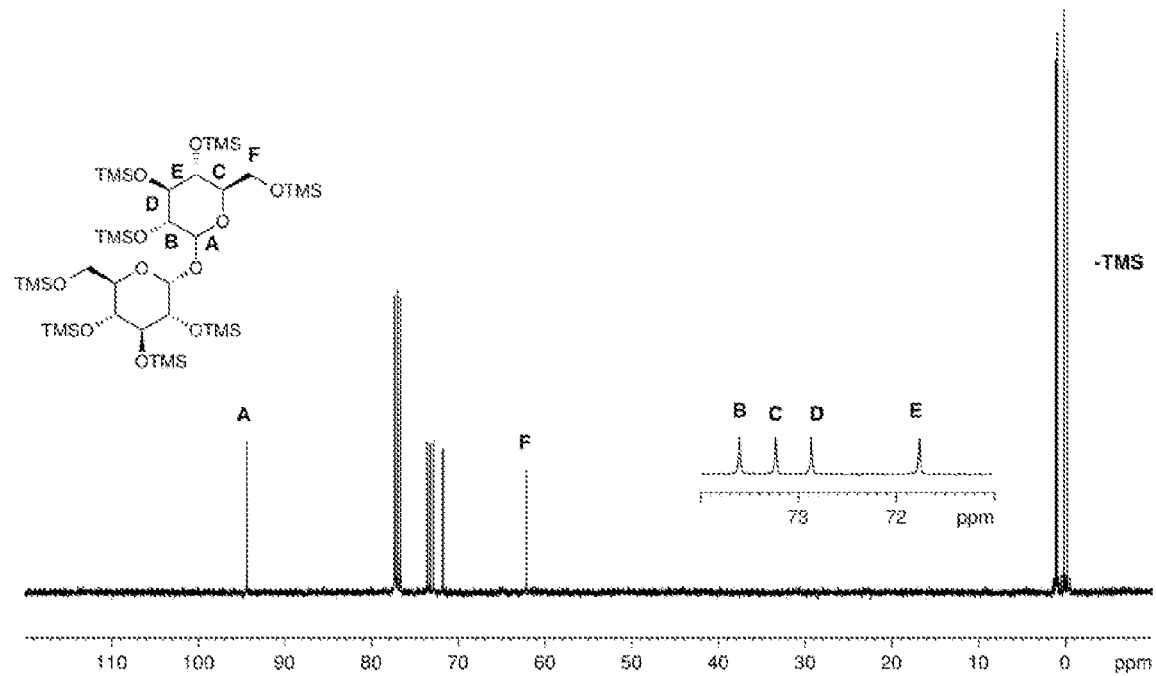
FIG. 18 is a graph showing $^{13}$C-NMR spectrum (CDCl$_3$) of per-O-(trimethylsilyl)-α,α-trehalose 5.

Per-O-(trimethylsilyl)-α,α-trehalose 5: The procedure was adapted from literature (Sizovs et al., 2013). Trehalose (2.0 g, 5.8 mmol) was dissolved in pyridine (50 mL) and let stir 20 minutes until homogeneous. The reaction was cooled to 0° C. and chlorotrimethyl silane (7.11 mL, 56.1 mmol) was added dropwise. The reaction was stirred an additional 30 minutes at 0° C. and warmed to room temperature. After 16 hours, the reaction was cooled again to 0° C. and poured into cold pH 9 carbonate buffer (50 mM, 150 mL). Aqueous workup was performed by extracting with 3×70 mL hexanes. The organic layers were combined and washed with brine (50 mL) then dried over MgSO$_4$. The solvent was removed and the product was freeze-dried from benzene to obtain solid/oil (4.7 g, 5.11 mmol, 87% yield). $^1$H-NMR (400 MHz, CDCl$_3$) δ: 4.91 (d, J=3.2 Hz, 2H), 3.89 (t, J=8.0 Hz, 2H), 3.79 (dt, J=1.4, 9.6 Hz, 2H), 3.68-3.67 (m, 4H), 3.43 (t, J=9.0 Hz, 2H), 3.39 (dd, J=3.2, 9.6 Hz, 2H), 0.14-0.10 (m, 72H). $^{13}$C-NMR (400 MHz, CDCl$_3$) δ=94.4, 73.6, 73.2, 72.9, 71.8, 62.2, 1.2, 0.9, 0.2, −0.3. ESI-MS (MeCN): calculated for C$_{36}$H$_{86}$NaO$_{11}$Si$_8$ [M+Na]$^+$: 941.42, observed: 941.26. FIG. 17 shows $^1$H-NMR spectrum (CDCl$_3$) of per-O-(trimethylsilyl)-α,α-trehalose 5. FIG. 18 shows $^{13}$C-NMR spectrum (CDCl$_3$) of per-O-(trimethylsilyl)-α,α-trehalose 5.

Figure 19:
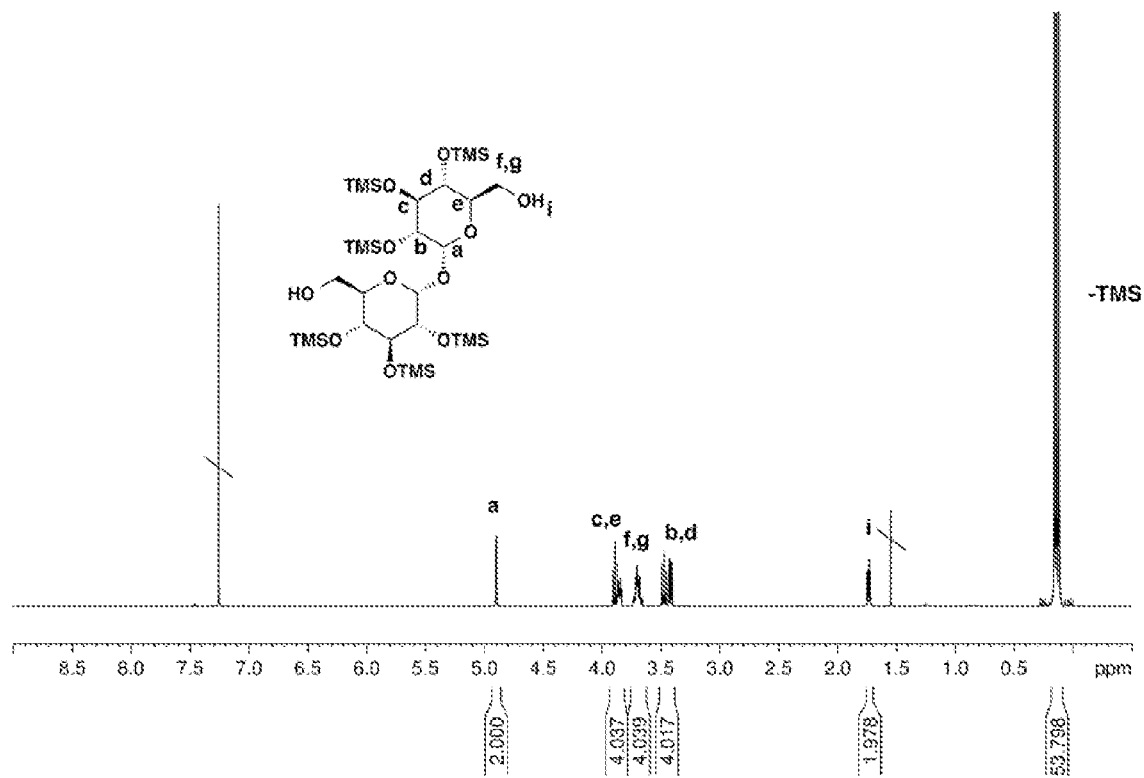
FIG. 19 is a graph showing $^1$H-NMR spectrum (CDCl$_3$) of 2,3,4,2',3',4'-hexakis-O-(trimethylsilyl)-α,α-trehalose 6.
Figure 20:
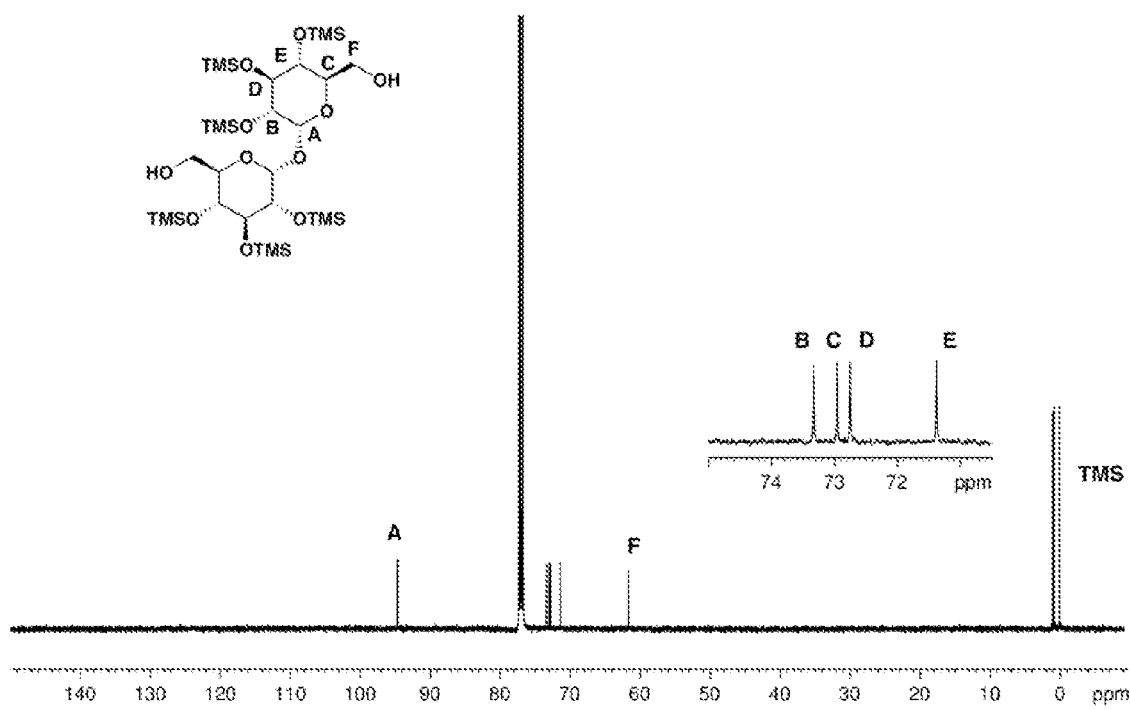
FIG. 20 is a graph showing $^{13}$C-NMR spectrum (CDCl$_3$) of 2,3,4,2',3',4'-hexakis-O-(trimethylsilyl)-α,α-trehalose 6.

2,3,4,2',3',4'-Hexakis-O-(trimethylsilyl)-α,α-trehalose 6. The procedure was adapted from a literature procedure (Johnson, 1992). In a dry, 100 mL round bottom flask under argon, 5 (1.0 g, 1.087 mmol) was dissolved in dry methanol (30 mL) and let stir for 30 minutes to dissolve. The reaction was cooled to 0° C. and a suspension of K$_2$CO$_3$ (150 mg, 1.087 mmol) in methanol (30 mL) was added dropwise over 20 minutes. The reaction was stirred at 0° C. for 2 hours. To quench, glacial acetic acid (0.1 mL) was added to neutralize and methanol was removed by rotary evaporation. The crude was re-dissolved in a combination of hexanes and brine and extracted three times with hexanes. The organic layers were combined, dried with Mg$_2$SO$_4$ and solvent was removed in vacuo. The crude solid was purified by silica gel flash chromatography (4:1 hexane:EtOAc) to yield a white solid (651 mg, 0.839 mmol, 77% yield). $^1$H-NMR (500 MHz, CDCl$_3$): δ: 4.90 (d, 2H), 3.91-3.84 (m, 4H), 3.71-3.68 (m, 4H), 3.47 (t, 2H), 3.41 (dd, 2H), 1.73 (dd, 2H). $^{13}$C-NMR (500 MHz, CDCl$_3$) δ: 94.6, 73.3, 72.9, 72.8, 71.4, 61.7, 1.0, 0.9, 0.0. FIG. 19 shows $^1$H-NMR spectrum (CDCl$_3$) of 2,3,4,2',3',4'-Hexakis-O-(trimethylsilyl)-α,α-trehalose 6. FIG. 20 shows $^{13}$C-NMR spectrum (CDCl$_3$) of 2,3,4,2',3', 4'-Hexakis-O-(trimethylsilyl)-α,α-trehalose 6.

Figure 21:
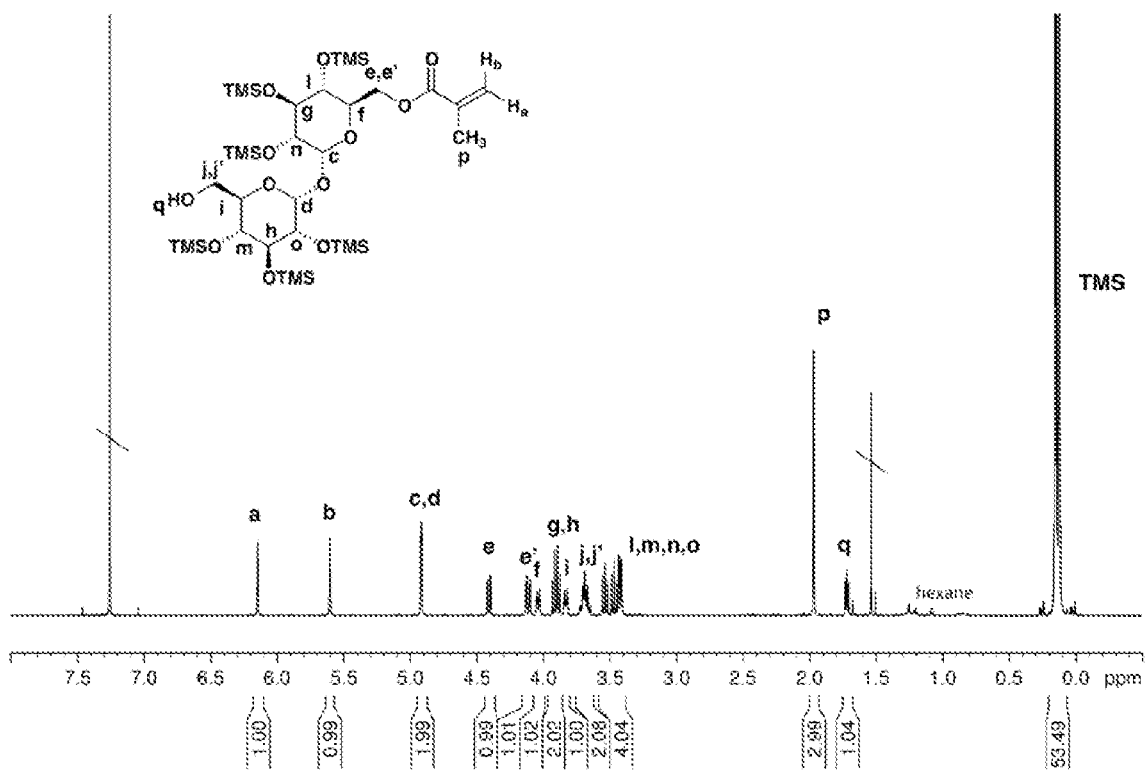
FIG. 21 is a graph showing $^1$H-NMR spectrum (CDCl$_3$) of 2,3,4,2',3',4'-hexakis-O-(trimethylsilyl)-6-O-methacrylate-α,α-trehalose 7.
Figure 22:
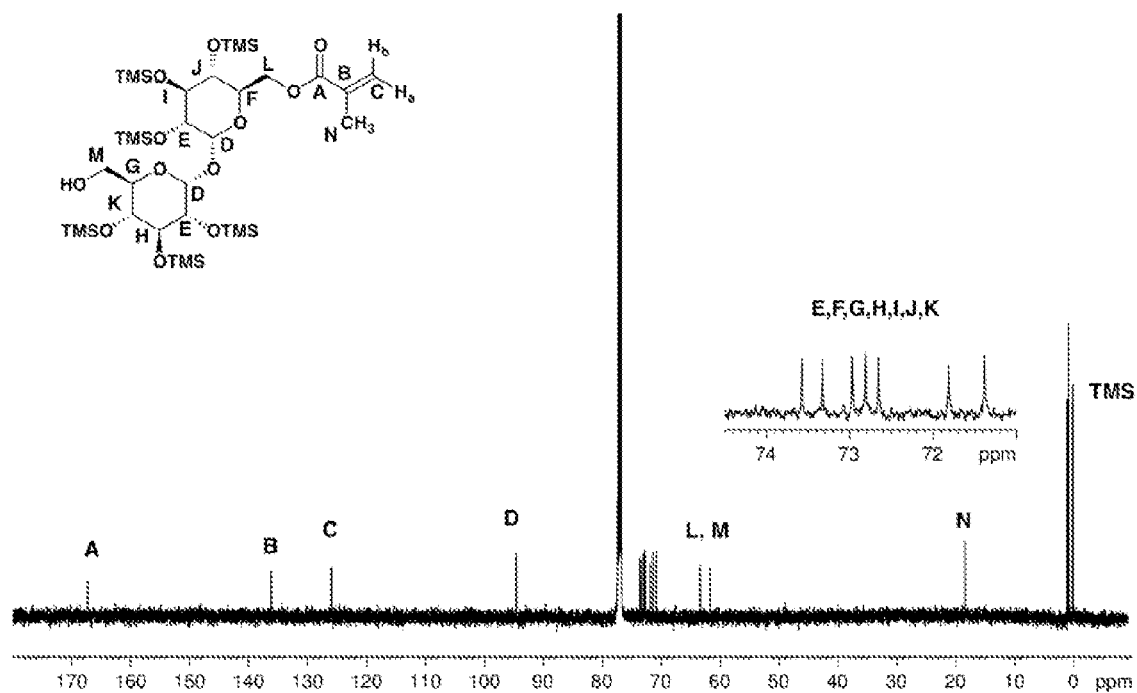
FIG. 22 is a graph showing $^{13}$C-NMR spectrum (CDCl$_3$) of 2,3,4,2',3',4'-hexakis-O-(trimethylsilyl)-6-O-methacrylate-α,α-trehalose 7.

2,3,4,2',3',4'-Hexakis-O-(trimethylsilyl)-6-O-methacrylate-α,α-trehalose 7. In a dry 2-neck 50 mL flask, 6 (2.70 g, 3.49 mmol) was dissolved in 50 mL dry DCM. DMAP (42.6 mg, 0.35 mmol) was added and the reaction was cooled to 0° C. Next, methacryloyl chloride (426 μL, 4.37 mmol) was dissolved in dry DCM (6 mL). The methacryloyl chloride solution and triethylamine (1.83 mL, 10.48 mmol) was added simultaneously dropwise. The mixture was stirred at 0° C. for 30 minutes, then let warm to room temperature. After 16 hours, the reaction was cooled to 0° C. and poured into cold pH 9 carbonate buffer (400 mL). The layers were separated and the aqueous layer was washed twice with hexanes. The organic layers were combined and washed with brine (50 mL), dried with MgSO$_4$ and purified by silica gel flash chromatography (11:2 hexanes:EtOAc eluent) to yield a white solid (1.34 g, 1.59 mmol, 45% yield) $^1$H-NMR (500 MHz, CDCl3) δ: 6.15 (s, 1H), 5.60 (t, J=1.5 Hz, 1H), 4.92 (d, J=1.5 Hz, 2H), 4.41 (dd, J=12.0, 2.4 Hz, 1H), 4.11 (dd, J=12.1, 3.6 Hz, 1H), 4.04 (dt, J=6.8, 2.7 Hz, H), 3.90 (q, J=9.0 Hz, 2H), 3.83 (dt, J=9.4, 3.6 Hz, 1H), 3.73-3.64 (m, 2H), 3.54 (t, J=9.3 Hz, 2H), 3.47 (t, J=9.3 Hz, 1H), 3.42 (ddd, J=9.3, 3.1, 0.8 Hz, 1H), 1.88 (s, 3H), 1.72 (dd, J=7.5, 5.3 Hz, 1H), 0.16-0.12 (m, 54H). $^{13}$C-NMR (500 MHz, CDCl$_3$): δ=167.24, 136.11, 125.89, 94.60, 94.47, 73.57, 73.33, 72.97, 72.81, 72.65, 71.81, 71.38, 70.80, 18.41, 1.079, 1.014, 0.86, 0.85. ESI-MS (MeCN:CHCl$_3$, 9:1): calculated for C$_{34}$H$_{76}$O$_{13}$Si$_6$ [M+NH$_4$]$^+$: 860.41, observed: 860.23. FIG. 21 shows $^1$H-NMR spectrum (CDCl$_3$) of 2,3,4,2',3',4'-Hexakis-O-(trimethylsilyl)-6-O-methacrylate-α,α-trehalose 7. FIG. 22 shows $^{13}$C-NMR spectrum (CDCl$_3$) of 2,3,4,2',3',4'-Hexakis-O-(trimethylsilyl)-6-O-methacrylate-α,α-trehalose 7.

Copolymerization of BMDO Under RAFT Conditions.

The cyclic ketene monomer BMDO was copolymerized using RAFT to obtain well-defined copolymers. Two methods were followed. In one example, a methacrylate comonomer with a reactive handle for later functionalization was used. In another, TMS-protected methacrylate trehalose was directly used for copolymerization.

In the first example, copolymerization of an alkene-functionalized methacrylate monomer with BMDO followed by thiol-ene modification allowed for later installation of the bulky and hydrophilic trehalose moiety. 3-Butenyl methacrylate (bMA) was synthesized following literature procedures; 3-buten-1-ol was treated with methacryloyl chloride in the presence of triethylamine to give bMA in 53% yield (Campos et al., 2008).

Figure 23:
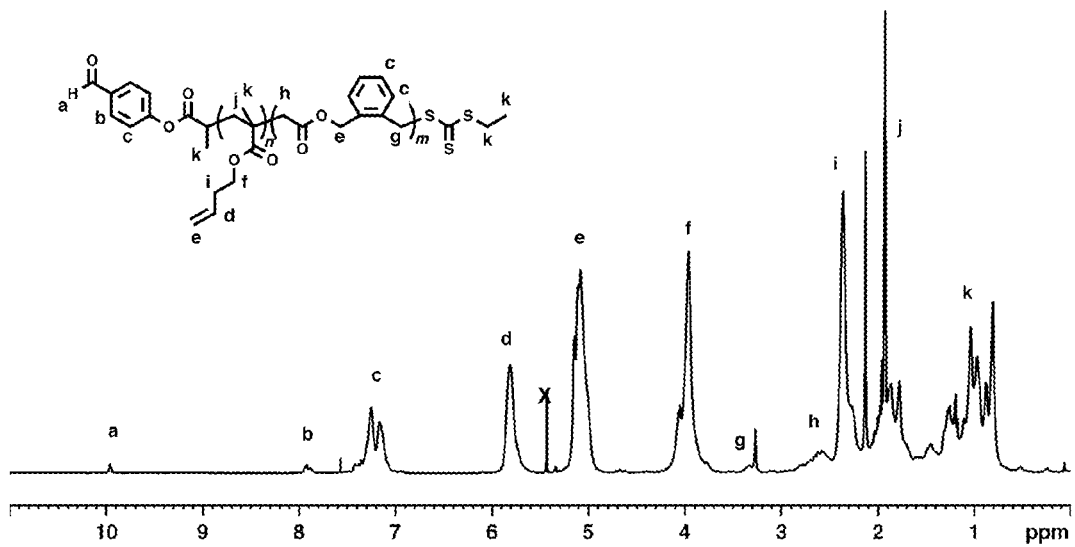
FIG. 23 is a graph showing $^1$H-NMR spectrum (500 MHz, in CD$_3$CN) of BMDO-co-bMA polymer.

BMa and BMDO were then copolymerized using RAFT polymerization (Scheme 7). CKAs are less active monomers than methacrylates and successful incorporation of BMDO into the polymer chain requires a CTA with a slower transfer coefficient, such as a trithiocarbonate. These conditions led to the successful copolymerization of BMDO with bMA (FIG. 23).

Scheme 7

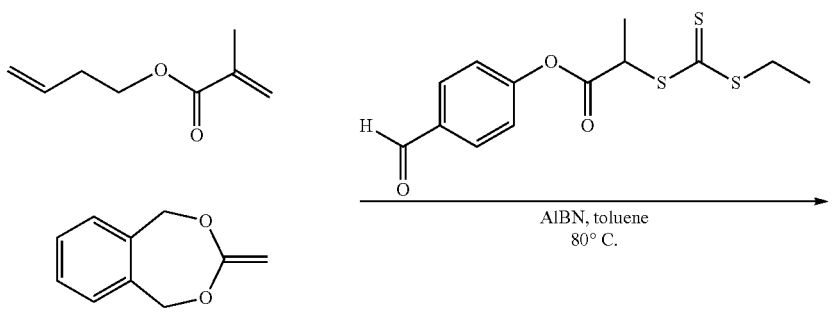

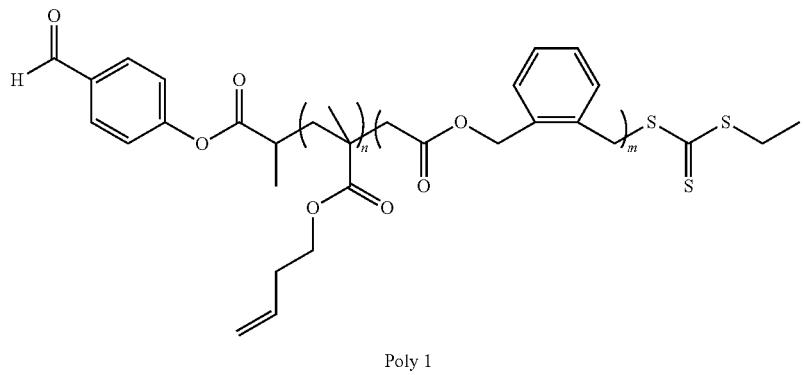

Poly 1

While the differing monomer reactivities led to low BMDO incorporation in the RAFT copolymer, this is advantageous in the synthesis of a biodegradable trehalose polymer. The majority of the polymer should consist of trehalose units to maintain stabilizing ability. The DMF solvent peak prevented accurate GPC measurement, but the mismatch between CTA and methacrylate monomer required for copolymerization would be expected to result in a broad Đ, typical for improperly controlled BMDO-methacrylate copolymerizations (Decker and Maynard, 2015).

Next, the allyl-functionalized polymer was used as a substrate for a thiol-ene reaction with thiolated trehalose, synthesized as described above.

Scheme 8.

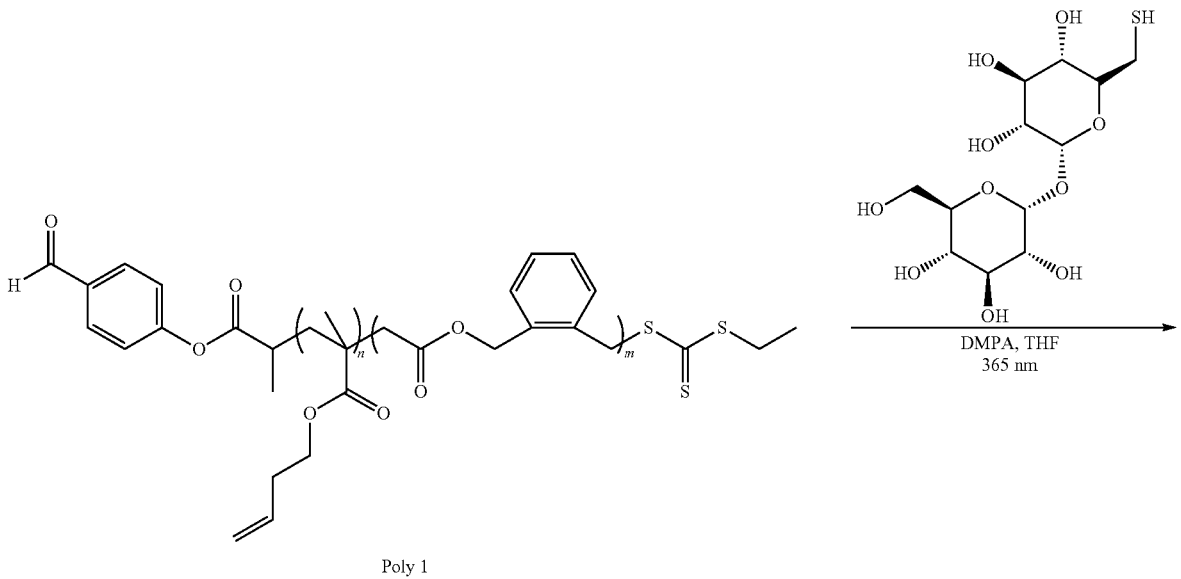

Poly 1

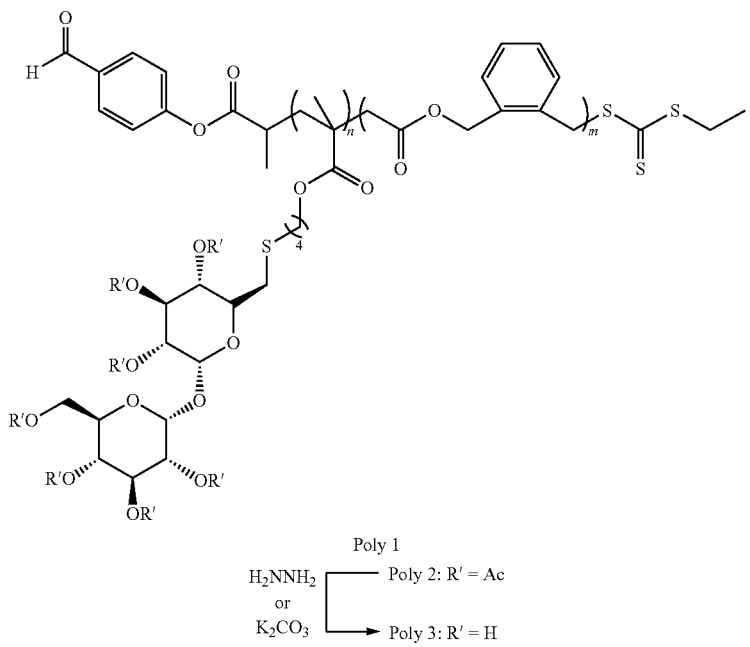

Poly 1

H₂NNH₂ or K₂CO₃ → Poly 2: R' = Ac
→ Poly 3: R' = H

Figure 24:
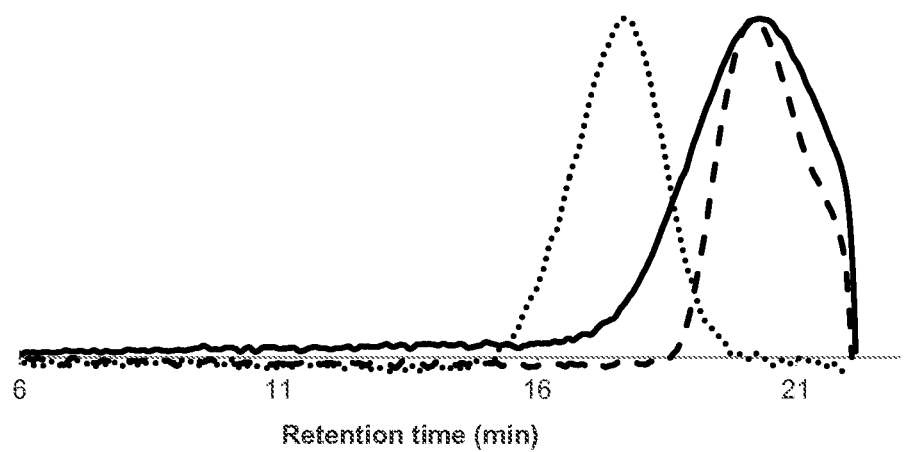
FIG. 24 is a graph showing Gel permeation chromatogram of Poly 1-3. Orange: Poly1(poly(BMDO-co-bMA); Blue: Poly2 (poly(BMDO-co-acetate trehalose MA); Green: Poly3 (poly(BMDO-co-trehalose MA).

The successful modification could be followed by gel permeation chromatography (GPC) to ensure that no cleavage of the backbone esters was occurring (FIG. 24).

In the second example, the trehalose-containing methacrylate monomer 4 was directly employed (Scheme 9). Because methyl methacrylate shows a greater tendency to copolymerize with BMDO than styrene, a methacrylate-based trehalose monomer was chosen. Additionally, an amide-containing pyridyl disulfide CTA was used to minimize end-group cleavage during the acidic TMS deprotection.

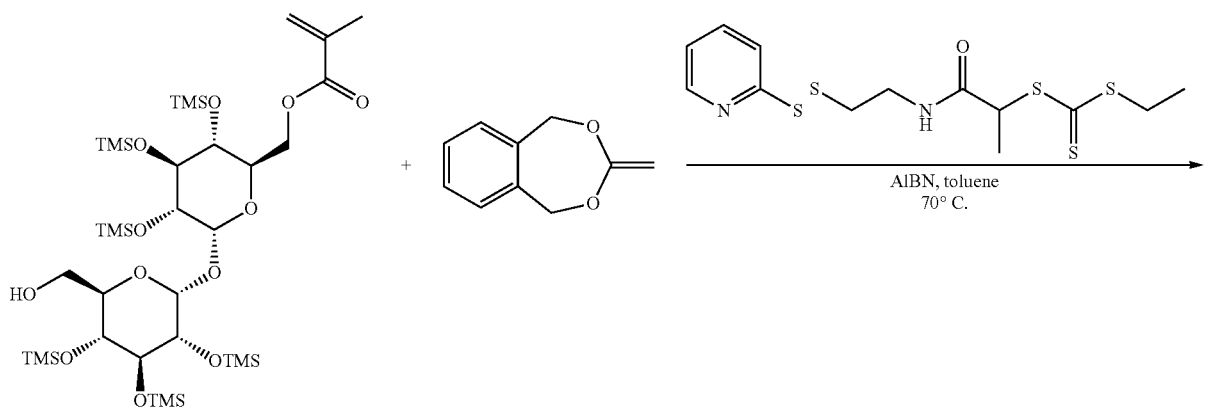

Scheme 9.

-continued

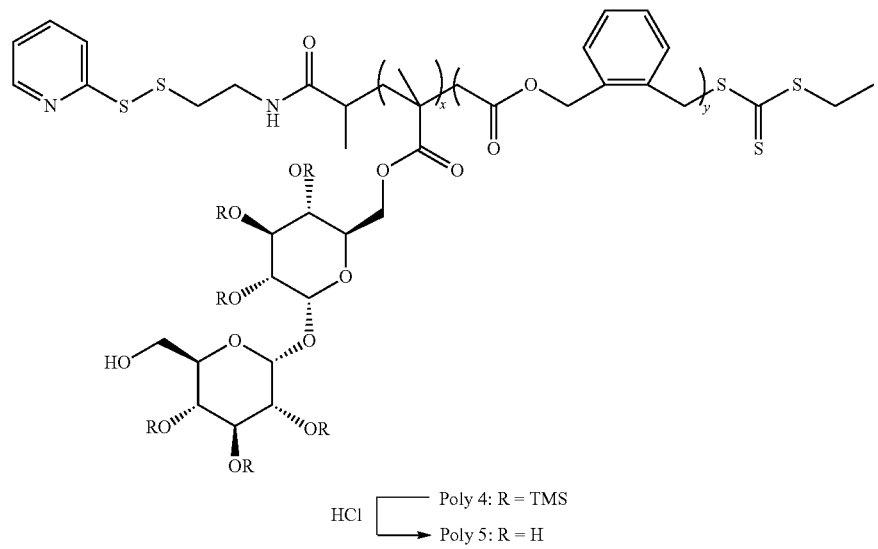

Poly 4: R = TMS
HCl
Poly 5: R = H

Figure 25:
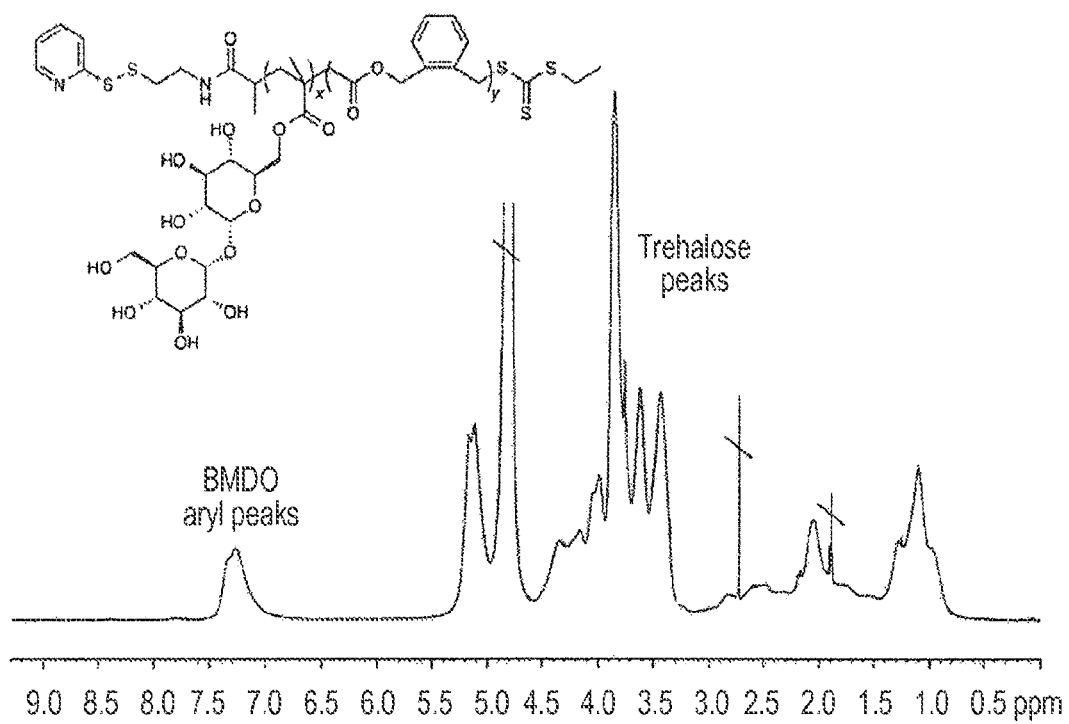
FIG. 25 is a graph showing $^1$H-NMR of trehalose-BMDO copolymer Poly5 showing BMDO aryl peaks and trehalose peaks.

This polymerization was successful and resulted in BMDO incorporation. The $^1$H NMR showed the presence of aryl peaks in the final purified polymer confirming the successful copolymerization of BMDO with the trehalose methacrylate monomer (FIG. 25). BMDO incorporation was calculated to be 28% by comparing the integration of the aryl region at 7.0-7.5 ppm with the trehalose peaks at 3.2-4.5 ppm.

Figure 26:
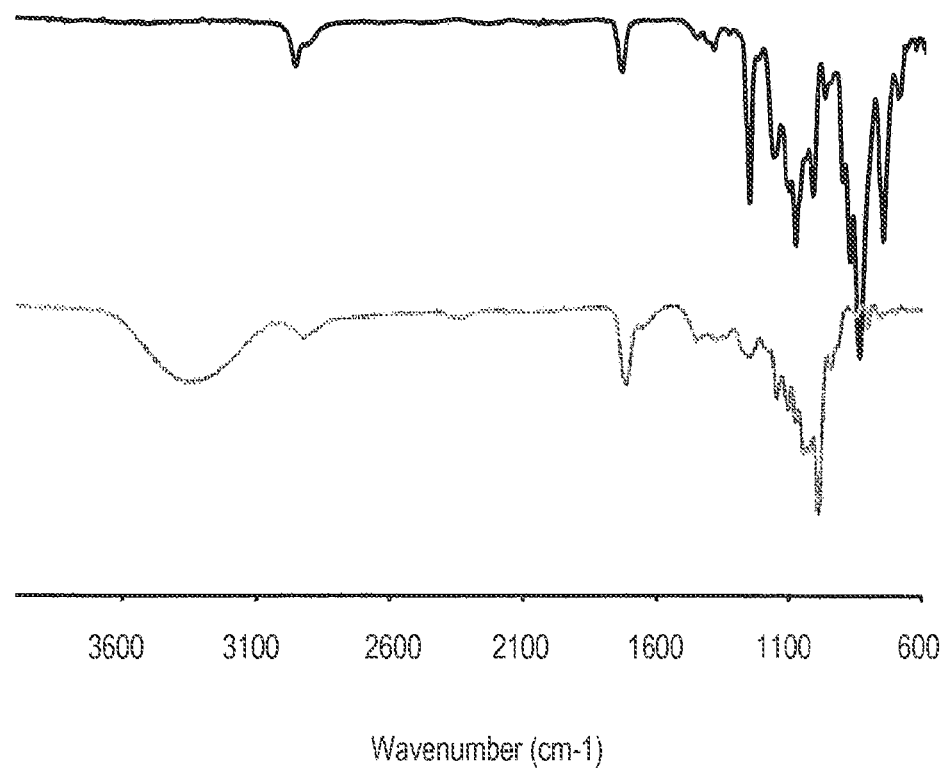
FIG. 26 is a graph showing differences in IR spectra of trehalose-BMDO copolymer Poly4-5 before (black, above) and after (gray, below) removal of TMS protecting groups.

The labile TMS groups were then easily cleaved with dilute acid, as confirmed by infrared spectroscopy (FIG. 26). After deprotection, a broad peak at 3370 cm$^{-1}$ appeared, corresponding to free hydroxyl groups.

Figure 27:
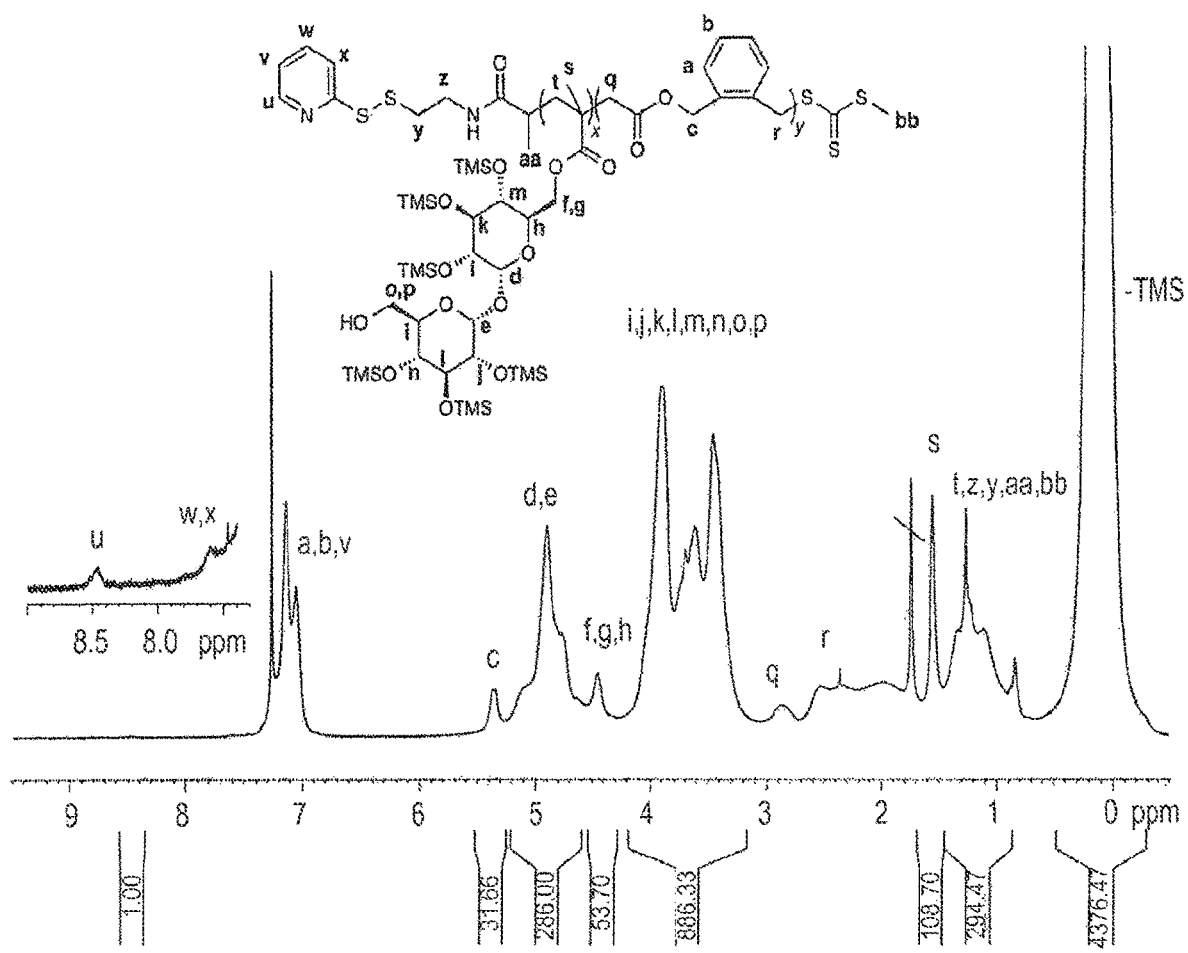
FIG. 27 is a graph showing $^1$H-NMR spectrum (CDCl$_3$) of TMS-trehalose-BMDO copolymer Poly4.
Figure 28:
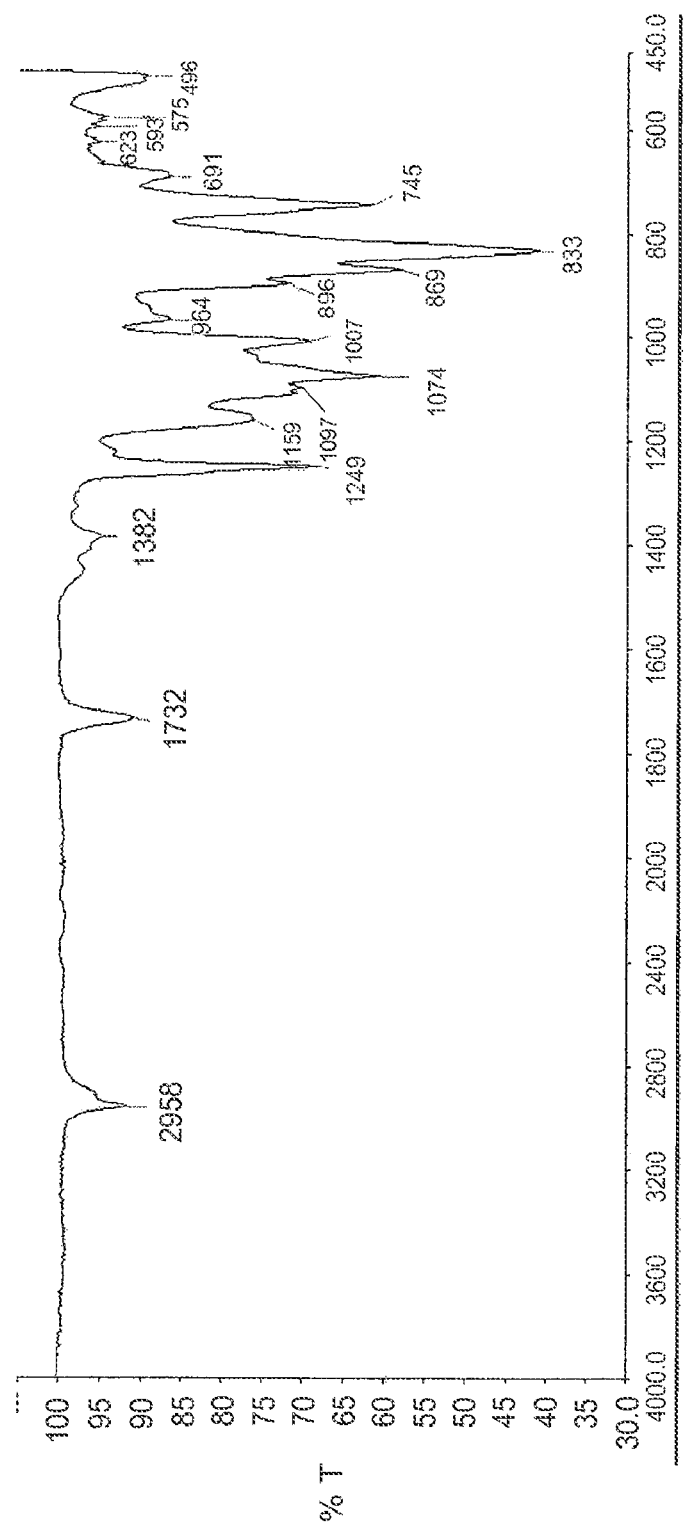
FIG. 28 is a graph showing IR spectrum (neat) of TMS-trehalose-BMDO copolymer Poly4.

Copolymerization of BMDO and 4 under RAFT conditions. In a dry Schlenk flask, 4 (100 mg, 0.12 mmol) was dissolved in dry toluene (80 μL). Then both 9 μL of a stock solution of AIBN (2.8 mg in 500μL dry toluene) and 15 μL of a stock solution of CTA (2.4 mg in 60 μL dry toluene) were added. BMDO (19.2 mg, 0.12 mmol) was dissolved in toluene (46μL) and transferred to the Schlenk tube. The Schlenk tube was subjected to five freeze-pump-thaw cycles, until the pressure remained constant at 160 mTorr, then the tube was backfilled with argon and heated to 70° C. After 18 hours, the polymerization was quenched by exposure to oxygen followed by immersion in liquid nitrogen. Percent conversion was assessed by $^1$H-NMR of the crude reaction mixture, which was then purified by precipitating three times from dichloromethane (0.5 mL) into cold methanol (50 mL) to yield a white solid (69.2 mg, 11.6 nmol, 74% recovery). $^1$H-NMR (500 MHz, CDCl$_3$) δ: 8.56-8.42 (s, 1H), 7.68-6.86 (m, 221H), 5.52-5.26 (s, 32H), 5.26-4.55 (m, 286H), 4.56-4.25 (s, 54H), 4.25-3.18 (m, 886H), 3.07-2.70 (s, 44H), 2.70-1.82 (m, 224H), 1.64-1.45 (s, 108H), 1.45-0.91 (m, 294H), 0.47-0.28 (s, 4376H). FT-IR (cm$^{-1}$): 2958, 1732, 1382, 1249, 1159, 1097, 1074, 1007, 964, 896, 869, 833, 745. FIG. 27 shows $^1$H-NMR spectrum (CDCl$_3$) of TMS-trehalose-BMDO copolymer Poly4. FIG. 28 shows IR spectrum (neat) of TMS-trehalose-BMDO copolymer Poly4.

Figure 29:
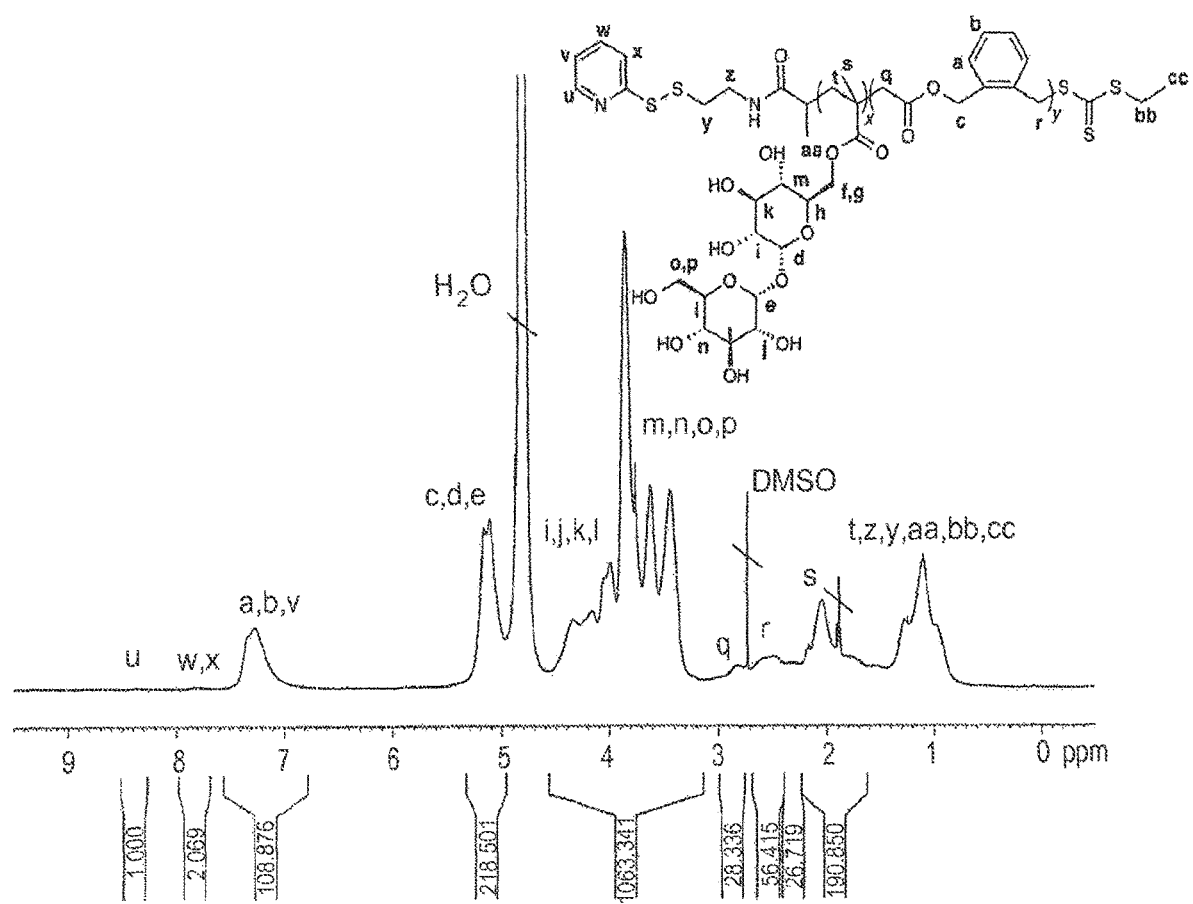
FIG. 29 is a graph showing $^1$H-NMR spectrum (D$_2$O) of trehalose-BMDO copolymer Poly5.
Figure 30:
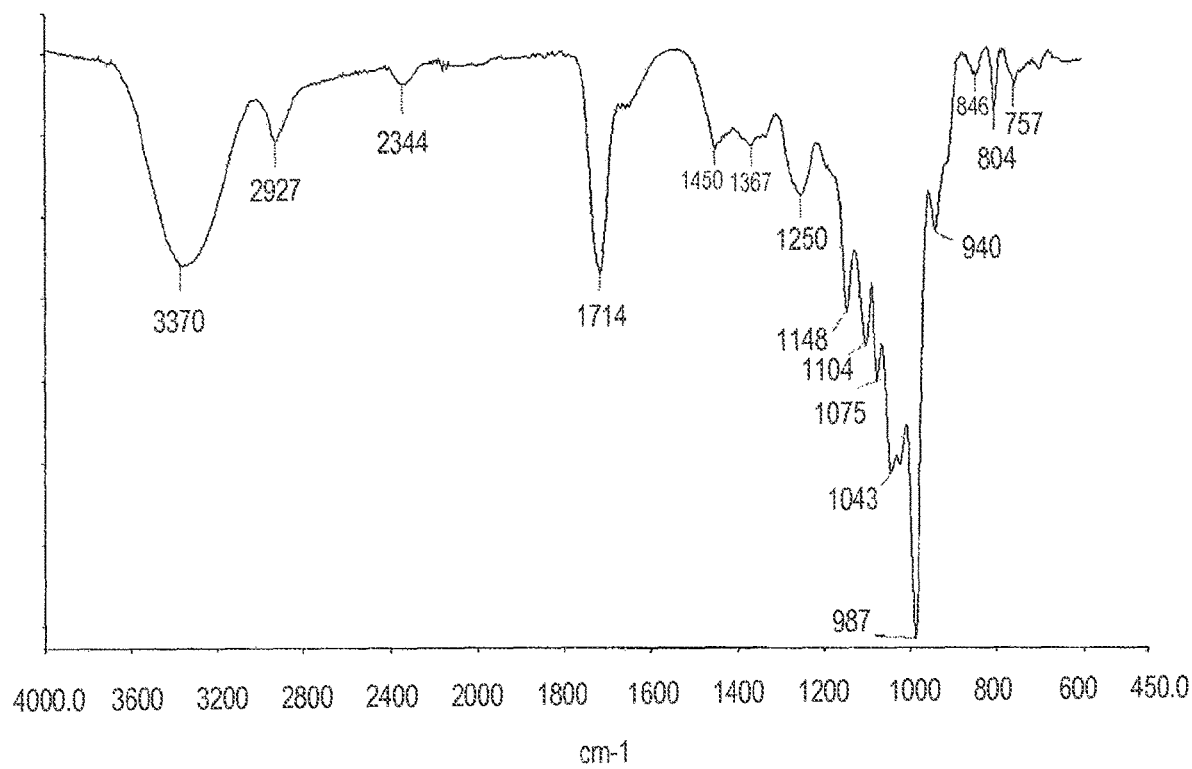
FIG. 30 is a graph showing IR spectrum (neat) of trehalose-BMDO copolymer Poly5.

Removal of TMS groups. In a 20 mL scintillation vial, poly(TMS-protected trehalose-co-BMDO) (69 mg) was dissolved in 5:1 THF:MeOH (6 mL) and 1M HCl (0.15 mL) was added. The vial was vortexed and within 3 minutes a white precipitate began to form. The vial was let stand for 10 minutes, then transferred to a falcon tube and centrifuged for 10 minutes. The resulting precipitate was washed three times with 5:1THF:MeOH (6 mL). After the third time, the precipitate was dissolved in 1:1 H$_2$O:MeOH (2 mL) and ultracentrifugation was performed in a 15 mL tube with 3 kD molecular weight cutoff. The polymer was washed once with H$_2$O:MeOH and once with H$_2$O, then lyophilized to remove water to yield a white fluffy solid (32.4 mg, 11.2 mmol, 96% recovery). $^1$H-NMR (500 MHz, D$_2$O) δ: 8.48-8.27 (s, 1H), 7.98-7.69 (s, 2H), 7.56-6.78 (d, 108H), 5.34-4.96 (d, 218H), 4.57-3.14 (m, 1064H), 2.99-2.75 (s, 28H), 2.69-2.40 (m, 56H), 2.40-2.24 (s, 26H), 2.24-1.63 (m, 190H), 1.63-1.46 (s, 24H), 1.43-0.77 (t, 262H). FT-IR (cm$^{-1}$): 3370, 2927, 2344, 1714, 1450, 1367, 1250, 1148, 1104, 1075, 1043, 987, 940. FIG. 29 shows $^1$H-NMR spectrum (D$_2$O) of trehalose-BMDO copolymer Poly5. FIG. 30 shows IR spectrum (neat) of trehalose-BMDO copolymer Poly5.

Stabilization of Proteins Using Degradable BMDO-Containing Polymers as Excipients The polymer modified by thiol-ene chemistry (Poly 3) and the polymer formed by direct copolymerization (Poly 5) were assessed for their ability to stabilize proteins as excipients.

Figure 31:
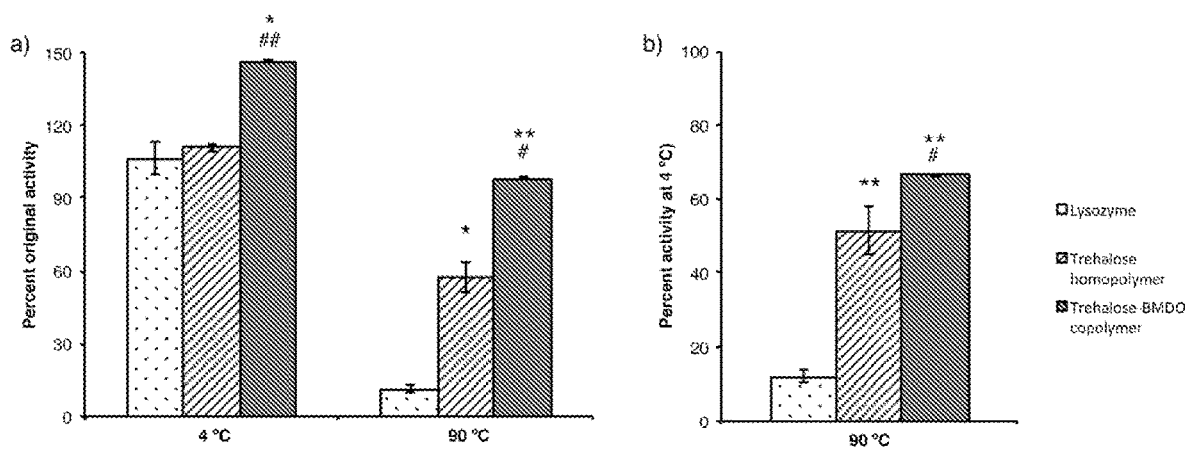
FIG. 31 (a and b) is a set of graphs showing a) activity of lysozyme before and after heating at 90° C. for 20 minutes with trehalose homo- and copolymers as excipients (100 wt eq relative to lysozyme) and b) activity of lysozyme after heat stress with the addition of trehalose homo- and copolymers as excipients, presented as the activity with respect to the original activity of the excipient mixture at 4° C. *=p<0.01, **=p<0.001 in comparison to no additive. #=p<0.01, ##=p<0.001 in comparison to trehalose homopolymer.

In the second example (Poly 5), the resulting deprotected copolymer was then tested for its ability to stabilize proteins against heat stress (FIG. 31) and compared to a methacrylate trehalose hompolymer (i.e. polymer without BMDO) and to no additive. Specifically, model protein lysozyme was stressed at 90° C. for 20 minutes and its bioactivity was reduced to 12% of its original activity when no polymer was added.

The trehalose-BMDO copolymer retained 97% lysozyme activity, while the trehalose homopolymer only stabilized lysozyme to 57% of original activity (FIG. 31a). These data indicate that the incorporation of BMDO into the backbone of the trehalose glycopolymer does not adversely affect the polymer's ability to stabilize proteins. In fact, dilution of the trehalose results in a polymer that is a more effective stabilizer of lysozyme. It is known in other systems that diluting sugar moieties along a polymer backbone can lead to increased biological activity (Wada et al., 2011; Kanai et al., 1997; Gestwicki et al., 2002; Ladmiral et al., 2006)).

In addition to stabilizing lysozyme against heat stress at 90° C., samples with the copolymer as excipient demonstrated increased activity at 4° C. compared to lysozyme alone. This increase has been previously observed for the stabilization of glucose oxidase (GOx) with monomeric trehalose and is thought to be due to the sugar enhancing or stabilizing protein-substrate interactions (Paz-Alfaro et al., 2009). We have ruled out that the polymer itself is a substrate for the assay. Therefore the activity was also presented with respect to the activity of the excipient mixture at 4° C. (FIG. 31b). Represented in this manner, the activity was decreased after heat stress in all cases; yet the trehalose-BMDO copolymers were still statistically better stabilizers (67% activity) than no additive (12% activity) or the homopolymer (51% activity) as shown in FIG. 31b.

Heat stress of lysozme with trehalose-BMDO copolymer. A 0.1 mg/mL lysozyme stock in phosphate buffered saline (PBS) pH 7.4 was prepared and mixed with trehalose-BMDO copolymer (100 eq relative to lysozyme) or methacrylate trehalose homopolymer (100 eq relative to lysozyme). Samples were further diluted to a concentration of 0.021 mg/mL (1 kU/mL) and 20 µL aliquots were prepared in 0.5 mL LoBind Eppendorf tubes. Each aliquot was heated to 90° C. for 20 minutes at 500 rpm, then cooled to 4° C. and centrifuged for 1 minute at 10,000 rpm. Samples were stored at 4° C. until activity was evaluated all together using the EnzChek® lysozyme activity assay.

Lysozyme activity assay (EnzChek®). Aliquots containing 20 µL of lysozyme-glycopolymer solution were diluted to 100 µL with PBS pH 7.4, 50 µL of the resulting solution was removed and incubated with 50 µL of *Micrococcus luteus* labeled with FITC (1 mg/mL) at 37° C. for 30 minutes in a 96-well plate. The resulting fluorescence was measured (abs 480 nm/em 530 nm) and quantified relative to a known concentration curve. Statistics to determine significance were calculated using the Students t test; % confidence as $+/-=t(\text{standard deviation})/(\text{number of trials})^{1/2}$ with $p<1-\%$ confidence/100.

Degradation of Degradable BMDO-Containing Polymers in Basic Conditions

Figure 32:
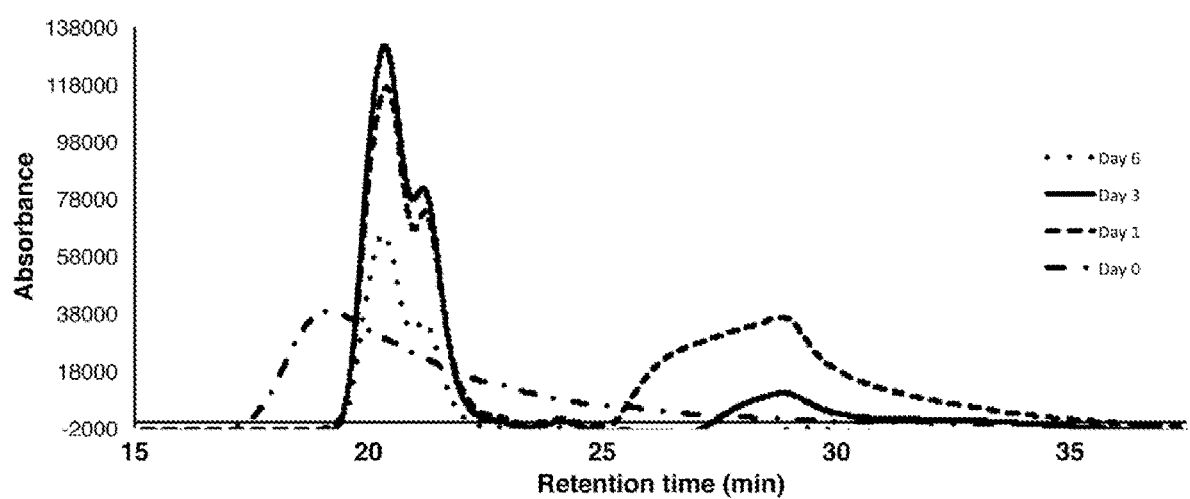
FIG. 32 is a graph showing degradation of trehalose-BMDO copolymer Poly5 in 5% KOH, monitored by gel permeation chromatography (GPC).

Both Poly 3 and Poly 5 were assessed for their ability to degrade under basic conditions. First, Poly 5 was treated with 5% KOH and the molecular weight assessed at intervals between 1 to 5 days. After 1 day, the gel permeation chromatogram showed a significant decrease in molecular weight, with no further change after subsequent days suggesting that the polymer was fully degraded (FIG. 32). In addition, the GPC trace of the degradation products was bimodal, indicating that not all the fragments were the same molecular weight. This would be expected for a random copolymer where degradable units would be placed randomly along the polymer background.

Figure 33:
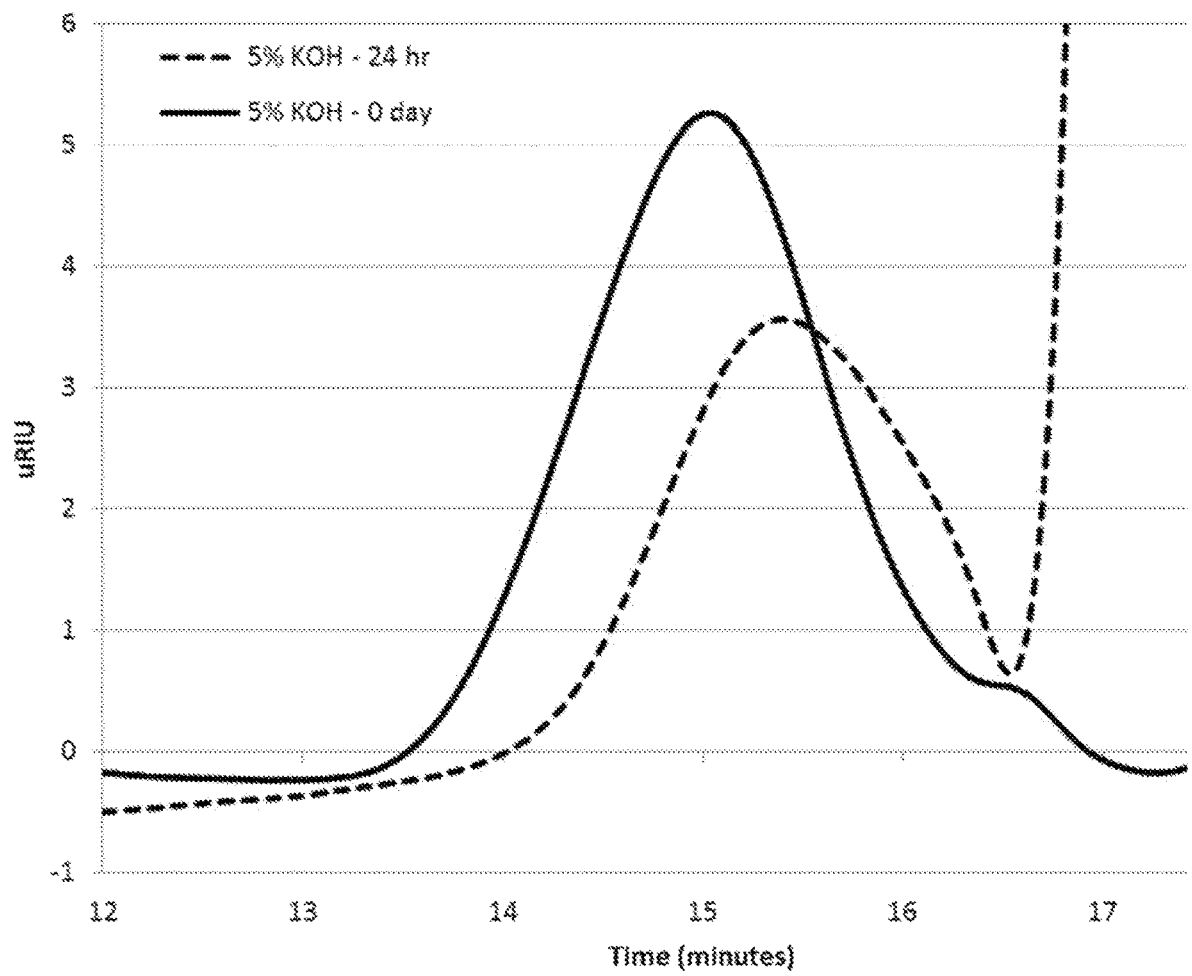
FIG. 33 is a graph showing degradation of Poly3 in 5% KOH.

BMDO-trehalose polymer was dissolved in a 5% KOH solution. Samples were lyophilized, dissolved in the GPC mobile phase, neutralized with HCl, and then analyzed by GPC (FIG. 33).

Degradation of copolymers under basic conditions. Trehalose-BMDO copolymer (5 mg) was dissolved in 1.00 mL 5% KOH. The solution was vortexed and placed on Thermoshaker at 23° C. and 1000 rpm. Aliquots (200 µL) were removed and lyophilized at 1, 3, and 5 days.

Scheme 10

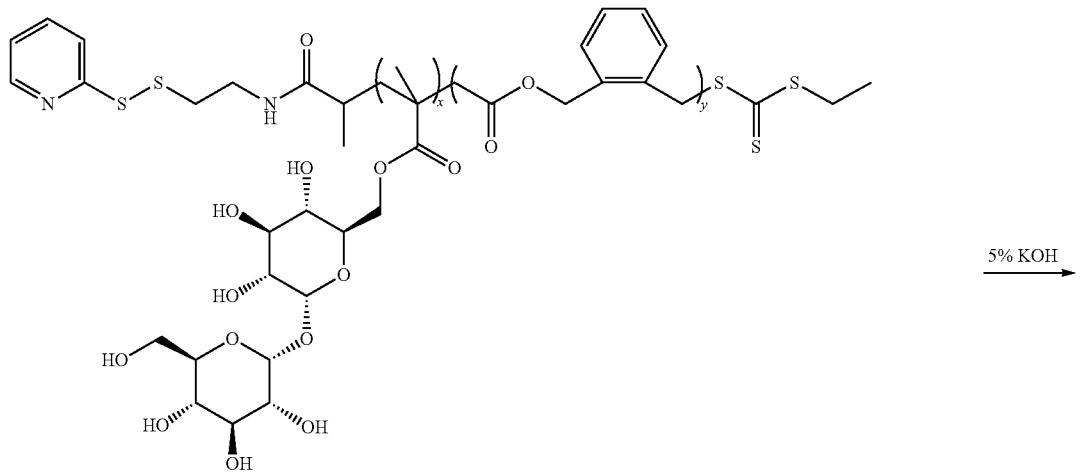

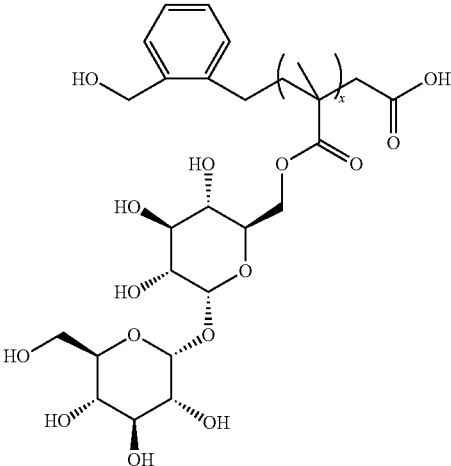

Figure 34:
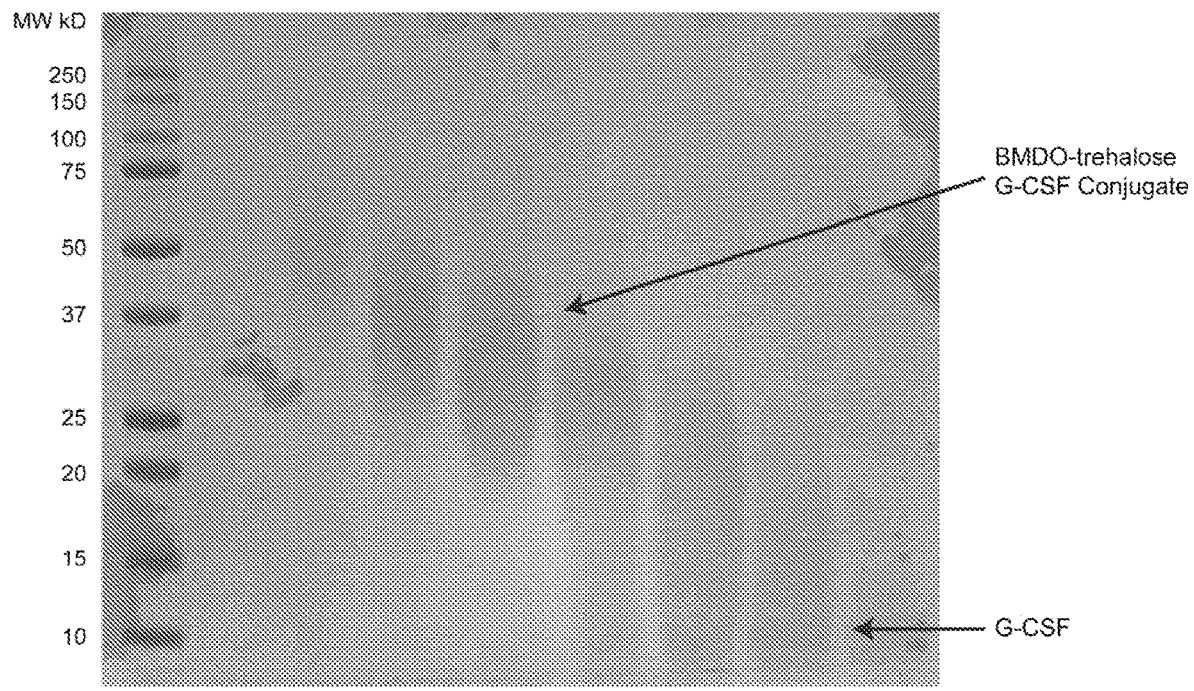
FIG. 34 is a photograph showing SDS-PAGE of FPLC fractions of BMDO-trehalose polymer G-CSF conjugation. Each lane is a successive fraction.

Conjugation of Degradable BMDO-Containing Polymers to G-CSF, a Therapeutic Protein BMDO-trehalose polymer conjugated to G-CSF was made using reductive amination targeting the N-terminal methionine residue of the G-CSF protein. Recombinant human G-CSF (200 μg, 10.6 nmol) was diluted into pH 5.0, 100 mM sodium acetate buffer. BMDO-trehalose polymer (15 mg, 1.07 μmol) and sodium cyanoborohydride (3.84 mg, 61.1 μmol) was added. The conjugation reaction was incubated at 4° C. for 72 hours. The pH was adjusted to 4.0 by the addition of 100 mM HCl and the crude mixture analyzed by SDS-PAGE. The conjugate was then purified by FPLC for separation of free polymer and unconjugated protein (FIG. 34).

In summary, two methods of synthesizing biodegradable trehalose polymers containing BMDO units by RAFT polymerization are presented. The polymers are made by polymerization of a protected monomer or by post-polymerization modification of polymers with reactive pendant units. These polymers were shown to stabilize model proteins as excipients, and to degrade in basic conditions. Additionally, the conjugation to G-CSF as a therapeutic protein was also demonstrated. These conjugates are useful for continuous therapy to impart stabilization without unnecessary accumulation of polymer.

Figure 36:
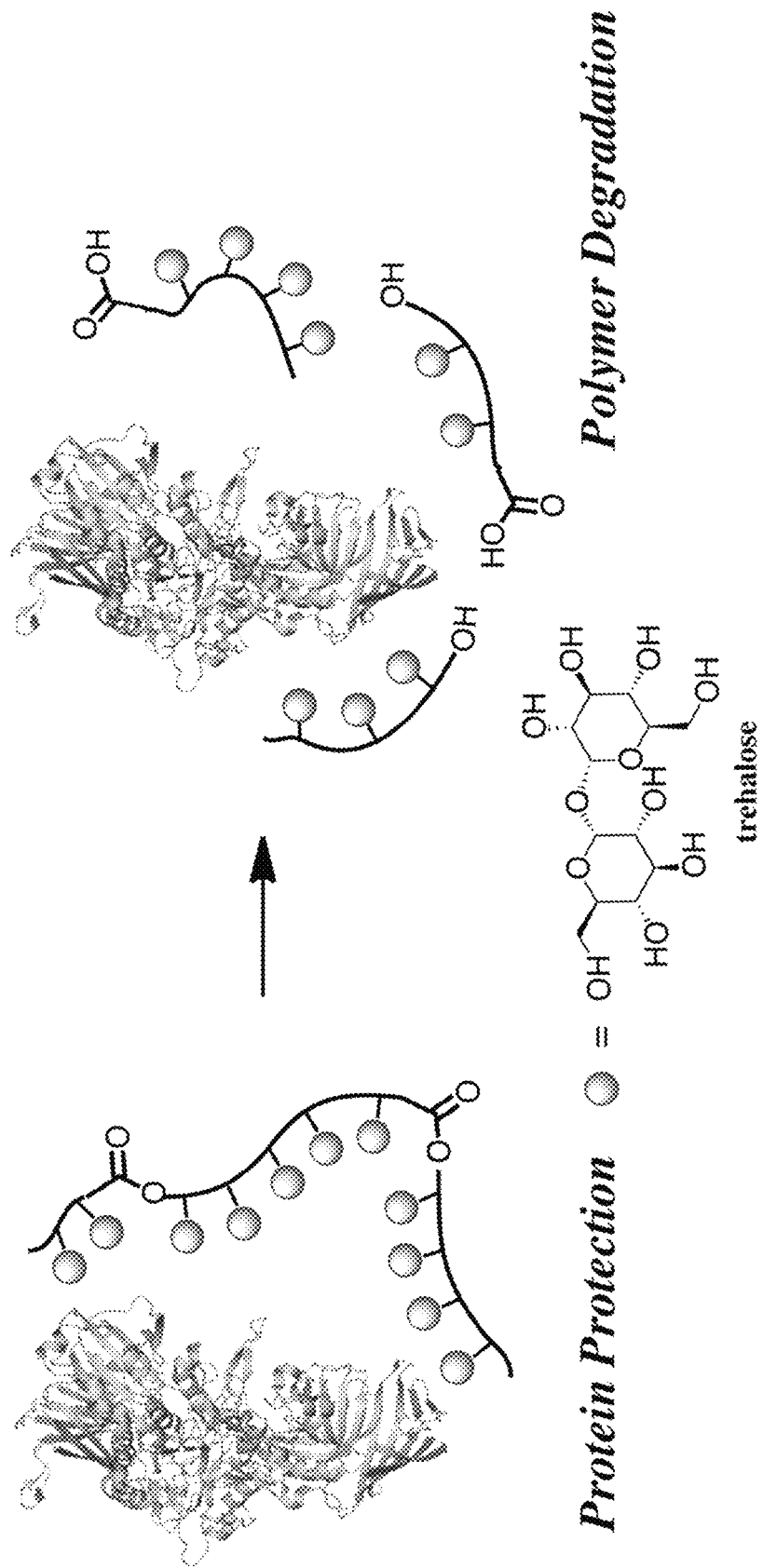
FIG. 36 is a drawings of Scheme 11.

We propose synthesizing trehalose glycopolymers that stabilize proteins and other biomolecules to the lyophilization process and also can be degraded through ester hydrolysis (Scheme 11, FIG. 36).

Hypothetical Example 3

The covalent attachment of poly(ethylene glycol)(PEG)-based polymers is known to improve the pharmacokinetics of protein therapeutics through stabilization and improved circulation time (Knop et al., 2010). There are several FDA-approved, PEGylated therapeutic agents on the market (Alconcel et al., 2011). In addition, protein conjugation to branched PEG-like polymers, such as poly(ethylene glycol methyl ether methacrylate) (PEGMA), developed by controlled radical polymerization (CRP) have been shown to improve pharmacokinetics as compared to PEGylation (Gao et al., 2010). Despite these advantages, PEGylation can result in decreased activity of the protein (Robert and Milton, 1998) and long-term treatment with PEGylated therapeutics can result in accumulation in the liver and spleen, hypersensitivity, the development of anti-PEG IgM antibodies, and lysozomal disease syndrome (Markovsky et al., 2012). Therefore, PEG-like polymers, containing a degradable linkage and/or degradable moieties in the backbone, have been sought-after to circumvent these issues (Duro-Castano et al., 2014).

Degradable linkages at the site of attachment between the polymer and protein are often installed so that the protein can be released (hydrolytically, enzymatically, or reductively) from the polymer in-vivo, and thus regain activity (Roberts et al., 2002). Such linkages include maleylamino peptide bonds (Garman and Barret, 1987), carbamate (Veronese et al., 1985), ester (Abuchowski et al., 1985), disulfide (Woghiren et al., 1993), hydrazone (Zalipsky and Menon-Rudolph, 1997), and oxime (Gaertner and Offord, 1996) bonds. For instance, PEG-Intron® was designed with a degradable carbamate linkage to interferon alpha-2b (Kozlowski and Milton, 2001). Roberts and Harris reported PEGylation of lysozyme (Lyz) through a degradable ester linkage; upon hydrolysis of the ester, the activity of Lyz was regained to 60% native activity (Roberts and Harris, 1998). However, the PEG backbone is non-degradable, and thus negative effects associated with polymer accumulation persist. To prevent this accumulation, enzymatically or hydrolytically degradable moieties such as esters (Iha et al., 2010), vinyl ethers (Lundberg et al., 2012), acetals (Dingels et al., 2013), oximes, or urethanes (Yan-Ling et al., 2010), as well as reduction sensitive disulfides (Cerritelli et al., 2007) have been installed in the backbone of PEG. Main-chain degradable PEGs have not yet been conjugated to a protein therapeutic. Several backbone degradable polymer-protein conjugates have been developed. Most of these conjugates consist of sugar-based or sugar-derived polymers such as hydroxyethyl starch (Hey et al., 2012), polysialic acid (Zhang et al., 2010), dextran (Yurkovetskiy et al., 2005) or dextrin (Hardwicke et al., 2008). Recently, ring opening polymerization has been used to synthesize a poly(ε-caprolactone) which was covalently bound to bovine serum albumin (Liu et al., 2014).

CRP offers easy end-group functionalization, well-defined polymer molecular weights, and compatibility with a wide variety of monomers. Therefore, much attention has been paid to the development of CRP techniques as a means to develop well-defined, PEG-like polymer-protein therapeutics (Grover and Maynard, 2010). The backbones of such PEG-like polymers have also been modified with degradable linkages through the coupling of radical ring-opening polymerization (rROP) of cyclic ketene acetals (CKAs) with CRP techniques including atom transfer radical polymerization (ATRP) (Lutz et al., 2007; Riachi et al., 2009) and nitroxide mediated polymerization (NMP)(Delplace et al., 2013). While CKAs have also been polymerized by reversible addition-fragmentation chain-transfer (RAFT) polymerization and macromolecular design via interchange of xanthates (MADIX) as a means of installing degradable units into polymer backbones, these techniques have not yet been applied to PEG-like polymers (Hedir et al., 2014; Siegwart et al., 2008; Kobben et al., 2014). In addition, no degradable polymer, developed by any CRP method, has yet been covalently attached to a protein.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

REFERENCES

1. Agarwal, S. *Polym. Chem.* 2010, 1, 953-964.
2. Roy, I. and Jain, N. K. *Protein Science,* 2009, 24-36.
3. Mancini, R. J.; Lee, J.; Maynard, H. D. *J. Am. Chem. Soc.,* 2012, 134, 8474-8479.
4. Lee, J.; Lin, E.-W.; Lau, U. Y.; Hedrick, J. L.; Bat, E.; Maynard, H. D. *Biomacromolecules,* 2013, 14, 2561-2569.
5. Siegwart, D. J.; Bencherif, S. A.; Srinivasan, A.; Hollinger, J. O.; Matyjaszewski, K. *J. Biomed. Mater.* 2008, 87, 345-58.
6. Knop, K., Hoogenboom, R.; Fischer, D.; Schubert, U. S. *Angew. Chem. Int. Ed.* 2010, 49, 6288.
7. Alconcel, S. N. S.; Baas, A. S.; Maynard, H. D. *Polymer Chemistry* 2011, 2, 1442.
8. Gao, W.; Liu, W.; Christensen, T.; Zalutsky, M. R.; Chilkoti, A. *Proceedings of the National Academy of Sciences* 2010, 107, 16432.
9. Roberts, M. J.; Milton Harris, *Journal of Pharmaceutical Sciences* 1998, 87, 1440.
10. Markovsky, E.; Baabur-Cohen, H.; Eldar-Boock, A.; Omer, L.; Tiram, G.; Ferber, S.; Ofek, P.; Polvak, D.; Scomparin, A.; Satchi-Fainaro, R. *Journal of Controlled Release* 2012, 161, 446.
11. Duro-Castano, A.; Conejos-Sinchez, I.; Vicent, M. *Polymers* 2014, 6, 515.
12. Roberts, M. J.; Bentley, M. D.; Harris, J. M. *Advanced Drug Delivery Reviews* 2002, 54, 459.
13. Garman, A. J.; Barret Kalindjian, S. *FEBS Letters* 1987, 223, 361.
14. Veronese, F. M.; Largajolli, R.; Boccu, E.; Benassi, C. A.; Schiavon, O. *ApplBiochem Biotechnol* 1985, 11, 141.
15. Abuchowski, A.; Kazo, G. M.; Verhoest Jr, C. R.; Van Es, T.; Kafkewitz, D.; Nucci, M. L.; Viau, A. T.; Davis, F. F. *Cancer Biochemistry Biophysics* 1984, 7, 175.
16. Woghiren, C.; Sharma, B.; Stein, S. *Bioconjugate Chemistry* 1993, 4, 314.
17. Zalipsky, S.; Menon-Rudolph, S. In *Poly(ethylene glycol)*; American Chemical Society: 1997; Vol. 680, p 318.
18. Gaertner, H. F.; Offord, R. E. *Bioconjugate Chemistry* 1996, 7, 38.
19. Kozlowski, A.; Milton Harris, J. *Journal of Controlled Release* 2001, 72, 217.
20. Iha, R. K.; van Horn, B. A.; Wooley, K. L. *Journal of Polymer Science Part A: Polymer Chemistry* 2010, 48, 3553.
21. Lundberg, P.; Lee, B. F.; van den Berg, S. A.; Pressly, E. D.; Lee, A.; Hawker, C. J.; Lynd, N. A. *ACS Macro Lett.* 2012, 1, 1240.
22. Dingels, C.; Muller, S. S.; Steinbach, T.; Tonhauser, C.; Frey, H. *Biomacrmolecules* 2013, 14, 448.
23. Yan-Ling, L.; Yun-Fei, N.; Feng, X.; Ya-Shao, C.: Pei, Z. *Journal of Biomaterials Science—Polymer Edition* 2010, 21, 1143.
24. Cerritelli, S.; Velluto, D.; Hubbell, J. A. *Biomacromolecules* 2007, 8, 1966.
25. Hey, T.; Knoller, H.; Vorstheim, P. In *Therapeutic Proteins*; Wiley-VCH Verlag GmbH & Co. KGaA: 2012, p 117.
26. Zhang, R., Jain, S.; Rowland, M.; Hussain, N.; Agarwal, M.; Gregoriadis, G. *Journal of Diabetes Science and Technology* 2010, 4, 532.
27. Yurkovetskiy, A.; Choi, S.; Hiller, A.; Yin, M.; McCusker, C.; Syed, S.; Fischman, A. J.; Papisov, M. I. *Biomacromolecules* 2005, 6, 2648.
28. Hardwicke, J.; Ferguson, E. L.; Moseley, R.; Stephens, P.; Thomas, D. W., Duncan, R. *Journal of Controlled Release* 2008, 130, 275.
29. Liu, Z.; Dong, C.; Wang, X.; Wang, H.; Li, W.; Tan, J.; Chang, J. *ACS Applied Materials & Interfaces* 2014, 6, 2393.
30. Grover, G. N.; Maynard, H. D. *Current Opinion in Chemical Biology* 2010, 14, 818.
31. Lutz, J.-F.; Andrieu, J.; Üzgün, S.; Rudolph, C.; Agarwal, S. *Macromolecules* 2007, 40, 8540.
32. Riachi, C.; Schüwer, N.; Klok, H.-A. *Macromolecules* 2009, 42, 8076.
33. Delplace, V.; Tardy, A.; Harrisson, S.; Mura, S.; Gigmes, D.; Guillaneuf, Y.; Nicolas, J. *Biomacromolecules* 2013, 14, 3769.
34. Hedir, G. G.; Bell, C. A.; Ieong, N. S.; Chapman, E.; Collins, I. R., O'Reilly, R. K.; Dove, A. P. *Macromolecules* 2014.
35. Siegwart, D. J.; Bencherif, S. A., Srinivasan, A.; Hollinger, J. O.; Matyjaszewski, K. *Journal of Biomedical Materials Research* Part A 2008, 87A, 345.
36. Kobben, S.; Ethirajan, A.; Junkers, T. *Journal of Polymer Science Part A: Polymer Chemistry* 2014, n/a.
37. Xu, N.; Wang, R.; Du, F.-S.; Li, Z.-C. *J Polym Sci Pol Chem* 2009, 47, 3583.
38. Li, L.; Wang, J.; Obrinske, M.; Milligan, I.; O'Hara, K.; Bitterman, L.; Du, W. *Chemical Communications* 2015, 51, 6972.
39. Li, L.; Xu, Y.; Milligan, I.; Fu, L.; Franckowiak, E. A.; Du, W. *Angewandte Chemie—International Edition* 2013, 52, 13699.
40. Congdon, T.; Wilmet, C.; Williams, R.; Polt, J.; Lilliman, M.; Gibson, M. I. *European Polymer Journal* 2015, 62, 352.
41. Li, F.; Pei, D. F.; Huang, Q. R.; Shi, T. F.; Zhang, G. *Carbohyd Polym* 2014, 99, 728.
42. Xiao, N.; Liang, H.; Lu, J. *Soft Matter* 2011, 7, 10834.
43. Evaluate Ltd. Drug sales database, http://www.evaluategroup.com.
44. Alconcel, S. N. S.; Baas, A. S.; Maynard, H. D. *Polym. Chem.* 2011, 2, 1442.

45. Pfister, D.; Morbidelli, M., *Controlled Release* 2014, 180, 134.
46. Besheer, A.; Liebner, R.; Meyer, M.; Winter, G. In *Tailored Poymer Architectures for Pharmaceutical and Biomedical Applications*; Scholz, C., Kressler, J., Eds.; Amer Chemical Soc: Washington, 2013; Vol. 1135, p 215.
47. Pelegri-O'Day, E. M.; Lin, E.-W.; Maynard, H. D. *J. Am. Chem. Soc.* 2014, 136, 14323.
48. Chi, E. Y.; Krishnan, S.; Randolph, T. W.; Carpenter, J. F. *Pharm. Res.* 2003, 20, 1325.
49. "FDA Access Data", http://www.accessdata.fda.gov
50. Leader, B.; Baca, Q. J.; Golan, D. E. *Nat. Rev. Drug Discovery* 2008, 7, 39.
51. Keefe, A. J.; Jiang, S. *Nat. Chem.* 2012, 4, 59.
52. Nguyen, T. H.; Kim, S.-H.; Decker, C. G.; Wong, D. Y.; Loo, J. A.; Maynard, H. D. *Nat. Chem.* 2013, 3, 221.
53. Mancini, R. J.; Lee, J.; Maynard, H. D. *J. Am. Chem. Soc.* 2012, 134, 8474.
54. Lee, J.; Lin, E.-W.; Lau, U. Y.; Hedrick, J. L.; Bat, E.; Maynard, H. D. *Biomacromolecules* 2013, 14, 2561.
55. Bat, E.; Lee, J.; Lau, U. Y.; Maynard, H. D. *Nature Communications* 2015, 6.
56. Lee, J.; Ko, J. H.; Lin, E.-W.; Wallace, P.; Ruch, F.; Maynard, H. D. *Polym. Chem.* 2015, 6, 3443.
57. Jain, N. K.; Roy, I. *Protein Sci.* 2009, 18, 24.
58. Congdon, T.; Notman, R.; Gibson, M. I. *Biomacromolecules* 2013, 14, 1578.
59. Stidham, S. E.; Chin, S. L.; Dane, E. L.; Grinstaff, M. W. *Journal of the American Chemical Society* 2014, 136, 9544.
60. Hu, J.; Zhao, W.; Gao, Y.; Sun, M.; Wei, Y.; Deng, H.; Gao, W. *Biomaterials* 2015, 47, 13.
61. Hey, T.; Knoller, H.; Vorstheim, P. In *Therapeutic Proteins*; Wiley-VCH Verlag GmbH & Co. KGaA: 2012, p 117.
62. Zhang, R.; Jain, S.; Rowland, M.; Hussain, N.; Agarwal, M.; Gregoriadis, G. *J. Diabetes Sci. Technol.* 2010, 4, 532.
63. Hardwicke, J.; Moseley, R.; Stephens, P.; Harding, K.; Duncan, R., Thomas, D. W. *Mol. Pharmaceutics* 2010, 7, 699.
64. Hardwicke, J. T.; Hart, J.; Bell, A.; Duncan, R.; Thomas, D. W.; Moseley, R. *J. Controlled Release* 2011, 152, 411.
65. Decker, C. G.; Maynard, H. D. *European Polymer Journal* 2015, 65, 305.
66. Xu, N.; Wang, R.; Du, F.-S.; Li, Z.-C. *J Polym Sci Pol Chem* 2009, 47, 3583.
67. Slavin, S.; Burns, J.; Haddleton, D. M.; Becer, C. R. *European Polymer Journal* 2011, 47, 435.
68. Campos, L. M.; Killops, K. L.; Sakai, R.; Paulusse, J. M. J.; Damiron, D.; Drockenmuller, E.; Messmore, B. W.; Hawker, C. *J. Macromolecules* 2008, 41, 7063.
69. Ende, A. E. v. d.; Kravitz, E. J.; Harth, E. *Journal of the American Chemical Society* 2008, 130, 8706.
70. Silvers, A. L.; Chang, C.-C.; Emrick, T. *J Polym Sci Pol Chem* 2012, 50, 3517.
71. Parrish, B.; Quansah, J. K.; Emrick, T. *Journal of Polymer Science Part A: Polymer Chemistry* 2002, 40, 1983.
72. Parrish, B.; Breitenkamp, R. B.; Emrick, T. *Journal of the American Chemical Society* 2005, 127, 7404.
73. Pratt, R. C.; Lohmeijer, B. G. G.; Long, D. A.; Waymouth, R. M.; Hedrick, J. L. *Journal of the American Chemical Society* 2006, 128, 4556.
74. Lohmeijer, B. G. G.; Pratt, R. C.; Leibfarth, F.; Logan, J. W.; Long, D. A.; Dove, A. P.; Nederberg, F.; Choi, J.; Wade, C.; Waymouth, R. M.; Hedrick, J. L. *Macromolecules* 2006, 39, 8574.
75. Wang, R.; Chen, W.; Meng, F.; Cheng, R., Deng, C.; Feijen, J.; Zhong, Z. *Macromolecules* 2011, 44, 6009.
76. Takasu, A.; Houjyou, T.; Inai, Y.; Hirabayashi, T. *Biomacromolecules* 2002, 3, 775.
77. Lee, J.; Lin, E. W.; Lau, U. Y.; Hedrick, J. L.; Bat, E.; Maynard, H. D. *Biomacromolecules* 2013, 14, 2561.
78. Diamond, R. *J. Mol. Biol.* 1974, 82, 371.
79. Bentley, M. D.; Roberts, M. J.; Harris, J. M. *J. Pharm. Sci.* 1998, 87, 1446.
80. Gomez d'Ayala, G.; Malinconico, M.; Laurienzo, P.; Tardy, A.; Guillaneuf, Y.; Lansalot, M.; D'Agosto, F.; Charleux, B. *J. Polym. Sci., A, Polym. Chem.* 2014, 52, 104.
81. Delplace, V.; Tardy, A.; Harrisson, S.; Mura, S.; Gigmes, D.; Guillaneuf, Y.; Nicolas, J. *Biomacromolecules* 2013, 14, 3769.
82. Siegwart, D. J.; Bencherif, S. A.; Srinivasan, A.; Hollinger, J. O.; Matyjaszewski, K. *J. Biomed Mater. Res. Part A* 2008, 87A, 345.
83. Xiao, N.; Liang, H.; Lu, J. *Soft Matter* 2011, 7, 10834.
84. "FDA Access Data", http://www.accessdata.fda.gov
85. Bailey, W. J.; Wu, S. R.; Ni, Z. *Makromolekulare Chemie—Macromoleclar Chemistry and Physics* 1982, 183, 1913.
86. Bailey, W. J.; Ni, Z.; Wu, S. R. *Macromolecules* 1982, 15, 711.
87. Sizovs, A.; Xue, L.; Tolstyka, Z. P.; Ingle, N. P.; Wu, Y.; Cortez, M.; Reineke, T. M. *Journal of the American Chemical Society* 2013, 135, 15417.
88. Johnson, D. A. *Carbohydr. Res.* 1992, 237, 313.
89. Campos, L. M.; Killops, K. L.; Sakai, R.; Paulusse, J. M. J.; Damiron, D.; Drockenmuller, E.; Messmore, B. W.: Hawker, C. *J. Macromolecules* 2008, 41, 7063.
90. Decker, C.; Maynard, H. *European Polymer Journal* 2015, 65, 305.
91. Wada, M.; Miyazawa, Y.; Miura, Y. *Polymer Chemistry* 2011, 2, 1822.
92. Kanai, M.; Mortell, K. H.; Kiessling, L. L. *J. Am. Chem. Soc.* 1997, 119, 9931.
93. Gestwicki, J. E.; Cairo, C. W.; Strong, L. E.; Oetjen, K. A.; Kiessling, L. L. *J. Am. Chem. Soc.* 2002, 124, 14922.
94. Ladmiral, V.; Mantovani, G.; Clarkson, G. J.; Cauet, S.; Irwin, J. L.; Haddleton, D. M. *J Am Chem Soc* 2006, 128, 4823.
95. Paz-Alfaro, K. J.; Ruiz-Granados, Y. G.; Uribe-Carvajal, S.; Sampedro, J. G. *Journal of Biotechnology* 2009, 141, 130.

I claim:
1. A biodegradable trehalose polymer, wherein the polymer consists of the general structure:

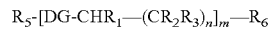

$$R_5\text{-[DG-CHR}_1\text{—(CR}_2\text{R}_3)_n]_m\text{—R}_6$$

wherein $R_1$-$R_3$ are independently selected from hydrogen or a side chain comprising at least one carbon atom, and wherein at least one of $R_1$-$R_3$ is a side chain comprising -L-trehalose, wherein L is a linker molecule that links a thiolated trehalose to the polymer through at least one thiol group of the thiolated trehalose, wherein DG is a biodegradable group, and
wherein $R_5$ and $R_6$ are end groups, and
wherein n=0-10,
wherein m≥1.

2. The polymer of claim 1, wherein $R_5$ and $R_6$ are independently selected from the group consisting of -Alkyl, -Alkenyl, -Alkynyl, -Aryl, disulfide, pyridyl disulfide, 5-thio-2-nitrobenzoic acid, disulfide reductants, Michael acceptors, maleimides, maleimide derivatives, dihalomaleimides, vinyl groups, vinyl sulfones, acryloyl derivatives, haloacetyl, alkyl halide derivatives, aziridines, arylating agents, isothiocyanates, isocyanates, acryl azides, activated esters, N-hydroxysuccinimide esters, para-nitrophenyl esters, sulfonyl chlorides, aldehydes and glyoxals (with or without reductive amination), epoxides (also called oxiranes), carbonates, arylating agents, imidoesters, carbodiimides, anhydrides, primary amines, secondary amines, tertiary amines, diazoalkanes, diazoacetyls, carbonyldiimidazoles, carbonates, chloroformates, alkyl halogens, aminooxy (hydroxylamines), hydrazines, and biomolecules.

3. The polymer of claim 1, wherein $R_5$ and $R_6$ are independently selected from the group consisting of -Alkyl, -Alkenyl, -Alkynyl, -aryl, —C(CN)(Alkyl)$_2$, —S$_2$C—S-Alkyl, —C(CO)(Alkyl)-(OCH$_2$CH$_2$)$_n$—COO—CH$_2$CH$_2$—CO-Alkyl (n=1-10), —(CH$_3$)CHCOO-Aryl, —CH(CH$_3$)—CONH—(CH$_2$)$_n$—SS-Aryl (n=1-10), and biomolecules.

4. The polymer of claim 1, wherein DG comprises at least one ester group.

5. The polymer of claim 4, wherein the ester group is in the backbone of the polymer.

* * * * *

UNITED STATES PATENT AND TRADEMARK OFFICE
CERTIFICATE OF CORRECTION

PATENT NO. : 10,899,879 B2
APPLICATION NO. : 15/503350
DATED : January 26, 2021
INVENTOR(S) : Heather D. Maynard It is certified that error appears in the above-identified patent and that said Letters Patent is hereby corrected as shown below:

In the Specification

Column 5, Lines 60-61, "(hydroxylanines) should be --(hydroxylamines)--.

Column 11, Line 16, "carbami de" should be --carbamide--.

Column 12, Lines 28-29, "ervthropietin" should be --erythropoietin--.

Column 12, Line 52, "Vila" should be --VIIa--.

Column 12, Line 64, "Rashuricase" should be --Rasburicase--.

Column 27, Line 63, "NNR" should be --NMR--.

Column 33, Line 49, "was" should be --was performed by SDS-PAGE before the mixture was purified by centrifugal filtration against 30 kD MWCO.--.

Column 38, Line 11, "(dt, J=6.8, 2.7 Hz H)" should be --(dt, J=6.8, 2.7 Hz 1H)--.

Column 45, Line 21, "lysozme" should be --lysozyme--.

Column 49, Line 50, "Povak" should be --Polyak--.

Column 49, Line 53, "Conejos-Sinchez" should be --Conejos-Sánchez--.

Column 50, Line 12, "Biomacrmolecules" should be --Biomacromolecules--.

Column 50, Line 42, "leong" should be --Ieong--.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*